United States Patent [19]
Miyata et al.

[11] Patent Number: 6,098,405
[45] Date of Patent: Aug. 8, 2000

[54] DRIVE UNIT FOR MEDICAL EQUIPMENT

[75] Inventors: Shinichi Miyata; Kiyotaka Ito, both of Tokyo, Japan

[73] Assignee: Nippon Zeon Co., Ltd., Tokyo, Japan

[21] Appl. No.: 09/091,356

[22] PCT Filed: Dec. 10, 1996

[86] PCT No.: PCT/JP96/03605

§ 371 Date: Jun. 18, 1998

§ 102(e) Date: Jun. 18, 1998

[87] PCT Pub. No.: WO97/22373

PCT Pub. Date: Jun. 26, 1997

[30] Foreign Application Priority Data

| Dec. 18, 1995 | [JP] | Japan | 7/329157 |
| Dec. 22, 1995 | [JP] | Japan | 7/335274 |
| Feb. 19, 1996 | [JP] | Japan | 8/031018 |
| Mar. 28, 1996 | [JP] | Japan | 8/073636 |
| Apr. 11, 1996 | [JP] | Japan | 8/089332 |

[51] Int. Cl.[7] .................................................. F15B 7/00
[52] U.S. Cl. ............................... 60/535; 60/592; 60/407
[58] Field of Search ............................ 60/535, 584, 592, 60/370, 375, 407, 428, 429; 91/265, 266, 275, 280, 339, 460

[56] References Cited

U.S. PATENT DOCUMENTS

| 1,835,977 | 12/1931 | Ernst et al. | 60/429 |
| 2,072,693 | 1/1937 | Volkert | 60/592 |
| 2,409,175 | 1/1946 | Adams et al. | 60/592 X |
| 2,456,869 | 1/1948 | Fowler | 60/592 X |
| 2,906,095 | 9/1959 | Whitehead, Jr. | 60/592 |
| 3,040,533 | 6/1962 | Heinrich | 60/584 X |
| 3,064,429 | 11/1962 | Hager | 60/535 X |
| 3,163,985 | 1/1965 | Bouyoucos | 60/398 |
| 3,955,557 | 5/1976 | Takagi | 600/16 |
| 3,967,447 | 7/1976 | Hegel | 60/592 X |
| 4,038,823 | 8/1977 | Mostert | 60/584 |
| 4,116,589 | 9/1978 | Rishton | 417/384 |
| 4,548,550 | 10/1985 | Tsuji | 417/390 |
| 4,583,525 | 4/1986 | Suzuki et al. | 128/1 D |
| 4,648,385 | 3/1987 | Oumi et al. | 128/1 D |
| 4,942,735 | 7/1990 | Mushika et al. | 60/416 |

FOREIGN PATENT DOCUMENTS

| 48-2787 | 1/1973 | Japan . |
| 62-227365 | 10/1987 | Japan . |
| 2-131770 | 5/1990 | Japan . |

*Primary Examiner*—John E. Ryznic
*Attorney, Agent, or Firm*—Armstrong, Westerman, Hattori, McLeland & Naughton

[57] ABSTRACT

A tube-line pressure sensor of a medical-appliance driving apparatus detects the interior pressure of a tube line. If the pressure detected by a tube-line pressure sensor is equal to or less than a predetermined value, a first solenoid valve is closed, while a second solenoid valve is opened, whereby a gas is supplied from a secondary gas tank to the tube line. The amount of gas supplied to the tube line is calculated based on a pressure change in the tank detected by a tank pressure sensor. In actual use, natural gas leakage during normal operation can be clearly distinguished from abnormal gas leakage due to an accident. The interior pressure of the tube line is detected at a time when the balloon is about to inflate from the deflated state, and a gas supply system supplies the driving gas to the tube line so that the detected pressure becomes a preset pressure value. A controller can change the preset pressure value. If the inflation/deflation cycle of the balloon is short, a cycle of inflation is suspended in order to stabilize the interior pressure of the balloon and the pressure is detected at the next inflation immediately after the suspension. The gas is supplied based on this newly detected pressure. Preferably, the driving apparatus has relief passages (e.g., grooves) for driving residual fluid residing between the first or second inner surface and a diaphragm away into an input port or an output port, respectively, when the diaphragm contacts either of the first and second inner surfaces.

24 Claims, 30 Drawing Sheets

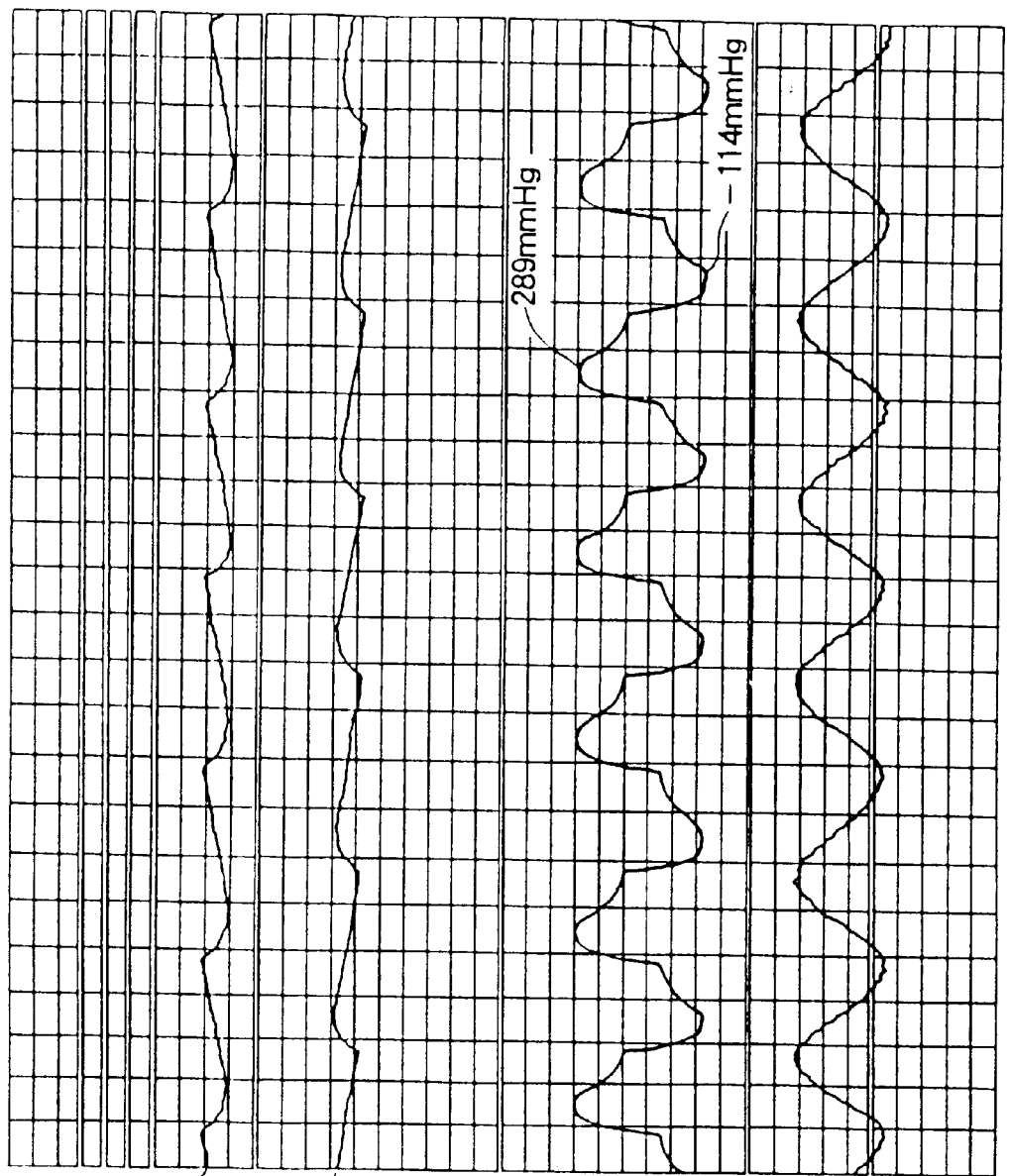

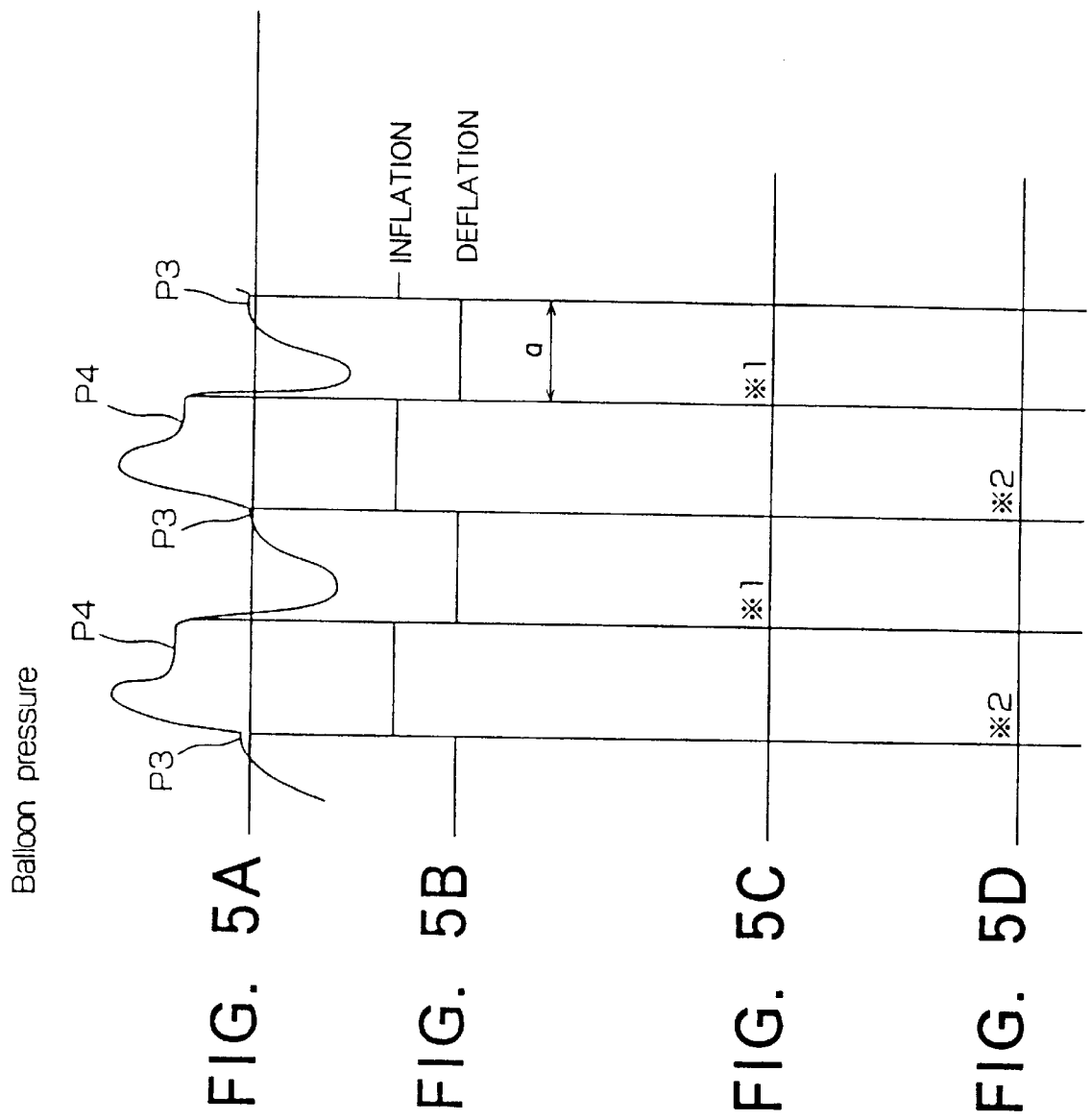

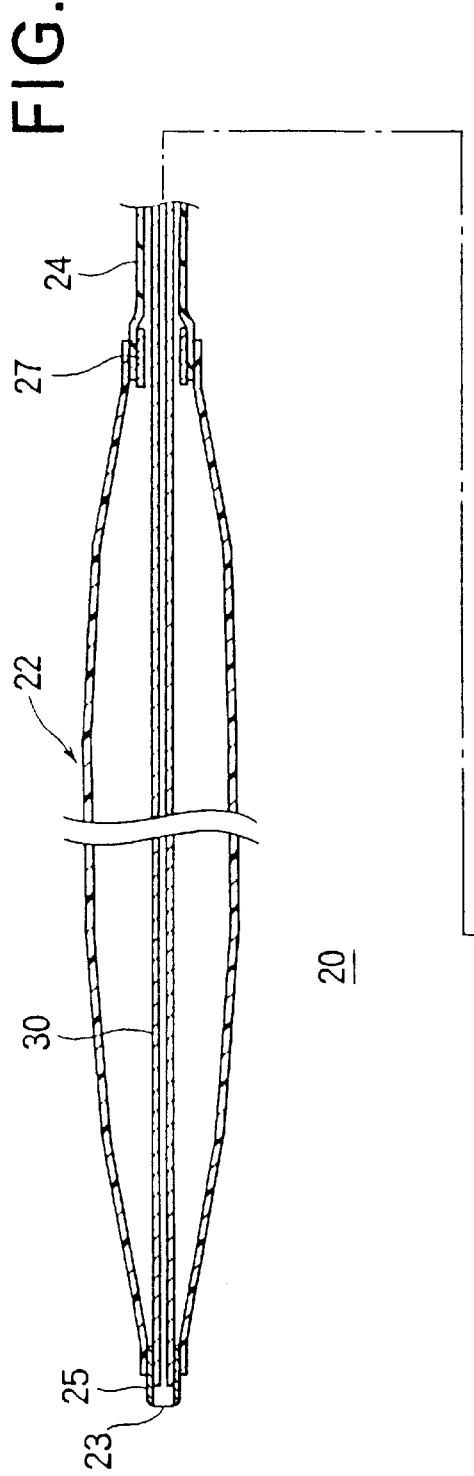
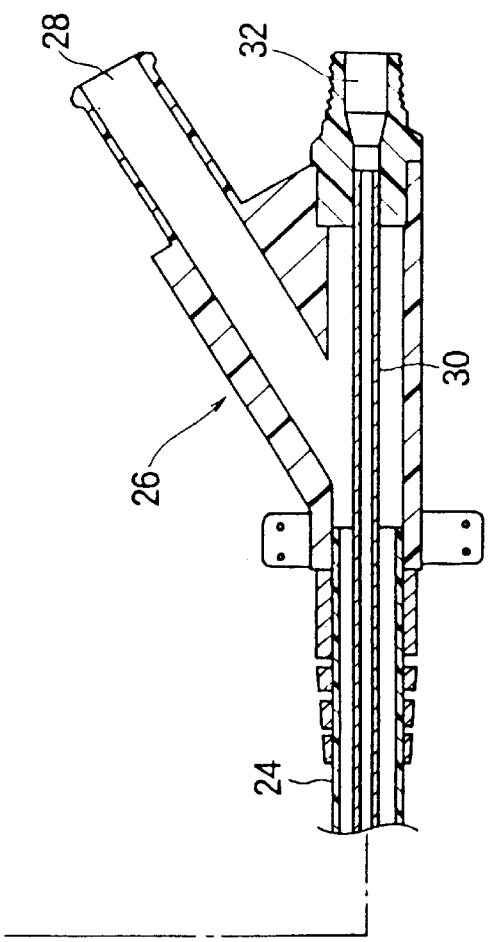
FIG. 7

FIG. 18A  FIG. 18B
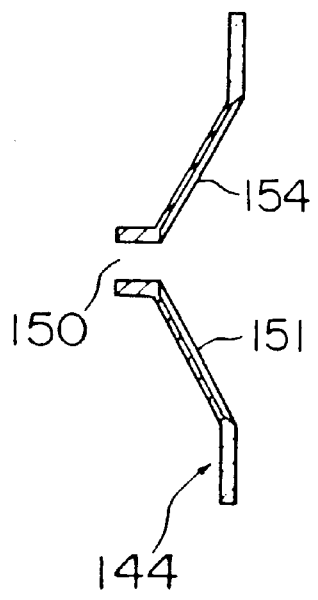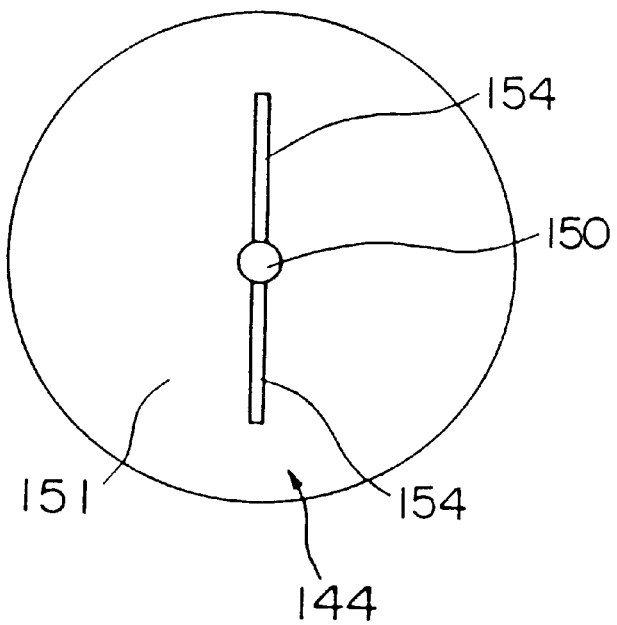
FIG. 19A  FIG. 19B
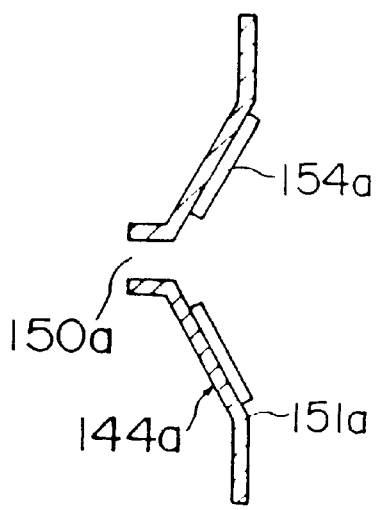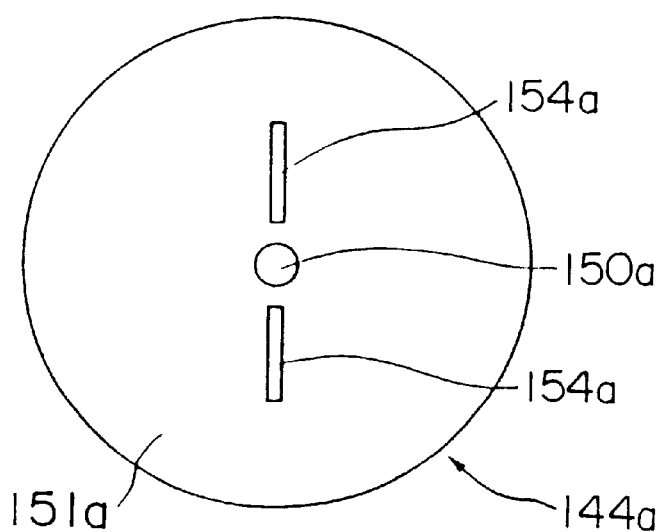

DRIVE UNIT FOR MEDICAL EQUIPMENT

FIELD OF THE INVENTION

This invention relates to a driving apparatus for driving medical appliances, such as an artificial heart and an intra-aorta balloon pump (IABP), by alternately outputting a positive pressure and a negative pressure, and to a pressure-transfer isolator and a monitor used in the driving apparatus.

BACKGROUND OF THE INVENTION

IABP balloon catheters are often used in medical treatment of heart diseases. In the treatment, a balloon catheter is inserted into the artery near the heart f the patient, and the balloon is inflated and deflated in synchronization with the heart beat of the patient in order to assist or activate the heart function. Japanese Patent Application Laid-open No. 60-106464 (hereinafter "JP '464") discloses a medical-purpose driving apparatus for inflating and deflating such balloons.

The driving apparatus disclosed in JP '464 has a primary tube line and a secondary tube line, which are isolated from each other by a pressure-transfer isolator (simply called an isolator, or generally named a volume limiting device (VLD)). A change of pressure occurring in the primary tube line is transferred to the secondary tube line via the isolator without allowing gas flow between the secondary tube line and the primary tube line, and the resultant pressure change in the secondary tube line causes the balloon to inflate and deflate. The reason why the primary and secondary tube lines are separated from each other is that different kinds of fluid are used in these two lines, namely, one has a driving gas for actually driving the balloon, the other has a source gas from which a positive pressure and a negative pressure are generated. This is required to improve the inflation/deflation response of the balloon and to keep the secondary tube line sealed in order to prevent gas leakage except the leakage due to diffusion. This arrangement is capable of generating a pressure at a low cost, while reducing consumption of an expensive fluid used in the secondary tube line. The pressure-transfer isolator is located between the pressure source and the balloon in order to prevent excessive gas from flowing into the balloon when inflating and deflating the balloon.

In this IABP balloon catheter, helium gas, which has a small mass and a high response ability, is preferably used as the fluid to fill the secondary tube line. In this case, the helium gas functions as a driving shuttle gas. However, because of its small molecular weight, helium gas diffuses through the tube wall or the balloon film even if there are no pin holes in the secondary tube line. If helium gas is enclosed in the sealed secondary tube line, and if the balloon is continuously driven for 20 minutes to 30 minutes, the gas pressure inside this tube line decreases by several millimeters (mm) of mercury (Hg).

For this reason, the helium gas must be appropriately supplied to the secondary tube line during the use of the balloon catheter. If additional helium gas is not supplied, the amount of helium gas inside the secondary tube line gradually decreases and, finally, the balloon cannot be sufficiently inflated, which means that the balloon cannot aid the heart function of the patient any longer. Some gas supply systems are known, which monitor the interior pressure of the secondary tube line using a pressure sensor, and which supply gas so that the detected pressure does not drop below a predetermined value. In these systems, the solenoid valve is opened certain times in a short amount of time to supply helium gas from the high-pressure gas cylinder via the helium gas tank in which the pressure is adjusted to a secure level.

However, if the helium gas is additionally supplied without limitation, and if a pin hole is formed in the balloon by accident, then a great amount of gas may flow into the blood vessel of the patient, which may cause gas obturation and may be fatal to the patient. Accordingly, in the conventional driving apparatuses, the pressure of the helium gas is kept relatively low using a mechanical regulator, and the gas is supplied to the secondary tube line several times separately. Also, a mechanism for monitoring the total number of opening/closing actions of the solenoid valves in the series of gas supply operations and the time interval between gas supply operations is provided for the purpose of regulating the gas supply.

However, in the conventional apparatuses, the amount of helium gas supplied per unit time cannot be accurately known even if the number of opening/closing actions of the solenoid valve is monitored. It is impossible for the conventional apparatuses to keep the same interior pressure of the helium gas tank before and after the switching of the solenoid valve. In addition, the switching time of the solenoid valve itself varies, and the balloon pressure is affected by the patient's blood pressure. For these reasons, the amount of helium gas supplied per opening of the valve or the number of opening/closing actions of the valve is not stable. Thus, it is difficult to accurately know the total amount of supplied helium gas based on the number of opening/closing actions of the solenoid valve. If a strict restriction is imposed on the number of switching actions of the valve and the time interval between gas supply operations, during which the interior pressure of the secondary tube line gradually decreases, then an improper alarm may be given due to the influence of fluctuation in the opening/closing time of the solenoid valve. On the other hand, if the monitoring restriction is loosened, it becomes difficult to distinguish abnormal gas leakage due to, for example, a pin hole formed in the balloon catheter or the secondary tube line, from the natural gas leakage (or diffusion) during the normal operation.

Even if the relationship between the number of switching actions of the solenoid valve versus time is placed on a chart, this chart does not help the operator (or the observer) distinguish abnormal gas leakage from natural gas leakage because the number of switching actions does not indicate the accurate amount of helium gas additionally supplied.

By the way, several types of balloon catheters for IABP having different volumes are generally prepared so as to meet with the patients' physiques. In the conventional apparatuses, when the balloon catheter connected to the secondary tube line is replaced with another balloon catheter having a different volume, the pressure-transfer isolator is also changed according to the size (volume) of the new balloon catheter. Some pressure-transfer isolators have a mechanism for adjusting the stroke of the diaphragm, which serves as the pressure transfer element, according to the size of the balloon catheter. In these isolators, the stroke of the diaphragm is varied as the balloon catheter is changed without replacing the isolator itself, so that the appropriate amount of driving gas is supplied to drive the new balloon catheter. Unfortunately, this type of driving apparatus is likely to become large because of its mechanical structure and, in addition, the operator must set the stroke of the diaphragm to an appropriate value each time the balloon catheter and the pressure-transfer isolator are changed. If a motor is used as the driving mechanism in such a pressure-transfer isolator, the response speed of the stroke is not fast enough. For these reasons, the pressure-transfer isolator itself is generally changed in the conventional driving apparatuses, rather than adjusting the stroke of the diaphragm.

If a pressure-transfer isolator, designed for a small volume balloon, is used to drive a large volume of balloon catheter, it cannot sufficiently aid the heart function of the patient. Conversely, if a pressure-transfer isolator, designed for a large volume balloon is used to drive a small volume of balloon catheter, excessive pressure is applied to the balloon, and danger of gas leakage increases.

In order to replace the pressure-transfer isolator without causing gas leakage, appropriate sealing structures must be provided to both the pressure-transfer isolator and the receiving part of the housing of the apparatus. These sealing structures must be tightened appropriately. This requires a high rigidity in the pressure-transfer isolator and the receiving part of the housing. Consequently, both the weight and the cost, of the entire apparatus, increase. Although a variable-stroke pressure-transfer isolator can keep its chamber airtight using fixed connecting means (e.g., screws or adhesive), it has drawbacks as explained above.

In general, rubber diaphragms used in pressure-transfer isolators are fatigued through use, and they must be replaced when the cumulative driving numbers approach the marginal value. However, since the pressure-transfer isolator is often changed according to the volume of the balloon catheter to be used, it is difficult to keep a record of the cumulative driving number of each diaphragm and to accurately specify the time for replacement of the diaphragm. The diaphragm of a pressure-transfer isolator is generally changed earlier in order to ensure safe operation, which further increases both the cost and the labor.

Japanese Patent Application Laid-open No. 5-10952 (hereinafter "JP '952") discloses a technique for driving a medical appliance, which does not require the pressure-transfer isolator to be replaced or adjusted even if a different volume of balloon catheter is used. In JP '952, the interior pressure of the secondary tube line (including tubes and hoses) on the balloon catheter side is monitored and, simultaneously, the balloon pressure is also detected at a timing of switching a driving state of balloon to a deflated state from a inflated state. A gas is supplied into the balloon side tube line so that the pressure (i.e., the plateau pressure) in the inflation state is kept constant. In this method, the interior pressure is automatically adjusted whenever a different volume of balloon catheter is used and thus, manual adjustment by the operator is not required.

However, this driving apparatus does not take a slight change of the balloon volume into account, which slight change in balloon volume may be caused by, for example, the fatigue of the balloon, inappropriate pressure application, bend of the blood vessel of the patient, or unexpected accidents (such as, the balloon getting stuck in swelling inside the blood vessel). Accordingly, the driving apparatus keeps on supplying helium gas to the tube even if the balloon volume changes because one of the situations explained above, occur. In addition to this, the life of the distorted balloon becomes shorter, which is undesirable.

In the apparatus of JP '952, the balloon is degassed when the blood pressure of the patient increases as the patient recovers, and when the blood pressure of the patient reaches a prescribed upper limit with respect to the interior pressure of the balloon. This degassing may result in inadequate inflation of the balloon.

If the balloon is left inside the patient's body in these undesirable situations, a blood clot is formed on the balloon surface, which may cause a serious side effect.

Japanese Patent Application Laid-open No. 5-192396 (hereinafter "JP '396") discloses a technique for gradually decreasing the opening time of the positive-pressure timing valve provided in the primary tube line in order to gradually reduce the medical aid given by the balloon catheter to the patient's heart beat as the patient's heart function recovers.

However, this technique cannot precisely control the contribution ratio of the balloon catheter to the patient's heart function because the patient's blood pressure changes every moment, and because the opening time of the valve varies due to the mechanical structure of the valve.

Generally, in the conventional driving apparatuses described above, the inflation/deflation rate of the balloon increases as the patient's heart beat rate increases and, consequently, the apparent pressure (i.e., the detected pressure) becomes lower than the actual pressure. In other words, when the inflation/deflation rate is high, the pressure of the secondary tube line starts decreasing before the actual pressure reaches the originally determined maximum inflation state. If the gas is supplied based on this information, an excessive amount of gas is introduced into the secondary tube line, which is not desirable for the patient or for the durability of the balloon.

To overcome this problem, the gas supply may be suspended for a while when the patient's heart beat rate is high. However, if such a situation continues for very long, the helium gas escapes from the secondary tube line through penetration and diffusion and the function of the balloon, to aid the heart beat rate of the patient, is lessened.

In some other conventional driving apparatuses, the entire gas in the secondary tube line is regularly replaced with new gas. In this case, the gas consumption increases, and if a relatively expensive helium gas is used as the driving gas, the apparatus becomes uneconomical. In addition, when substituting the gas, the balloon is not driven for several tens of seconds, during which the medical aid for the heart function of the patient is suspended.

Another problem of the conventional driving apparatuses using a pressure-transfer isolator is that a small peak appears in each pulse of the detected pressure of the secondary tube line. This peak prevents accurate detection of the interior pressure of the secondary tube line.

SUMMARY OF THE INVENTION

Therefore, it is a first object of the present invention to provide a medical-appliance driving apparatus, in which abnormal gas leakage is clearly distinguished from natural gas leakage during normal operation.

It is a second object of the present invention to provide a compact and light medical-appliance driving apparatus that does not require the driving element to be changed even though the balloon catheter is replaced with a different volume of balloon catheter, and to provide a method of using such a driving apparatus. In this driving apparatus, it is easy to monitor and specify the time to change the driving element, and contribution to the medical aid of the patient's heart function can be easily controlled in accordance with the condition of the patient.

It is a third object of the present invention to provide a medical-appliance driving apparatus that can supply an appropriate amount of gas to the tube line, including a device to be driven, even if the inflation/deflation cycle of the device being driven is short or irregular.

It is a fourth object of the present invention to provide a pressure-transfer isolator that makes it possible to accurately detect a momentary stable pressure among the fluctuated pressure applied to a device being driven, such as a balloon catheter, and that operates in such a manner that the operation state of the driven device is precisely known based on the detected pressure.

Medical-Appliance Driving Apparatus in the First Aspect of the Invention

In order to achieve the above-stated first object of the present invention, the medical-appliance driving apparatus, in the first aspect of the invention, comprises: a pressure generator for alternately applying a positive pressure and a negative pressure to a tube line connected to a device to be driven so that the device inflates and deflates repeatedly; a tube-line pressure sensor for detecting the interior pressure of the tube line; a gas supply system for supplying a gas into the tube line; and a controller for controlling the amount of gas supplied by the gas supply system to the tube line.

The gas supply system comprises: a primary gas tank filled with a relatively high-pressure gas; a first valve connected to the output side of the primary gas tank, the first valve being opened and closed at an appropriate timing; a secondary gas tank connected to the output side of the primary gas tank so as to allow gas flow therebetween when the first valve is open; a tank-pressure sensor for detecting the interior pressure of the secondary gas tank; and a second valve, connected to the output side of the secondary gas tank, for adjusting the amount of the gas supplied from the secondary gas tank into the tube line by opening and closing the valve.

When the pressure detected by the tube-line pressure sensor is not more than a predetermined value, the controller closes the first valve, while opening the second valve, in order to allow the driving gas to be supplied from the secondary gas tank to the tube line. At the same time, the controller calculates the amount of gas that was supplied to the tube line based on a change in the tank pressure detected by the tank-pressure sensor.

Preferably, the tube-line pressure sensor detects the interior pressure of the tube line at a timing of switching a state of the device from its deflated state to its inflated state. The controller determines if the detected pressure is equal to or smaller than the predetermined value.

Examples of the device to be driven include a balloon catheter for IABP.

With this driving apparatus, the amount of gas supplied to both the tube line and the driven device is calculated in the following manner.

First, when the pressure detected by the tube-line pressure sensor is below the predetermined value, the first valve is opened, while the second valve is closed, whereby the gas can be supplied from the secondary gas tank to the tube line. The interior pressure of the tank is detected by the tank-pressure sensor before and after the gas supply. During this time, the secondary tank is disconnected from the primary gas tank by the first value. Accordingly, the amount of gas that has flowed to the tube line from the secondary tank is obtained from the difference in pressure (P1–P2) before and after the gas supply and the volume V of the secondary gas tank. The amount of supplied gas is proportional to (P1–P2)*V.

The calculated gas amount is recorded in time series. The recording medium includes, but is not limited to, semiconductor memories, magnetic discs, optical recording media, and other recording media. The gas amount data can be output either on the screen or on paper, as is necessary. By observing the recorded data, it can be determined that abnormal gas leakage has occurred when the time interval of gas supply becomes shorter and when the calculated amount of supplied gas starts increasing. This system can send out an alarm for abnormal gas leakage promptly based on the changes in the gas supply interval and the gas supply amount. The central processing unit or CPU reads out the gas supply data stored in the recording medium in time series, and an alarm can be automatically given if the CPU has determined from the data that an abnormal gas leakage has occurred.

In this manner, the amount of gas supplied to the tube line and the device being driven is known precisely without being affected by the variation in the mechanical structure and the condition of the patient. Consequently, abnormal gas leakage due to, for example, a pin hole formed in the tube line or the device being driven, can be clearly distinguished from natural gas leakage during normal operation, and an alarm can be given without fail whenever abnormal gas leakage is detected.

Medical-Appliance Driving Apparatus in the Second Aspect of the Invention

In order to achieve the above-stated second object of the present invention, the medical-appliance driving apparatus, in the second aspect, comprises: a pressure generator for alternately applying a positive pressure and a negative pressure to a tube line connected to a device to be driven so that the device inflates and deflates repeatedly; a tube-line pressure sensor for detecting the interior pressure of the tube line; a gas supply system both for sampling the interior pressure detected by the tube-line pressure sensor at a timing of switching a state of the driven device from the deflated state to the inflated state and for supplying a gas into the tube line so that the detected pressure reaches a predetermined pressure value; and a controller for changing the predetermined pressure value.

As a modification of this driving apparatus, a medical-appliance driving apparatus comprises: a primary pressure generator for alternately generating a positive pressure and a negative pressure; and a secondary pressure generator comprising a pressure-transfer isolator. The pressure-transfer isolator has a first chamber, to which the positive pressure and the negative pressure generated by the primary pressure generator are introduced via a primary tube line, and a second chamber which is isolated from the first chamber in a sealed manner, to which at least a portion of the pressure in the first chamber is transferred. This modification also comprises: a secondary tube line connected to both the second chamber and to a device to be driven to repeat inflation and deflation; a pressure sensor for detecting the interior pressure of the secondary tube line; a gas supply system; and a controller. The gas supply system first fills the secondary tube line with a gas under a predetermined pressure, while the device to be driven is in the deflated state. The predetermined gas pressure is defined according to the volume of the device to be driven. Then, the gas supply system samples the interior pressure detected by the tube-line pressure sensor at a timing of switching a state of the device from the deflated state to the inflated state, and supplies additional gas into the tube line so that the detected pressure reaches the predetermined pressure defined by the volume of the device to be driven. The controller can change the preset value of the gas pressure in the tube line.

In this context, "the timing of switching" means to include the timing right before the actual switching timing and means any one of the point of time within a time duration of about 50 ms before and after the generation of an electric signal for controlling a machine, for example a valve to inflate or deflate the device because the mechanical response time of the machine (which is generally several milliseconds to several tens of milliseconds) must be taken into account.

With this driving apparatus, different devices (e.g., balloon catheters) having different volumes can be appropriately driven under appropriate pressures, without replacing a driving element for changing driving amplitude of the secondary pressure generator, which comprises a pressure-transfer isolator. Prior to replacing the driven device with another device having a different volume, the fill-up gas pressure in the secondary tube line is newly set according to the volume of the new device to be driven. During the actual use, the tube-line pressure sensor detects the interior pressure of the secondary tube line at a timing of switching a state of the device being driven to the inflated state from the deflated state in response to the switching of the valve and the like. The gas supply system supplies the driving gas to the secondary tube line so that the detected pressure reaches the newly determined pressure value.

If a balloon catheter having a small volume is connected to the driving apparatus, the gas pressure in the secondary tube line is set relatively low. For example, if the volume of the balloon catheter is 40 cc, the gas pressure in the secondary tube line is set to 10 mm Hg±5 mm Hg (gauged pressure), and if a balloon catheter of 30 cc is used, the gas pressure is set to −80 mm Hg±5 mm Hg (gauged pressure). In the conventional driving apparatus, the driving amplitude is changed by replacing the parts of the secondary pressure generator which comprises a pressure-transfer isolator, and the gas pressure in the secondary tube line is the same regardless of the volume of the device to be driven.

In contrast, in the present invention, the gas pressure in the secondary tube line is changed according to the volume of the device to be driven without replacing the driving elements. If a small volume of balloon catheter is used, the gas pressure is set lower, and it is controlled so that the lower pressure is maintained. Consequently, the pressure, at the end of the deflation cycle of the device, is lowered as compared with the pressure of the conventional device, and the pressure difference, between the beginning and the end of the deflation, becomes large. This allows the device being driven to deflate faster, and can reduce the load on the heart of the patient.

Another advantage of the invention is that the parts of the secondary pressure generator (i.e., the pressure-transfer isolator) do not have to be changed even when the driving amplitude of the secondary pressure generator is varied. This means that the secondary pressure generator (i.e., the pressure-transfer isolator) can be fixed and, accordingly, a rigidity, presupposing a cartridge-type interchange, is not required any longer. As a result, the total weight of the driving apparatus can be reduced. The total oscillating time and the number of oscillations of the membrane (i.e., the diaphragm) built in the pressure-transfer isolator are consistent with the driving time and the number of driving cycles of the driving apparatus. This facilitates the management and the maintenance of the membrane (or the diaphragm). The operator does not have to replace the parts of the pressure-transfer isolator, or adjust the driving stroke of the membrane.

The driving apparatus of the invention is also capable of gradually decreasing the contribution ratio of the balloon catheter to the heart function of the patient when the patient is recovering. The gas pressure of the tube line connected to the device being driven is regulated at a time when the device being driven is about to inflate from the deflated state, so that the gas pressure is consistent with a predetermined pressure value. This predetermined pressure value can be changed according to the patient's condition. When the patient is recovering, the preset pressure value can be lowered in order to reduce the gas pressure in the tube line connected to the device being driven. Consequently, the inflation amount of the device and, therefore, the contribution ratio of the device to the patient's heart function both decrease to a desired level. As compared with the technique disclosed in JP '396, the present invention has an advantage that the contribution ratio of the device to the patient's heart function is precisely controlled without being affected by the fluctuation of the patient's blood pressure and the mechanical variation in the opening/closing time of the valve.

Even if the blood pressure of the recovering patient increases, the gas pressure in the balloon is not abruptly reduced. Instead, it is gradually decreased so as not to impose a burden on the patient's heart, which is more advantageous than the technique disclosed in JP '952.

Unlike the driving apparatus of JP '952, the interior pressure of the tube line is detected at a timing of switching a state of the device to the inflated state from the deflated state in response to the switching of the valve, and the driving gas is supplied to the tube line so that the detected pressure reaches the predetermined pressure value. In JP '952, the plateau pressure is detected when the balloon (i.e., the device to be driven) is in the inflated state, and the pressure is controlled so that the detected pressure becomes constant. On the other hand, in the present invention, the pressure is detected at a time when the balloon is about to inflate from the deflated state, and the pressure is controlled so that the detected pressure is consistent with a predetermined value. In other words, the sealed tube line connected to the balloon is filled with a constant volume of gas (having a constant molecular number or constant chemical equivalent ratio), while the balloon is deflated. Based on this pressure, the gas pressure is checked as to whether it has decreased due to penetration of the gas through the balloon wall each time the balloon is deflated.

The gas pressure is regulated so that the chemical equivalent of the driving gas, which is determined according to the volumes of the balloon and the tube line (including the tubes and hoses), is consistent with the predetermined value, excluding the influence of the deformation of the balloon due to the external force. Under this situation, the plateau pressure (which is detected in the inflated state) can be observed for the purpose of checking a volume change of the balloon due to an unexpected accident, such as a bend of the balloon. For example, if the detected plateau pressure is lower than the normal pressure, it can be considered that the gas is leaking from the secondary tube line due to an accident. This situation is clearly distinguished from the natural gas penetration.

Even if the patient's blood pressure gets slightly higher than the plateau pressure in the state of inflation, the interior pressure of the balloon in the state of inflation automatically approaches the patient's blood pressure because there is no limitation on the plateau pressure and, as a result, the inflated volume of the balloon is kept constant. This feature is advantageous over the prior art teachings of JP '952.

Medical-Appliance Driving Apparatus in the Third Aspect of the Invention

In order to achieve the above-identified third object of the present invention, the medical-appliance driving apparatus, in the third aspect, comprises: a pressure generator for alternately applying a positive pressure and a negative pressure to a tube line connected to a device to be driven so that the device inflates and deflates repeatedly; a deflation time calculation means for calculating a time length of deflation of the driven device; an inflation suspending means for suspending the inflation of the device being driven for one or more continuous inflation cycles if the calculated deflation time is shorter than a predetermined value so that the deflation time recovers to the predetermined value; a pressure sensor which is capable of detecting the interior pressure of the tube line at a timing of switching a state of the device being driven to the next inflation cycle after the suspension of one or more cycles of inflation; and a gas supply system for supplying a gas into the tube line so that the pressure detected by the pressure sensor becomes a predetermined value. Instead of the deflation time calculation means, an inflation time calculation means for calculating a time length of inflation of the driven device can be used. In this case, a deflation suspending means is used in place of the inflation suspending means in order to suspend the deflation of the device being driven for one or more continuous deflation cycles if the detected deflation time is shorter than a predetermined time length. At the same time, the pressure sensor is adapted to detect the interior pressure of the tube line at a timing of switching a state of the device being driven to the next deflation cycle after the continuous inflation for the predetermined time length or longer.

In order to calculate the deflation time or the inflation time of the device being driven, the duration between switching timing of the positive pressure and the negative pressure generated by the pressure generator may be monitored. Alternatively, since the device being driven inflates and deflates in synchronization with the heart beat or the blood pressure change of the patient, the inflation or deflation time may be calculated based on the signal output from a heart-beat detection means or blood pressure detection means.

The deflation or inflation time calculation means calculates the time during which the device being driven is deflating or inflating, which is consistent with the deflation or inflation cycle of the device.

If the calculated deflation or inflation time is shorter than the predetermined value, the inflation or deflation suspending means suspends the inflation or deflation for one or more heart beats of the patient. The predetermined value used as the reference is preferably 100 milliseconds to 500 milliseconds, and more preferably, 150 milliseconds to 300 milliseconds. If the interior pressure is detected under the situation where the device is driven with insufficient deflation time or inflation time shorter than the predetermined value, a precise pressure in the stable driving state can not be obtained even if the pressure is detected at a timing of switching a state of the device from the inflation or deflation state to the deflation or inflation state. The detected pressure becomes lower than that in the stable deflated state, or higher than that in the stable inflation state.

To avoid this situation, in the present invention, the inflation or deflation of the device is suspended until the driving state of the device recovers to the stable state. The next pressure is detected at a timing of switching the driving state of the device to the next inflation or deflation cycle after the suspension. This pressure value detected in the stable state is compared with the threshold value to determine whether or not this detected gas pressure is normal. The threshold value is, for example, zero mm Hg (gauged pressure) in the deflation state, and 120 mm Hg (gauged pressure) in the inflation state. If the detected pressure is lower than the threshold value, it is regarded that there is a shortage of gas in the tube line, and the gas supply system supplies additional gas to the tube line. The method for supplying the gas is arbitrary. For example, the gas may be supplied several times in a short time, or it may supplied all at one time.

Thus, even if the device is driven at a higher rate (that is, at a shorter cycle), the inside gas pressure is detected after the driving state of the device recovers in the stable state, and an appropriate amount of gas is supplied to the tube line. This can prevent excessive amount of gas from being supplied to the balloon when the patient's heart beat rate has increased. Although, in this example, one or more cycles of inflation or deflation is suspended, it is also more preferable to keep the deflation of the device than to keep the inflation in order to reduce the load on the patient's heart. However, in practice, both methods have little influence on the patient because the suspension time or keeping time is very short. Compared with the conventional method in which the entire gas in the tube line is regularly substituted, the gas consumption is greatly reduced, and the driving apparatus becomes economical.

As a modification of this driving apparatus, a medical-appliance driving apparatus comprises: a pressure generator for alternately applying a positive pressure and a negative pressure to a tube line connected to a device to be driven so that the device inflates and deflates repeatedly; a pressure sensor for detecting the interior pressure of the tube line; a pressure change calculation means for calculating the slope (i.e., the time change rate) of the interior pressure of the tube line detected by the tube-line pressure sensor at a timing of switching a drive state to an inflated or deflated state from the deflated or inflated state, respectively; a gas supply suspending means for suspending the gas supply to the tube line, if the absolute value of the calculated slope is greater than a predetermined value; and a gas supply system for supplying the gas to the tube line, if the absolute value of the slope calculated by the pressure change calculation means is equal to or smaller than the predetermined value, so that the inside gas pressure detected at a timing of switching is kept at a predetermined value.

In order to calculate the slope of the pressure, the time derivative of the detected pressure is stored in the memory.

If the absolute value of the calculated slope is greater than the predetermined value, the gas supply suspending means suspends the gas supply operation for a predetermined number of heart beats of the patient. The greater slope implies the situation where the inflation/deflation cycle of the device is short and, accordingly, the driving state of the device, is switched from the inflation or deflation state to the deflated or inflated state, respectively, before the pressure in the tube line is stabilized. If the driving gas is supplied to the tube line based on the detected unstable pressure value, an excessive amount of gas may be supplied to the tube line.

To avoid this situation, if the absolute value of the detected slope exceeds the predetermined value, the gas supply suspending means suspends the gas supply operation until the slope becomes equal to or smaller than the predetermined value. When the slope has reached the predetermined value, the gas supply system takes in the pressure value detected by the tube-line pressure sensor at a timing of switching the driving state to the inflated or deflated state from the deflated or inflated state, respectively. Since if slope is equal to or slightly smaller than the predetermined value implies that the state in which the inflation and deflation cycle of the device is substantially normal, the detected pressure value indicates the pressure in the stable deflation state.

Based on this stable pressure value, it is determined whether or not the gas pressure is normal. If the detected pressure is lower than the threshold value (e.g., zero mm-Hg; gauged pressure), it is regarded that there is a shortage of gas in the tube line and the gas supply system supplies additional gas to the tube line. The method for supplying the gas is arbitrary. For example, the gas may be supplied several times in a short period of time, or it may supplied all at one time.

Thus, the inside gas pressure is always detected in the stable state with the slope of the pressure equal to or smaller than the predetermined value, and an appropriate amount of gas is supplied to the tube line.

One of the significant feature of this method over the conventional method is that even if the actual gas flow into and out of the balloon is slightly delayed due to the mechanical variation in the catheter or the bend of a part of the catheter, an appropriate amount of gas is still introduced into the tube line. The conventional driving apparatus is likely to introduce an excessive amount of gas in the same situation.

With the driving apparatus of the present invention, oversupply of the driving gas is prevented in the case where the patient's heart beat rate increases. Consequently, many problems arising from excessive gas supply are eliminated. Because the interior pressure of the tube line is adjusted without completely stopping the device being driven, the medical treatment of the patient is not adversely affected. As has been mentioned earlier, the total gas consumption is greatly reduced as compared with the conventional apparatus in which the entire gas in the tube line is regularly substituted.

The timing of switching, in this context, lasts for a certain time duration. The exact switching time is set to zero, but several tens of milliseconds before zero are included. Also, the response delay (generally, several milliseconds to several tens of milliseconds) of the mechanical system must be considered after the generation of the electric signal for switching the pressure. Accordingly, the actual switching time lies somewhere in the range of 50 milliseconds both before and after the generation of the electric signal.

Although there is no specific limitation to the pressure generator, it is preferable for the pressure generator to comprise a primary pressure generator for generating a positive pressure and a negative pressure alternately, and a secondary pressure generator which comprises a pressure-transfer isolator having first and second chambers. The positive and negative pressures generated by the primary pressure generator are alternately introduced into the first chamber through the primary tube line. The second chamber is isolated from the first chamber in a sealed manner, and at least a portion of the pressure in the first chamber is transferred to the second chamber.

In the driving apparatus of this invention, inflation or deflation is suspended for one or more heart beat, as is necessary, based on the detected pressure, in order to bring the gas pressure to the stable state. However, it is preferable that the number of times of the suspension of inflation or deflation is as small as possible so as not to adversely affect the patient's condition. If the suspension is often performed for the patient whose heart beat rate is high, the medical effect of using this driving apparatus decreases. Accordingly, in view of the object to compensate for the lost pressure due to the diffusion of the driving gas, it is preferable to sample the interior pressure every one to several tens of minutes, and more preferably, once every three to ten minutes. It is preferable to detect, other than this pressure sampling, the interior pressure every heart beat in order to check abrupt pressure change.

During the three to ten minutes time interval, the heart beat rate may fluctuate, and the inflation or deflation cycle may become of long duration of times. Accordingly, it is preferable to use the pressure value detected immediately after such a long inflation or deflation time (at which the slope of the pressure becomes gentle) in order to check the necessity of additional gas supply.

The functions of the driving apparatuses described in the first through third aspects may be combined with one another.

If the deflation or inflation time, or the absolute value of the slope of the pressure does not satisfy the given condition, any one of the deflation time, the inflation time, or the slope may be monitored for a certain time (e.g., for a predetermined number of heart beats) prior to suspending inflation or deflation. If any one of the inflation time, the deflation time, or the slope satisfies the given condition at least once during the time being monitored, then the pressure detected in that time can be used, and the gas supply system supplies the driving gas to the tube line so that the detected pressure reaches the predetermined value.

The functions of the driving apparatus described above may be performed throughout driving operation of the driving apparatus or, as an alternative, some of the functions may be activated only for a given period of time.

The tube line is not limited to flexible tubes or hoses, but includes non-flexible tubes. The term "tube line" includes tanks and other devices connected to this tube line.

Pressure-Transfer Isolator

When driving the device using the conventional pressure-transfer isolator, a small peak appears in the flat portion of the pressure waveform in each pulse. The inventors found that the appearance of this small peak is related with the structure of the inner surface of the casing of the pressure-transfer isolator. The inventors also found that this small peak is caused by residual fluid residing between the inner surfaces of the casing and the flexible membrane (such as a diaphragm). The membrane oscillates between the two opposed inner faces of the casing in synchronization with the patient's heart beat. The fluid remains between the membrane and the inner surface during contact with each other until the membrane leaves the contact surface immediately before the pressure is switched. The residual liquid flows into the first or second port when the pressure is switched. This causes small peaks in the pressure pulses.

In order to achieve the above-described fourth object of the present invention, a pressure-transfer isolator is provided, which can transfer a pressure change of a primary tube line, and which is connected to a pressure generator for generating a positive pressure and a negative pressure to a secondary tube line, and which is connected to a device to be driven without allowing gas flow between the primary tube line and the secondary tube line. This pressure-transfer isolator comprises: a first casing having a first inner surface and a first port that is connectable to the primary tube line; a second casing having a second inner surface and a second port that is connectable to the secondary tube line; a flexible membrane provided in a space formed by the first and second casings so as to partition the space into a first chamber that is connected to the first port and a second chamber that is connected to the second part, wherein the flexible membrane oscillates between the first and second inner surfaces due to a pressure change arising in the first chamber; and a relief passage for driving residual fluid residing on the first and second inner surfaces away into the first and second ports, respectively, when the flexible membrane contact the each one of the surfaces.

The relief passage is, for example, a groove formed in the first inner surface and/or the second inner surface, such that the groove extends in the radial direction and centers on the first port and/or the second port.

Alternatively, the relief passage is a rib formed in the first inner surface and/or the second inner surface, such that the rib extends in the radial direction and centers on the first port and/or the second port.

The groove or the rib may be formed so as to extend either continuously or discontinuously in the radial direction.

The relief passage may be a hole formed on the side wall of a nozzle, provided on the first port or the second port, and projecting into the first chamber or the second chamber.

The relief passage may be formed on at least one surface of the flexible membrane. In this case, a groove or a rib is formed on the membrane surface so as to extend either continuously or discontinuously in the radial direction.

This relief passage efficiently outlets to the first and second ports, respectively, residual fluid residing between the first or second inner surface of the casings and the membrane surfaces which alternately contact the first and second inner surfaces. This arrangement can leave no residual fluid between the inner surface and the membrane so that no residual fluid flows into the tube line immediately before the pressure is switched, which can further prevent small fluctuations (that is, small peaks) appearing in the flat portions of the pressure pulses.

Thus, the pressure is detected at the momentarily stabilized portion in the pressure pulse without being affected by small peaks, and based on this detected pressure, the operation state of the driving apparatus is accurately controlled.

Monitor for Medical-Appliance Driving Apparatus

A monitor is provided to the medical-appliance driving apparatus in order to check if the patient's body fluid is mixed in the tube line of the driving apparatus. The monitor has a body fluid sensor, which is placed in the middle of the tube line, through which a driving fluid, for driving the medical-appliance driving apparatus, flows.

The body fluid sensor comprises a light-emitting device for emitting light toward the driving fluid flowing through the tube line, and a light-receiving device for receiving the light that was emitted from the light-emitting device and has passed through the driving fluid. If there is no body fluid mixed in the driving fluid flowing through the tube line, the detection result of the light-receiving device is increased to a high level, while if body fluid is mixed in the driving fluid, the detection result is decreased to a low level. The light-emitting device is, for example, a light-emitting diode (LED) for emitting blue or green light with or without a filter, or a laser diode. The light-receiving device is, for example, a photosensor diode or a CCD. The light-emitting device and the light-receiving device are positioned on both sides of the tube line so as to be perpendicular to the longitudinal axis of the tube line and to face each other at an angle of 180.

The body fluid sensor may comprise a light-emitting device for emitting light toward the driving fluid flowing through the tube line, and a light-receiving device for receiving the light that was emitted from the light-emitting device and was diffused from the driving fluid. In this case, if there is no body fluid mixed in the driving fluid flowing through the tube line, the detection result of the light-receiving device is decreased to a low level, while if body fluid is mixed in the driving fluid, then the detection result is increased to a high level.

The light-emitting device is, for example, a light-emitting diode (LED) for emitting red or yellow light with or without a filter, or a laser diode. The light-receiving device is, for example, a photosensor diode or a COD. The light-emitting device and the light-receiving device are positioned so as to be perpendicular to the longitudinal axis of the tube line and to make an angle of 90 with respect to each other.

Although, in this example, an optical type sensor is used to detect the patient's body fluid (e.g., blood) mixed into the tube line, a chemical sensor capable of chemically detecting the patient's body fluid can also be used. In general, chemical sensors are less expensive and more convenient than optical sensors.

During the use of the driving apparatus, a pin hole may be formed in the medical device that is placed in the patient's body and driven by the driving apparatus, or some other breakage may occur in that device. In this case, the monitor, according to the invention, directly detects if the patient's body fluid is mixed into the tube, rather than monitoring the pressure change of the driving fluid. For example, if a pin hole is formed in the balloon, the patient's body fluid (e.g., blood), the volume of which corresponds to that of the gas leaking from the pin hole, is mixed into the tube line. Since this body fluid is detected directly by the sensor, the pin hole or other defects can be found earlier.

Because it is difficult to distinguish abnormal gas leakage caused by a small pin hole from the natural diffusion of the gas through the wall of the medical device only from the change in the gas pressure, abnormal gas leakage is likely to be unrecognized. The body fluid mixed in the tube line may clot in the tube line, which may be fatal to the patient and must be avoided. Especially, the case in which the patient's blood is accumulated inside the tube line little by little over a long time makes the situation worse.

In view of these problems, the sensor of the present invention directly detects the body fluid mixed in the tube line so that pin holes or other defects in the device being driven can be found earlier, thereby preventing blood clots in the tube line in advance.

BRIEF DESCRIPTION OF THE DRAWINGS

The present invention will be described in more detail based on the preferred embodiments with reference to the attached drawings, wherein:

FIG. 4A is a graph showing the interior pressure of each tank;

FIG. 4B shows a pressure change in the balloon;

FIG. 4C shows a volume change of the balloon;

FIGS. 5A through 5D are timing charts indicating points of time where pressures are measured;

FIG. 7 is a cross-sectional view of the balloon catheter;

FIG. 18A is a cross-sectional view of the casing used in the pressure-transfer isolator according to another embodiment;

FIG. 18B is a front view of the inside of the casing;

FIG. 19A is a cross-sectional view of the casing used in the pressure-transfer isolator according to still another embodiment;

FIG. 19B is a front view of the inside of the casing;

THE PREFERRED EMBODIMENT OF THE INVENTION

The preferred embodiments of the present invention will now be described with reference to the attached drawings.

First Embodiment

Figure 1:
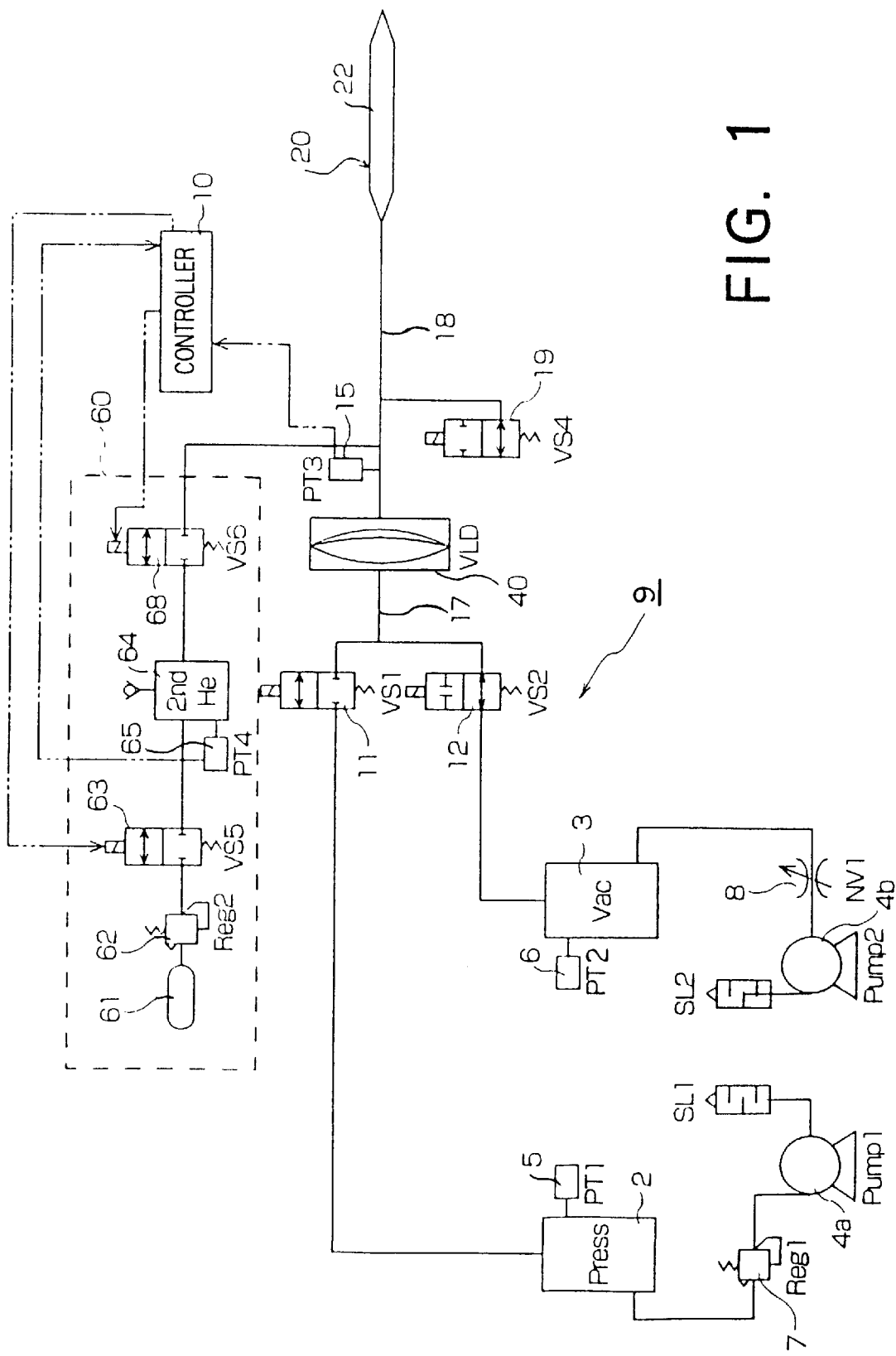
FIG. 1 is a schematic diagram of the medical-appliance driving apparatus according to an embodiment of the present invention.

The driving apparatus shown in FIG. 1 is used to inflate and deflate the balloon 22 of the IABP balloon catheter 20.

Prior to describing the medical-appliance driving apparatus of this embodiment, explanation will be made on the IABP balloon catheter 20.

FIG. 7 illustrates the IABP balloon catheter 20 in a cross-sectional view. The balloon 22 is formed of a cylindrical balloon film having a thickness of about 100 $\mu$m to 150 $\mu$m, and is inflated and deflated in agreement with the heat beat of the patient. In this embodiment, the balloon is cylindrical when it is inflated. However, it may have the shape of a polygonal column.

The balloon 22 is made of an anti-fatigue material having a superior bend-resistance. The outer diameter and the length of the balloon 22 are determined according to the volume of the balloon 22, which greatly influences the medical effect to the heart function, and the inner diameter of the artery. In general, the volume of the balloon 22 is 30 cc to 50 cc, the inflated outer diameter is 14 mm to 16 mm, and the length is 210 mm to 270 mm.

The distal end of the inner tube 30 extends from the distal end of the catheter tube 24 penetrating through the catheter 24 and the balloon 22 along the axial direction. The near end of the inner tube 30 is connected to the second port 32 of the bifurcation 26. A second lumen is formed inside the inner tube 30. The second lumen does not communicate with the first lumen formed inside the catheter tube 24 and the balloon 22. The inner tube 30 receives the blood pressure at the opening 23 of the distal end, and supplies the blood pressure to the second port 32 of the bifurcation 26, through which the change in the blood pressure is measured.

When the balloon catheter 20 is inserted into the artery, the second lumen formed in the inner tube 30 functions as a guide wire introducing lumen for appropriately introducing the balloon 22 into the artery. When inserting the balloon catheter 20 into a cavity (e.g., a blood vessel), the balloon 22 is originally folded around the outer face of the inner tube 30. The inner tube 40 shown in FIG. 4 is formed of the same material as the catheter tube 24. The inner diameter of the inner tube 30 is not limited to a specific size as long as the guide wire can penetrate through it. For example, it is set to 0.15 mm to 1.5 mm, and the more preferable range is from 0.5 mm to 1.0 mm. Preferably, the thickness of the inner tube 30 is 0.1 mm to 0.4 mm. The length of the inner tube 30 is determined according to the length of the balloon catheter 20 which is to be inserted into the blood vessel, and it is generally set to 500 mm to 1200 mm, and more preferably to 700 mm to 1000 mm.

The catheter tube 24 is preferably made of a flexible material. Preferably, the inner diameter of the catheter tube 24 is 1.5 mm to 4.0 mm, and the thickness of the catheter tube 24 is 0.05 mm to 0.4 mm. The length of the catheter tube 24 is 300 mm to 800 mm.

The near end of the catheter 24 is connected to the bifurcation 26 which is set outside the patient's body. The bifurcation 26 is formed separately from the catheter tube 24, and is connected to the catheter tube by thermal fusion or mechanical adhesion. A first port 28 for introducing and outletting the pressure fluid in and from the first lumen of the catheter tube 24 and the balloon 22, and a second port 32 connected to the second lumen of the inner tube 30 are formed in the bifurcation 26.

The first port 28 is connected to the pump 9 which has a structure, for example, shown in FIG. 5. The pump 9 supplies the fluid pressure into the balloon 22, and draws the fluid out of the balloon 22. Many types of fluid can be used to drive the balloon 22, but helium gas, which has a small viscosity and a small mass, is preferably used because it allows the balloon 22 to inflate and deflate very quickly in response to the driving cycle of the pump 9.

The detailed structure of the pump 9 will be described later with reference to FIG. 1.

Figure 8:
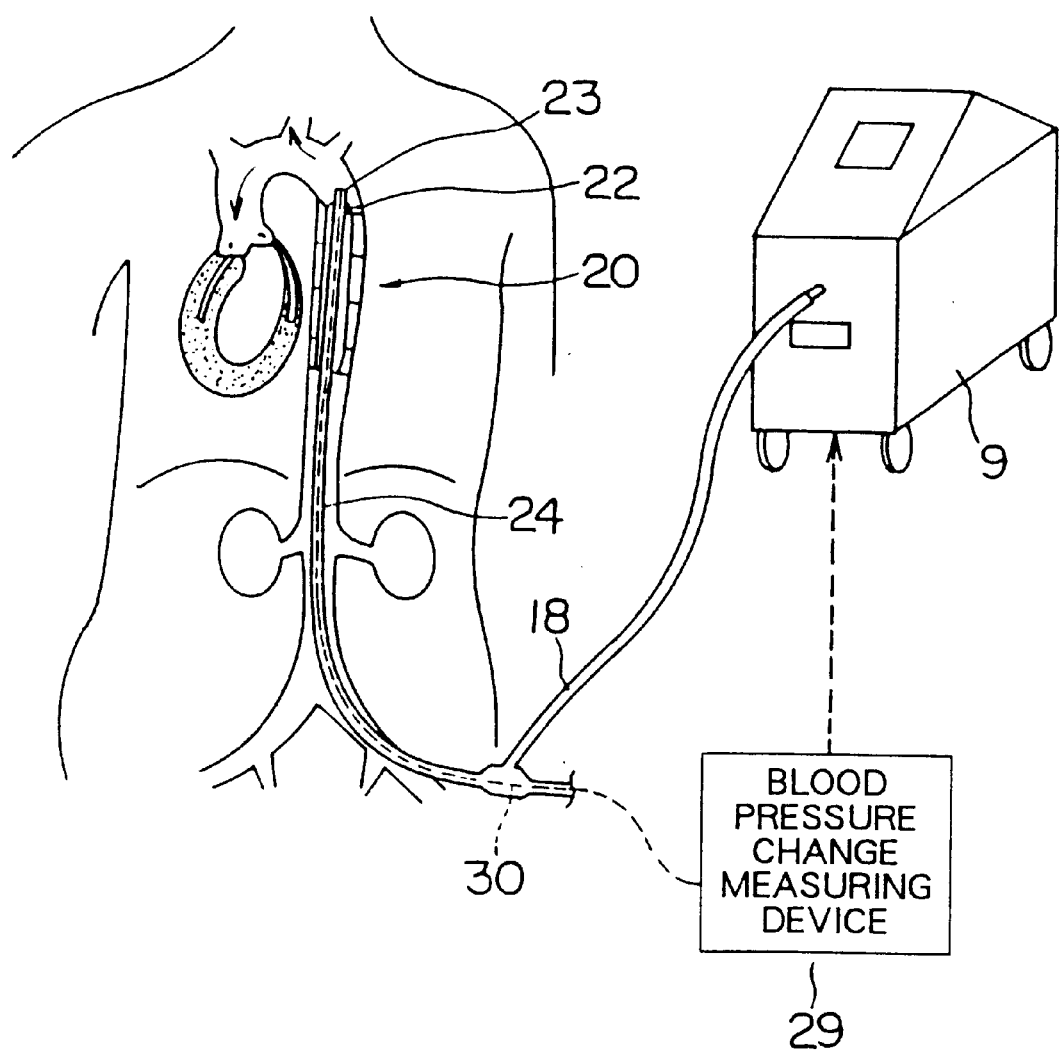
FIG. 8 illustrates how the balloon catheter is used in an actual treatment.

The second port 32 is connected to the blood-pressure measuring apparatus 29 shown in FIG. 8, whereby the blood pressure in the artery, received at the aperture 23 of the distal end of the balloon 22, is supplied to the blood-pressure measuring apparatus 29. Based on the blood pressure detected by the measuring apparatus 29, the pump 9 is controlled in synchronization with the heat beat of the patient so as to inflate and deflate the balloon 22 in a short cycle of approximately 0.4 second to 1 second.

Figure 2:
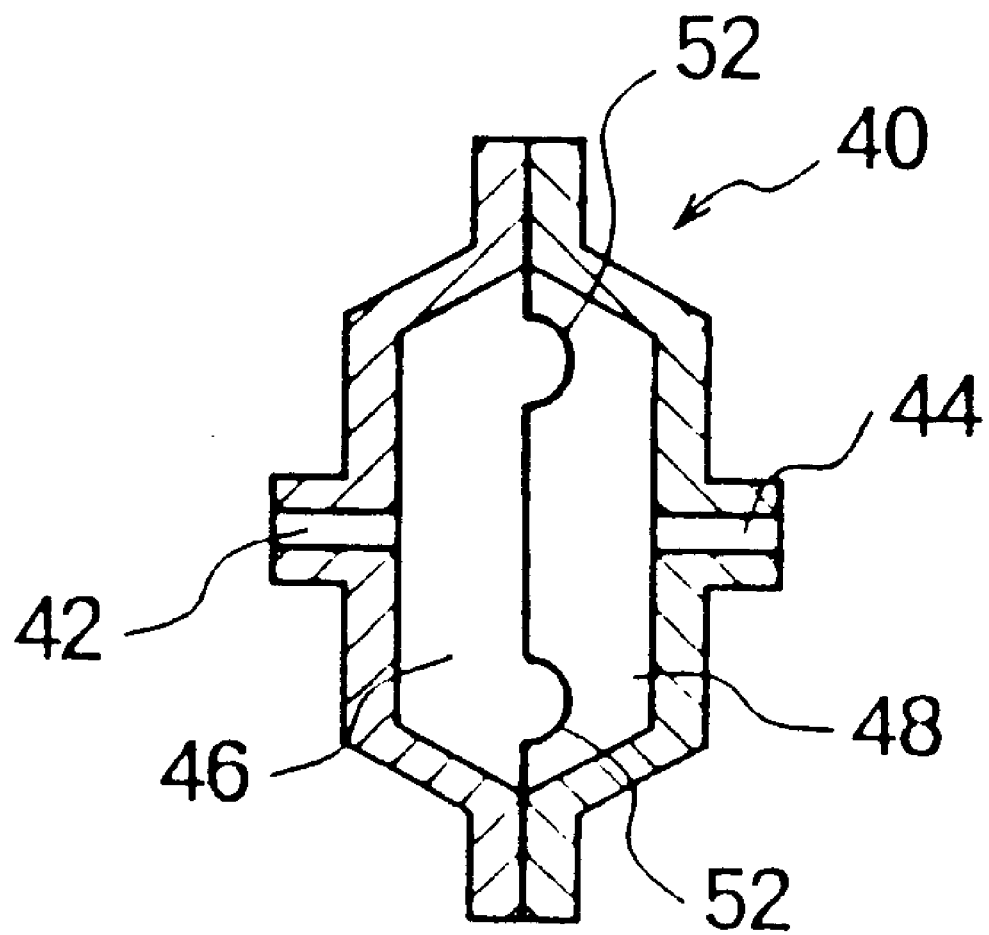
FIG. 2 is a cross-sectional view of an example of a pressure-transfer isolator.

In the IABP balloon catheter 20, helium gas is preferably used as the fluid for driving the balloon 22 because of its small mass and high response. Producing positive and negative pressures in the helium gas directly by the pump or a compressor is not economical because a portion of the generated pressure may be lost due to, for example, leakage from the sealed area. In order to avoid waste, the driving apparatus of the present invention employs the structure shown in FIG. 1, in which the secondary tube line 18 connected to the balloon 22 is isolated from the primary tube line 17 connected to the pumps 4a and 4b (which function as the primary pressure generators) by the pressure-transfer isolator 40. An example of pressure-transfer isolator 40 is shown in FIG. 2. This pressure-transfer isolator 40 has a first chamber 46 and a second chamber 48, which are partitioned by a diaphragm 52 in an airtight manner.

The first chamber 46 is connected to the primary tube line 17 via the port 42, while the second chamber 48 is connected to the secondary tube line 18 via the port 44. Although the fluid flow is shut off between the first chamber 46 and the second chamber 48, a pressure change (or a volume change) in the first chamber 46 is transferred to the second chamber 48 via the displacement of the diaphragm 52, and that pressure change appears in the second chamber 48 as a pressure change or a volume change in the second chamber 48. This arrangement allows any pressure changes in the primary tube line 17 to be transferred to the secondary tube line 18 without connecting these two tube lines. This arrangement can make it easy to keep the volume (i.e., the chemical equivalent) of the gas enclosed in the secondary tube line 18 constant.

In this embodiment, the primary tube line 17 is filled with air, while the secondary tube line 18 is filled with helium gas because helium gas has a small mass which can improve the inflation/deflation response of the balloon 22.

As shown in FIG. 1, pumps (i.e., pressure generators) 4a and 4b are provided in the primary tube line 17. The first pump 4a, which generates positive pressure, can be called a compressor. The second pump 4b generates a negative pressure. The positive output port of the first pump 4a is connected to the first pressure tank (or the positive pressure tank) 2 via a regulator value 7, and the negative output port of the second pump 4b is connected to the second pressure tank (or the negative pressure tank) 3 via a throttle valve 8.

The first and second pressure tanks 2 and 3 are furnished with pressure sensors 5 and 6, respectively, for detecting the interior pressures. The first and second pressure tanks 2 and 3 are also connected to the input ports of the first and second solenoid valves 11 and 12, respectively. The opening/closing operations of the solenoid valves 11 and 12 are controlled by a controller (not shown) so as to be consistent with the patient's heart beat. The output ports of the solenoid valves 11 and 12 are connected to the input port 42 (FIG. 2) of the pressure-transfer isolator 40 which functions as a secondary pressure generator.

The output port 44 of the pressure-transfer isolator 40 shown in FIG. 2 is connected to the secondary tube line 18 shown in FIG. 7. The secondary tube line 18 is a sealed line filled with helium gas, and it is connected to the balloon 22. A pressure sensor 15 is provided to the secondary tube line 18 in order to detect the interior pressure of this line. The output of the pressure sensor 15 is supplied to the controller 10.

An exhaust pump (not shown) is also connected to the secondary tube line 18 via an solenoid valve. The exhaust pump and the solenoid valve are provided to evacuate the secondary tube line 18 in order to substitute the helium gas for the air prior to using the balloon catheter. Once the gas substitution is completed, this solenoid valve is closed, and the exhaust pump is not driven during the actual use of the balloon catheter.

An solenoid valve 19 is provided to the secondary tube line 18. If the interior pressure of the secondary tube line 18 exceeds a predetermined value, the solenoid valve 19 is opened for a predetermined time under the control of the controller 10, thereby discharging a portion of the gas.

A gas supply system 60 is connected to the secondary tube line 18. The gas supply system 60 supplies a predetermined amount of helium gas to the secondary tube line 18 so that the chemical equivalent of the inside gas is always kept constant. The gas supply system 60 has a primary helium gas tank 61. The output port of the helium gas tank 61 is connected to the first solenoid valve 63 via a regulator valve 62. The switching operation of the first solenoid valve 63 is controlled by the controller 10. The output port of the first solenoid valve 63 is connected to the secondary helium gas tank 64. Thus, a gas flow can be allowed between the secondary helium gas tank 64 and the primary helium gas tank 61 when the solenoid valve 63 is open.

A pressure sensor 65 is provided to the secondary helium gas tank 64. Based on the pressure detected by the pressure sensor 65, the interior pressure of the tank 64 is kept constant under the control of the controller 10. The interior pressure of the tank 64 is set to, for example, 100 mm Hg or less. The pressure detected by the sensor 65 is supplied to the controller 10.

A second solenoid valve 68, which is controlled by the controller 10, is connected to the secondary helium gas tank 64. An initial fill-up solenoid valve (not shown) is also connected to the helium gas tank 64 in parallel with the second solenoid valve 68. The initial fill-up valve is used only when the helium gas is first supplied into the secondary tube line 18 which has been evacuated, and it is not used in the regular operation.

In operation, the interior pressure PT1 of the first pressure tank 2 is set to about 300 mm Hg (gauged pressure) by driving the pump 4a, and the interior pressure PT2 of the second pressure tank 3 is set to about −150 mm Hg (gauged pressure) by driving the pump 4b. The pressure applied to the input port of the pressure-transfer isolator 40 (FIG. 1) is alternately switched between the first and second pressure tanks 2 and 3, respectively, by alternately driving the solenoid valves 11 and 12. The switching timing between the solenoid valves 11 and 12 is controlled by the controller 10 so as to be synchronized with the patient's heart beat.

FIG. 4A shows the fluctuation of the pressures PT1 and PT2 detected by the sensors 5 and 6, and FIG. 4B shows the pressure PT3 in the secondary tube line 18, which is detected by the pressure sensor 15. The peak pressure of the secondary tube line 18 is 289 mm Hg (gauged pressure), and the minimum is −114 mm Hg (gauged pressure). The pressure change in the secondary tube line 18 causes the volume of the balloon 22 to change, as shown in FIG. 4C. In this manner, the balloon 22 inflates and deflates in synchronization with the patient's heart beat, thereby aiding or activating the heart function of the patient.

Figure 3:
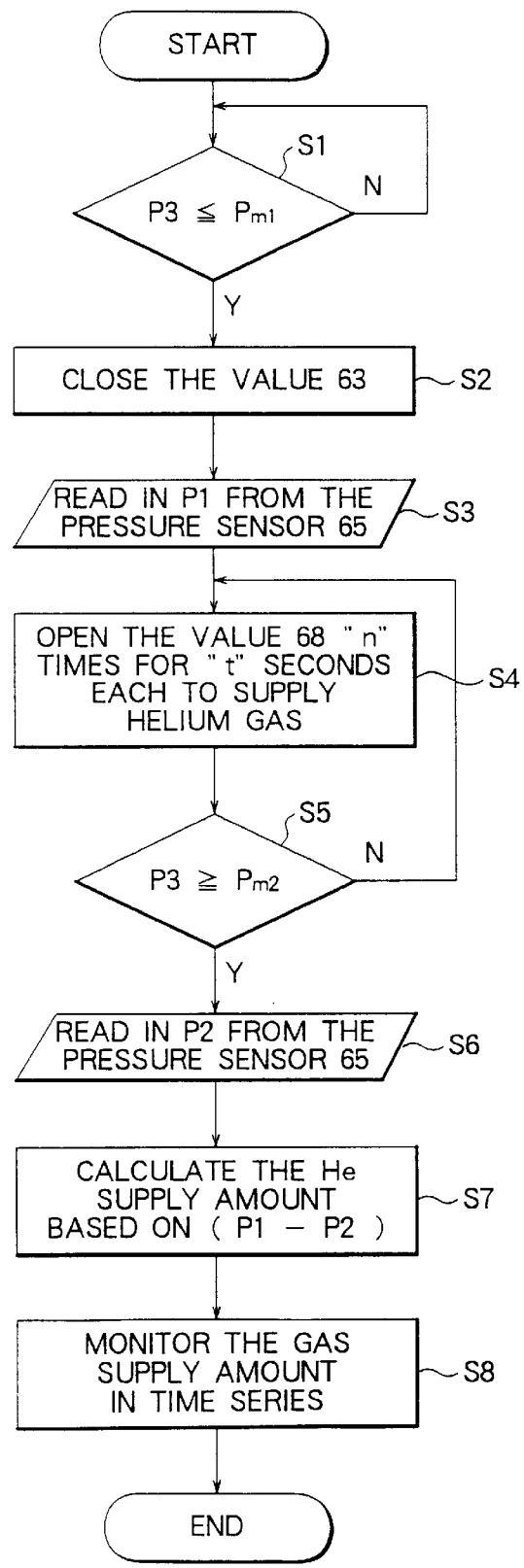
FIG. 3 is a flowchart showing the control operation of the medical-appliance driving apparatus of the present invention.

The operation of the controller 10 will now be explained with reference to FIG. 3.

In step S1, the interior pressures of the secondary tube line 18 detected by the pressure sensor 15 is taken in at a timing indicated by "*2" in FIG. 5D (at a timing of switching a drive state of balloon to an inflated state from a deflated state, that is, at a time when the balloon is about to inflate from the deflated state shown in FIG. 5B), and it is determined if the sampled pressure P3 is equal to or less than the prescribed value Pm1, for example, zero mm Hg. If the determination result is NO, this means that the interior pressure of the secondary tube line 18 is adequate and, accordingly, step S1 is simply repeated. If the sample pressure is equal to or less than Pm1, that means that there is a shortage of helium gas inside the secondary tube line 18. In this case, the process proceeds to step S2 and after, to supply additional helium gas into the secondary tube line 18.

In this embodiment, pressure P3 taken in the deflated state of the balloon is used to check the interior pressure of the secondary tube line 18, rather than using the plateau pressure P4 taken in at a time indicated by "*1" in FIG. 5C (i.e., at a time when the baboon is in the stable inflation state), for the purpose of distinguishing natural gas leakage from abnormal gas leakage.

If the plateau pressure P4 of the balloon side tube line, which is taken in at a time indicated by "*1" in FIG. 5C, is used to determine the necessity of additional gas supply, the helium gas (i.e., the driving gas) is continuously supplied to the balloon-side tube line even if the volume of the balloon has changed due to an accident. Accidents include, for example, the fatigue of the balloon, inappropriate pressure application, bending of the blood vessel of the patient, and other unexpected occurrences (for example, the balloon has stuck in a swelling inside the blood vessel). The life of the distorted balloon becomes shorter, which is undesirable for the patient. In addition, if the interior pressure of the balloon exceeds the predetermined upper limit as the patient's blood pressure increases in his recovery process, the gas supply operation may be controlled erroneously and the helium gas may be removed by mistake from the balloon in the worst case. In such a case, the balloon will not be adequately inflated.

To avoid this situation, in this embodiment, a constant amount of gas (with a constant molecular number or constant chemical equivalent ratio) is supplied to the sealed tube line 18 connected to the balloon 22, when the balloon 22 is in the deflated state. Then, natural gas leakage, penetrating through the balloon 22, is monitored based on the pressure of the tube line, while the balloon is in the deflated state.

This arrangement can exclude the influence of the gas pressure on the balloon 22 which may be deformed by an external force, and it can control the pressure so that the chemical equivalent of the driving gas, which is determined according to the volumes of the balloon and the tube line (including the tubes and hoses), is consistent with the predetermined value. Under this situation, the plateau pressure P4 (which is detected in the inflation state) can be observed for the purpose of checking a volume change of the balloon 22 due to some unexpected accidents, including bending of the balloon 22. For example, if the detected plateau pressure P4 is higher than the normal pressure, it can be considered that the balloon 22 is bending. If the plateau pressure P4 is smaller than the normal pressure, it can be considered that gas is leaking from the secondary tube line due to an accident. These two situations are clearly distinguished from each other.

In this embodiment, if the patient's blood pressure becomes higher than the plateau pressure P4, the volume of the balloon 22 is kept substantially constant, and the plateau pressure P4 varies in agreement with the blood pressure.

If, in step S1, it is determined that the pressure P3 is equal to or less than Pm1, and that it is necessary to supply the driving gas, then the process proceeds to step S2, in which the first solenoid valve 63 (FIG. 1) is closed. Upon the closing of the solenoid valve 63, the primary helium gas tank 61 is disconnected from the secondary helium gas tank 64. Then, in step S3, pressure P1, detected by the tank-pressure sensor 65 (FIG. 1), is taken in. In step S4, the second solenoid valve 68 is opened "n" times for "t" milliseconds each in order to supply the helium gas from the helium gas tank 64 to the secondary tube line 18, wherein "t" milliseconds is, for example, 8 milliseconds and "n" times is, for example, 1 to 10 times.

In step S5, pressure P3, detected by the pressure sensor 15, is again taken in at a timing indicated by "*2" in FIG. 5D, and it is determined if P3 is greater than or equal to Pm2. Pm2 is the predetermined upper limit, and it is, for example, 10 mm Hg. Step S4 is repeated as long as the detected pressure P3 is smaller than Pm2 so that additional helium gas is supplied to the secondary tube line 18.

If, in step S5, it is determined that the detected pressure P3 reaches or exceeds Pm2, an adequate amount of helium gas was supplied to the secondary tube line, and the gas supply is stopped. Then, in step S6, pressure P2, detected by the pressure sensor 65, is read in. The pressure P1, previously detected by the tank sensor 65, is the interior pressure of the secondary helium gas tank 64 before the gas is supplied to the secondary tube line 18, while the pressure P2 taken in step S5 represents the interior pressure of the secondary helium gas tank 64 after the gas is supplied to the secondary tube line 18. At this time, the primary helium gas tank 61 is disconnected from the secondary helium gas tank 64 by the solenoid valve 53. Therefore, the amount of gas supplied from the secondary gas tank 64 to the secondary tube line 18 can be calculated from the pressure difference (P1−P2) and the volume V of the secondary helium gas tank 64 based on the pressure difference times the volume (P1−P2)*V.

Next, in step S8, the calculated gas supply amount is stored in a recording medium in time series. The recording medium includes, but is not limited to, semiconductor memories, magnetic discs, optical recording medium, and other recording media. The stored data is output on the monitor screen or papers, as necessary. By observing the recorded data, it can be determined that abnormal gas leakage has occurred, when the time interval of gas supply becomes shorter and when the calculated amount of supplied gas started increasing, whereby an alarm can be given earlier. The CPU reads out the gas supply data stored in the recording medium in time series, and an alarm can be automatically given if the CPU has determined from the data that an abnormal gas leakage has occurred.

Figure 6A:
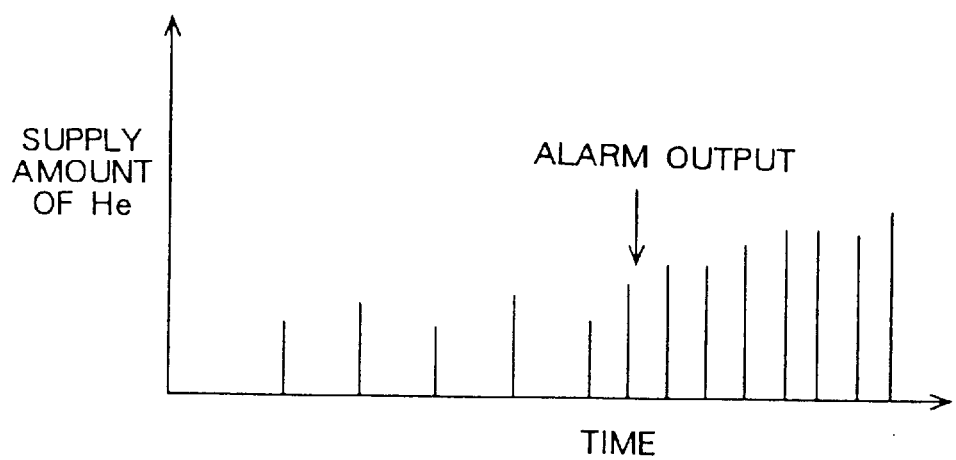
FIG. 6A is a graph of the amount of helium gas supplied at the appropriate timing wherein the amount of supplied helium gas changes as time passes.
Figure 6B:
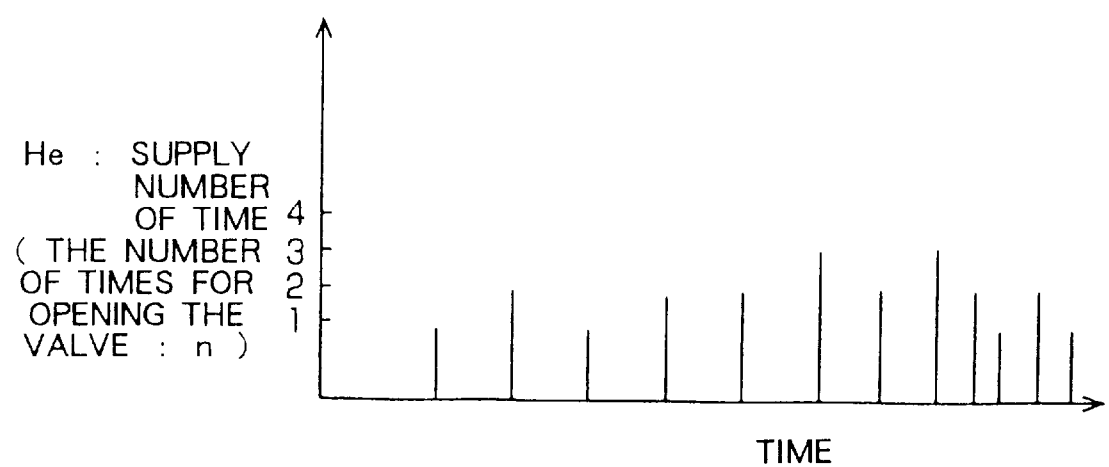
FIG. 6B is a graph of the number of times the valve is opened to supply the helium gas at one time wherein the number of valve openings changes as time passes.

The conventional driving apparatus does not have the solenoid valve 63 shown in FIG. 1, and the switching operation of only the solenoid valve 68 is controlled. Accordingly, even if the relationship between the number of switching operations of the solenoid valve 68 and the time is graphed as shown in FIG. 6B, the number of switching operations does not accurately represent the amount of helium gas supplied to the secondary tube line 18. For this reason, it is difficult for the conventional apparatus to distinguish abnormal gas leakage from natural gas leakage in the normal operation by observing the time interval between gas supply operations (i.e., valve switching operations).

It should be understood that the present invention is not limited to this specific embodiment, and that many changes can be made within the scope of the invention.

For example, two pumps 4a and 4b are used in this embodiment as the primary pressure generators. However, a single pump may be used as the primary pressure generator. In this case, a first pressure tank 2 is connected to the positive-pressure output port of the single pump, and a second pressure tank 3 is connected to the negative-pressure output port of the pump. The number of pumps and, therefore, the weight of the entire apparatus, as well as the energy consumption, can be reduced. The pump is not limited to the diaphragm pump, but many other pumps, such as a linear piston pump, a rotary vane pump, a piston pump, a compressor, or similar, can be used.

Although, in this embodiment, two solenoid valves (i.e., the third and fourth valves) 11 and 12 are used as the pressure switching means, a three-way valve may be used to switch the pressure applied to the input port of the pressure-transfer isolator 40.

The gas flowing through the primary tube line 17 is not limited to air, and another fluid may be used in place of air. Similarly, the gas flowing through the secondary tube line 18 is not limited to helium gas.

Figure 9:
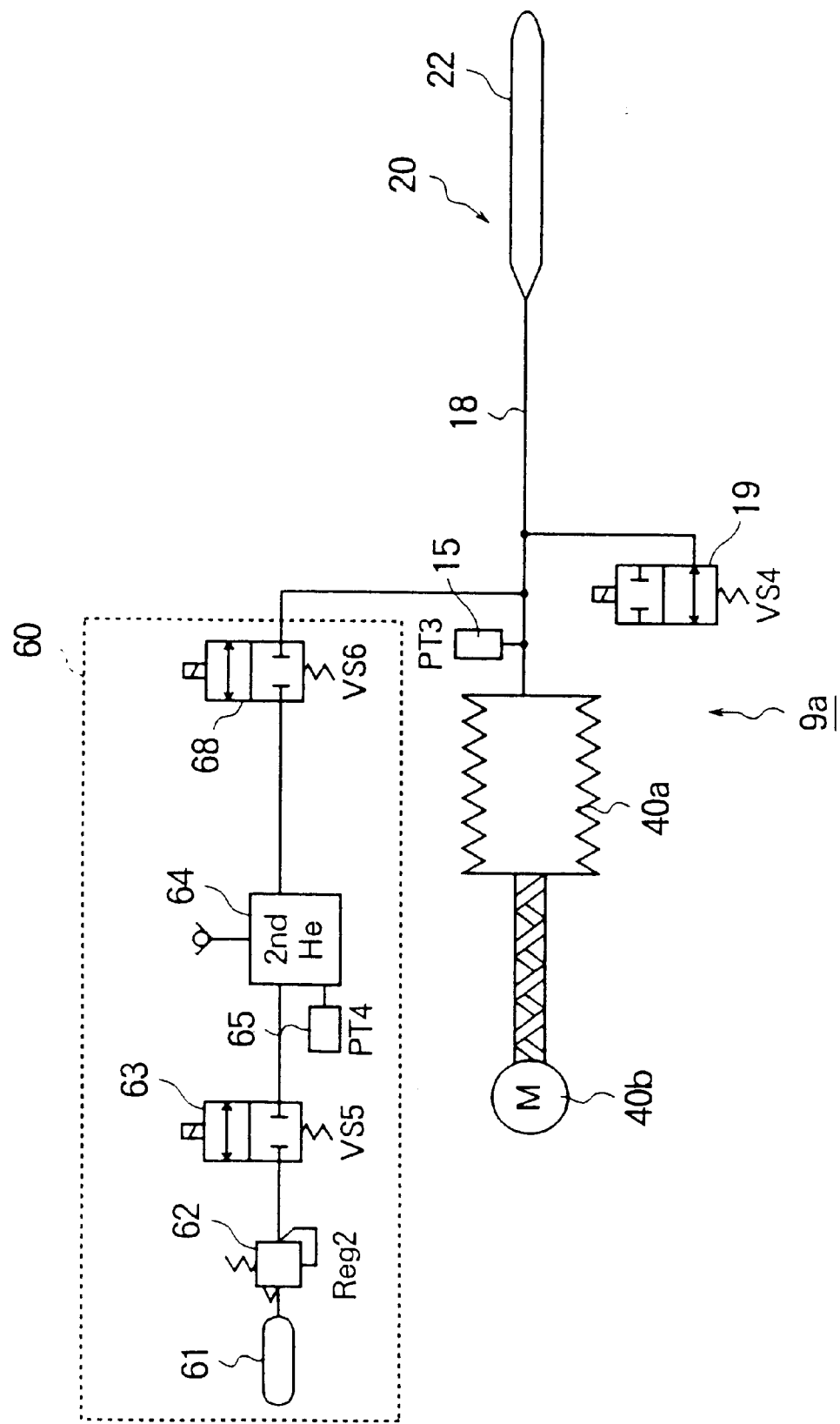
FIG. 9 is a schematic diagram of the medical-appliance driving apparatus according to another embodiment of the present invention.

A modified driving apparatus 9a is shown in FIG. 9, in which a pressure generator that reciprocates the driving gas is connected directly to the secondary tube line 18, without using the primary tube line 17 and the pressure-transfer isolator 40. Such a pressure generator comprises, for example, bellows 40a, and a driving means (e.g., a motor 40b) for expanding and compressing the bellows in the axial direction. The secondary tube line 18 is connected directly or indirectly to the inside or the outside of the bellows 40a. By driving the bellows 40 in the axial direction using the motor, the gas is supplied and removed directly to and from the secondary tube line 18, thereby inflating and deflating the balloon 22. The other structure of the driving apparatus 9a is the same as those described above in this embodiment.

Although a balloon catheter is driven by the driving apparatus in this embodiment, this driving apparatus can be used to drive any medical appliances that repeats inflation and deflation.

Second Embodiment

Figure 10:
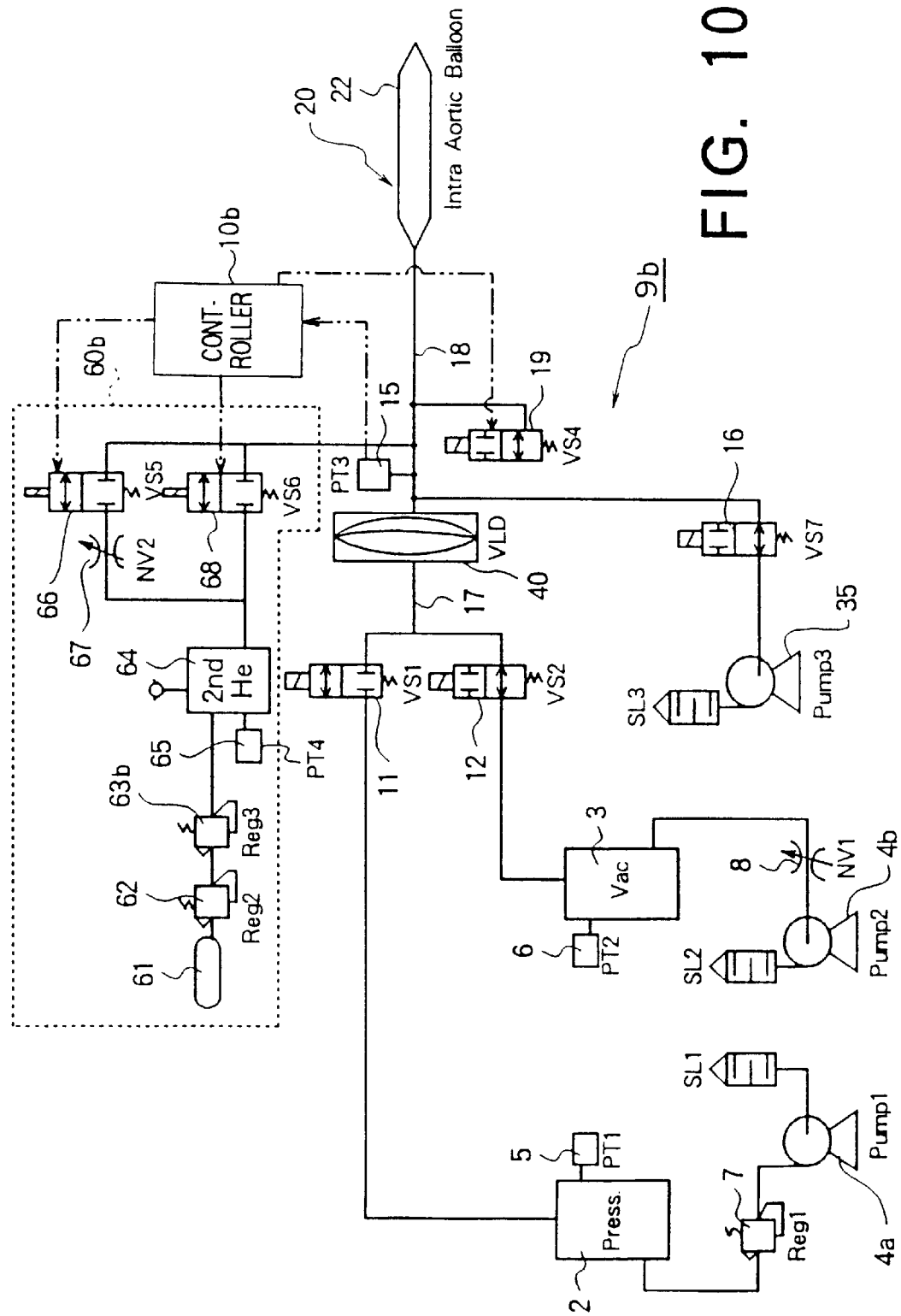
FIG. 10 is a schematic diagram of the medical-appliance driving apparatus according to still another embodiment of the present invention.

FIG. 10 illustrates the driving apparatus 9b according to the second embodiment. This driving apparatus is a modification of the driving apparatus 9 of the first embodiment, and the same elements as those in the first embodiment are denoted by the same numerical symbols.

The gas supply system 60b of this embodiment has a primary helium gas tank 61, which is connected to a secondary helium gas tank 64 via regulator valves 62 and 63b. A pressure sensor 65 is provided to the secondary helium gas tank 64. The pressure sensor 65 monitors the interior pressure of the tank 64 so that the interior pressure of the tank 64 is kept constant, for example, at 100 mm Hg or less.

A fill-up solenoid valve 66 and an initial charging solenoid valve 68 are connected in parallel and to the secondary helium tank 64 via a throttle valve 67. These solenoid valves 66 and 68 are controlled by the controller 10b. The initial charging solenoid valve 68 is used to initially charge the evacuated secondary tube line 18 with helium gas, and it opens in association with the pump 35 and the solenoid valve 16. The solenoid valve 68 is not activated in the normal driving operation.

The secondary tube line 18 is evacuated until the interior pressure reaches a predetermined negative pressure. Then, helium gas is supplied to the secondary tube line 18, while the pressure sensor 15 monitors the interior pressure of the secondary tube line 18, until the interior pressure reaches the prescribed pressure determined by the volume of the balloon 22. For example, if the volume of the balloon 22 is 40 cc, the fill-up pressure is set to 10±5 mm Hg (gauged pressure). If a balloon catheter with a volume of 30 cc is used, then the gas pressure is set to −80±5 mm Hg (gauged pressure).

In regular operation of the driving apparatus 9b, the pump 4a is driven to bring the pressure PT1 of the first pressure tank 2 to about 300 mm Hg (gauged pressure), and the pump 5b is driven to bring the pressure PT2 of the second pressure tank 3 to about −150 mm Hg (gauged pressure). The pressure applied to the input port of the pressure-transfer isolator 40, shown in FIG. 10, is switched between PT1 and PT2 of the first and second pressure tanks 2 and 3, respectively, by alternately driving the solenoid valves 11 and 12. The switching timing is controlled by the controller in synchronization with the patient's heart beat.

The pressures PT1 and PT2 detected by the pressure sensors 5 and 6, respectively, are almost the same as those shown in FIG. 4A in the first embodiment. The pressure PT3 of the secondary tube line 18 (FIG. 10) detected by the pressure sensor 15 is also the same as that shown in FIG. 4B. The peak pressure of the secondary tube line 18 is 289 mm HG (gauged pressure) in this example, and the minimum is −114 mm Hg (gauged pressure). The pressure change in the secondary tube line 18 causes the volume of the balloon 22 to change, as shown in FIG. 4C. In this manner, the balloon 22 inflates and deflates consistent with the patient's heart beat, thereby aiding or activating the heart function of the patient.

The pressures PT3 of the secondary tube line 18 detected by the pressure sensor 15 is taken in at a timing indicated by "*2" in FIG. 5D (that is, at a time when the balloon is about to inflate from the deflated state shown in FIG. 5B). The solenoid valve 66 is opened to supply the helium gas into the secondary tube line 18 so that the detected pressure P3 (FIG. 5A) becomes a predetermined value. The switching condition of the solenoid valve 66 is arbitrary. For example, it is opened "n" times for 8 milliseconds each in order to supply the helium gas to the secondary tube line 18, wherein "n" times is, for example, 2 to 10 times. The predetermined pressure value for P3 varies depending on the volume of the balloon 22. For example, for a balloon of 40 cc, the reference pressure is set to 10±5 mm Hg (gauged pressure) and, for a balloon of 30 cc, it is set to −80±5 mm Hg (gauged pressure). If the detected value of P3 is below the prescribed pressure value, the controller 10 causes the solenoid valve 68 to open in order to supply helium gas from the secondary helium gas tank 64 to the secondary tube line 18 until the sampled pressure P3 (FIG. 5A) becomes the predetermined value.

Next, the function of the driving apparatus 9b of this embodiment will be explained below.

Different volumes of balloon catheters 20 can be used in the driving apparatus 9b without replacing the pressure-transfer isolator 40. If a different volume of balloon catheter 20 is connected to the apparatus, the inside gas pressure of the secondary tube line 18 is determined again according to the volume of the new balloon 22. The pressure detected by the pressure sensor 15 is taken in at a time when the balloon 22 is about to inflate from the deflated state (i.e., at a timing indicated by "*2" in FIG. 5D), and helium gas is supplied to the secondary tube line 18 so that the detected pressure is consistent with the new reference value determined according to the volume of the new balloon 22.

It is not necessary to replace the pressure-transfer isolator 40, even when a different volume of balloon catheter 20 is used. If a small volume of balloon catheter is used, the reference gas pressure is set lower, and the inside gas pressure of the secondary tube line 18 is controlled so that the lower pressure is maintained. Consequently, the pressure at the end of the deflation cycle of the device is lowered, at least as compared with the pressure of the conventional device, and the pressure difference between the beginning and the end of the deflation becomes large. This allows the device being driven to deflate faster, and it can reduce the load on the heart of the patient.

Because the pressure-transfer isolator does not have to be changed, the pressure-transfer isolator can be fixed. Accordingly, a rigidity, presupposing a cartridge-type interchange, is not required any longer and the total weight of the driving apparatus can be reduced. The total oscillating time and the number of oscillation of the membrane (e.g., the diaphragm 52 shown in FIG. 2) built in the pressure-transfer isolator 40 can be controlled easily, which can facilitate the management and the maintenance of the membrane. The operator does not have to replace the pressure-transfer isolator 40.

The driving apparatus of the present invention is also capable of gradually decreasing the contribution ratio of the balloon catheter to the heart function of the patient when the patient is recovering. The controller 10b controls the gas pressure of the secondary tube line 18 connected to the balloon catheter 20, so that the gas pressure agrees with a predetermined pressure value at a time when the device being driven is about to inflate from the deflated state. The controller 10b can also change this predetermined pressure value according to the patient's condition. When the patient is recovering, the preset pressure value can be lowered in order to reduce the gas pressure in the balloon-side tube line. Consequently, the inflation amount of the device and, therefore, the contribution ratio of the device to the patient's heart function decrease to a desired level.

As compared with the technique disclosed in JP '396, the driving apparatus 9b of the present invention is capable of precisely controlling the contribution ratio of the device to the patient's heart function, excluding the fluctuation of the patient's blood pressure and the mechanical variation in the opening/closing time of the valve.

Unlike the driving apparatus of JP '952, the interior pressure P3 of the secondary tube line 18 is taken in at a time when the balloon 22 is about to inflate from the deflated state, and the driving gas is supplied to the secondary tube line 18 so that the pressure P3 reaches the predetermined pressure value. In the JP '952, a plateau pressure P4 is detected when the balloon 22 is in the inflated state, and the pressure is controlled so that the detected pressure becomes constant. On the other hand, in the present invention, the pressure P3 is detected at a point when the balloon 22 is about to inflate from the deflated state, and the pressure is controlled so that the detected pressure is consistent with a predetermined value. In other words, the sealed tube line 18, connected to the balloon 22, is filled with a constant volume of gas (having a constant molecular number or constant chemical equivalent ratio), while the balloon 22 is deflated. Then, the decreased amount of gas, due to penetration through the balloon wall, is monitored each time the balloon 22 is deflated.

The gas pressure is regulated so that the chemical equivalent of the driving gas, determined according to the volumes of the balloon and the tube line 18 (including the tubes and hoses), is consistent with the predetermined value, excluding the influence of the deformation of the balloon 22 due to the external force. Under this situation, the plateau pressure P4 (which is detected in the inflated state) can be observed for the purpose of checking a volume change of the balloon 22 due to an unexpected accident, such as a bend of the balloon 22. For example, if the plateau pressure P4 is higher than the normal pressure, it can be considered that the balloon 22 may be bending. If the plateau pressure P4 is lower than the normal pressure, it can be considered that the gas may be leaking due to an unexpected accident.

Even if the patient's blood pressure gets slightly higher than the plateau pressure P4, the interior pressure of the balloon 22 automatically approaches the patient's blood pressure because there is no limitation to the plateau pressure P4 and, as a result, the inflated volume of the balloon 22 is kept constant.

It should be understood that the present invention is not limited to this specific embodiment, and that many changes can be made within the scope of the invention.

For example, two pumps 4a and 4b are used in the second embodiment as the primary pressure generators. However, a single pump may be used as the primary pressure generator. In this case, a first pressure tank 2 is connected to the positive-pressure output port of the single pump, and a second pressure tank 3 is connected to the negative-pressure output port of the pump. The number of pumps and, therefore, the weight of the entire apparatus, as well as the energy consumption, can be reduced.

Although, in this embodiment, the third and fourth solenoid valves 11 and 12 are used as the pressure switching means, a three-way valve may be used to switch the pressure applied to the input port of the pressure-transfer isolator 40.

The gas flowing through the primary tube line 17 is not limited to air, and other fluids may be used in place of the air. Similarly, the gas flowing through the secondary tube line 18 is not limited to helium gas.

As a modification, a pressure generator that reciprocates the driving gas may be connected directly to the secondary tube line 18 without using the primary tube line 17 and the pressure-transfer isolator 40. Such a pressure generator comprises, for example, bellows 40a, and a driving means (e.g., a motor 40b) for inflating and compressing the bellows in the axial direction, as shown in FIG. 9. By driving the bellows 40 in the axial direction using the motor, the gas is supplied and removed directly to and from the secondary tube line 18 at a prescribed timing, thereby inflating and deflating the balloon 22. It is not necessary for this driving apparatus to adjust the stroke of the bellows.

Although a balloon catheter is driven by the driving apparatus in this embodiment, this driving apparatus can be used to drive any medical appliances that repeats inflation and deflation.

Third Embodiment

The overall structure of the driving apparatus according to the third embodiment is similar to the driving apparatus 9b of the second embodiment shown in FIG. 10. However, the control method of the controller 10b is different. Explanation will be made below focusing on this difference, and an explanation of the commonalities will be omitted.

In operation, the interior pressure PT1 of the first pressure tank 2 is set to about 300 mm Hg (gauged pressure) by driving the pump 4a shown in FIG. 10, and the interior pressure PT2 of the second pressure tank 3 is set to about −150 mm Hg (gauged pressure) by driving the pump 4b. The pressure applied to the input port of the pressure-transfer isolator 40 (FIG. 10) is switched between the first and second pressure tanks 2 and 3, respectively, by alternately driving the solenoid valves 11 and 12. The switching timing between the solenoid valves 11 and 12 is controlled by the controller 10b so as to be with the patient's heart beat.

The fluctuation of the pressures PT1 and PT2 detected by the sensors 5 and 6, respectively, are the same as those shown in FIG. 4A, and the pressure PT3 in the secondary tube line 18 detected by the pressure sensor 15 is the same as that in FIG. 4B. The peak pressure of the secondary tube line 18 is 289 mm Hg (gauged pressure), and the minimum is −114 mm Hg (gauged pressure). The pressure change in the secondary tube line 18 causes the volume of the balloon 22 to change, as shown in FIG. 4C. In this manner, the balloon 22 inflates and deflates in agreement with the patient's heart beat, thereby aiding or activating the heart function of the patient.

The controller 10b detects the pressure P3 of the secondary tube line 18 by the pressure sensor 15 at the end of the deflation state of the balloon 22 in order to compensate for natural gas leakage. This sampling timing of p3 is indicated in FIG. 5D.

Figure 12:
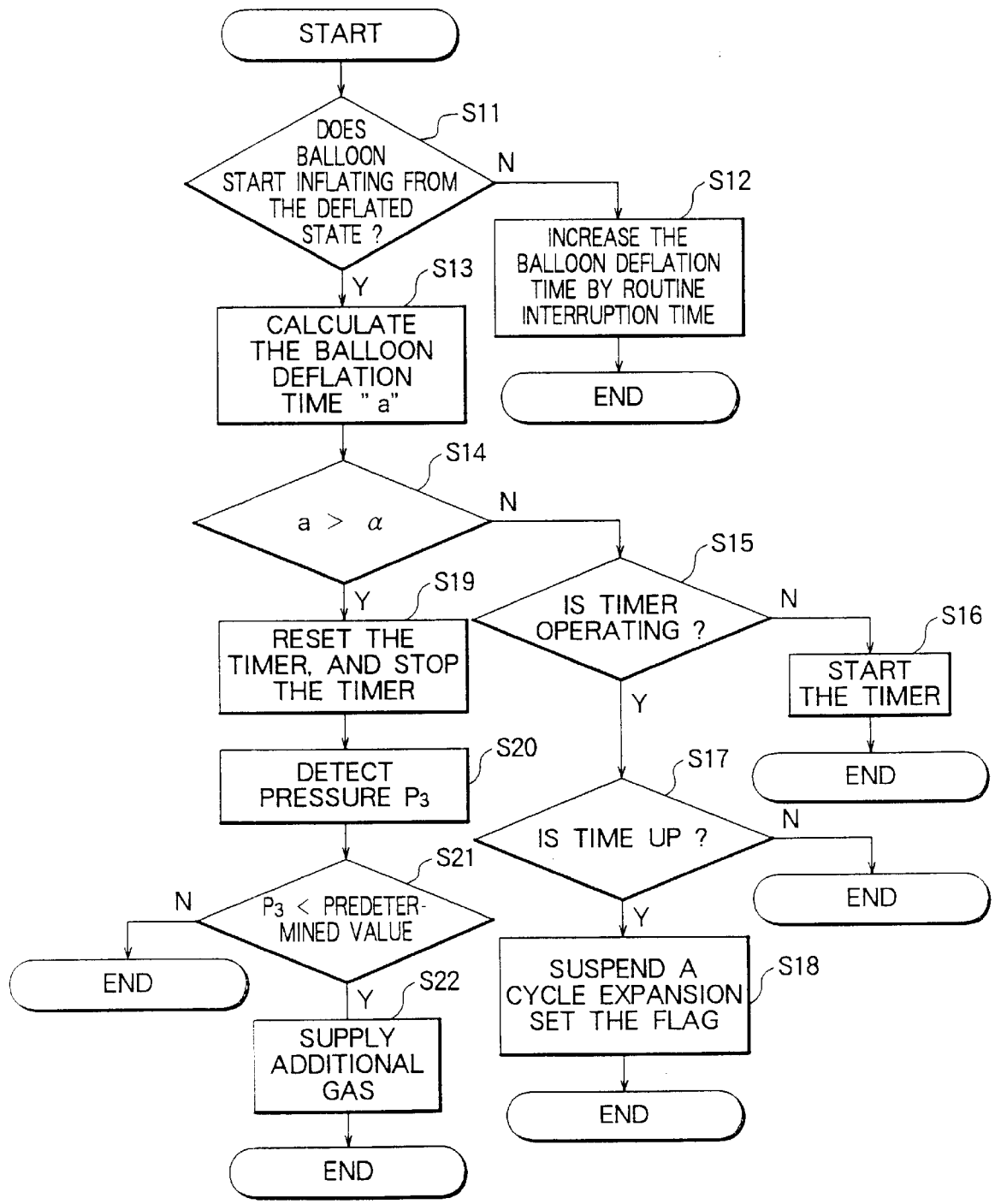
FIG. 12 is a flowchart showing the operation flow of the controller according to an embodiment of the present invention.

FIG. 12 is a flowchart showing the determination routine for-checking whether or not additional gas supply is required. This routine is an interrupt routine read out at a certain time interval by, for example, a programmable timer. The time interval is preferably 1 millisecond to 20 milliseconds. First, in step S11, it is determined if the balloon is about to inflate from the deflated state. If the determination result is NO in step S11, the deflation time is summed up in step S12, and the interrupt routine terminates. If the determination result is YES in step S11, the process proceeds to step S13, in which the deflation time "a" (FIG. 5B) of the balloon 22 is calculated. The deflation time "a" is calculated by, for example, measuring the switching cycle of the solenoid valves 11 and 12 shown in FIG. 10. The deflation time may be calculated from the pressure change in the secondary tube line 18 detected by the pressure sensor 15 shown in FIG. 10, or alternatively, it may be calculated based on the output signal from a device for continuously detecting the blood pressure change or the heart beat of the patient because the deflation time "a" is defined by the blood pressure change or the heart beat of the patient. The controller 10b functions as the deflation/inflation time calculator for performing step S13.

In step S14, it is determined if the calculated deflation time "a" is greater than the prescribed time "α". The prescribed time "a" is preferably within the range of, but not limited to, 100 ms to 500 ms, and more preferably, 150 ms to 300 ms. If the balloon 22 repeats inflation and deflation with the deflation time "a" shorter than the prescribed stable time "α", a pressure in the stable deflation state cannot be obtained even if the pressure sensor 15 detects the interior pressure of the secondary tube line 18 at a time when the balloon 22 is about to inflate from the deflated state. With such a short inflation/deflation cycle, the pressure change in the secondary tube line 18 becomes that shown in FIG. 11 and, consequently, the pressure P3', which is lower than the pressure P3 detected in the stable deflation state in the normal operation of the balloon 22 (according to the patient's heart beat), is detected.

If, in step S14, the deflation time "a" is shorter than the prescribed time "α", the process proceeds to step S15, where it is checked whether or not the software or hardware timer, that times up preferably in three minute to ten minute intervals, has started. If the timer has not started yet in step S15, it is started in step S16. If the timer has started in step S15, and if time is up in step S17, then a flag for suspending a cycle of inflation of the balloon 22 is set up in step S18. At the same time, the switching operation of the solenoid valve for inflating the balloon 22 (which is incorporated in another routine and is not shown in this figure) is also suspended in order to maintain the deflated state. In general, after a cycle of suspension, the condition of step S14 is satisfied, and the process proceeds to step S19. In step S19, the timer is reset to zero and stopped. Then, in step S20, a pressure P3 is detected. In step S21, it is determined if the pressure P3 is smaller than the prescribed pressure value. If YES in step S21, the driving gas is supplied to the secondary tube line 18 in step S22. If the system is programmed so that the gas supply operation is performed in a separate routine, a flag for starting that routine is set up in step S22. If the patient's heart beat is unstable, and if the condition of step S14 is satisfied in time before the timer is up, the timer is reset and stopped and, accordingly, the process does not proceeds to step S18 for suspending the balloon inflation. If the condition of step S14 is not satisfied before the timer is up, the process may proceeds to step S18. This can prevent an unnecessary suspension of the balloon inflation, thereby appropriately assisting the patient's heart function.

The pressures P3 of the secondary tube line 18 detected by the pressure sensor 15 is taken in at a timing indicated by "*2" in FIG. 5D (that is, at a time when the balloon is about to inflate from the deflated state shown in FIG. 5B). The solenoid valve 66, shown in FIG. 10, is opened to supply helium gas into the secondary tube line 18 so that the detected pressure P3 (FIG. 5A) becomes a predetermined value. The switching condition of the solenoid valve 66 is arbitrary. For example, it is opened n times for 8 milliseconds each in order to supply helium gas to the secondary tube line 18, wherein "n" times is, for example, two to 10 times.

For example, if the sampled pressure P3 is less than zero mm Hg (that is, the prescribed pressure value), the driving gas is supplied to the secondary tube line 18 so that P3 becomes about 10 mm Hg. In this embodiment, the threshold value for determining the necessity of gas supply can be varied according to the volume of the balloon 22. For instance, if a balloon of 40 cc is used, the interior pressure is regulated so that P3 becomes 10 mm Hg±5 mm Hg (gauged pressure), and if a balloon of 40 cc is used, the interior pressure is regulated so that P3 becomes −80 mm Hg±5 mm Hg (gauged pressure). If the sampled pressure P3 is below the threshold value, the controller 10b causes the solenoid valve 66 to open in order to supply the helium gas from the secondary helium gas tank 64 to the secondary tube line 18 until the sampled pressure P3 (FIG. 5A) becomes the predetermined value.

Thus, in the third embodiment, even if the inflation/deflation cycle of the balloon 22 is short, an appropriate amount of driving gas can be supplied to the secondary tube line 18 based on the pressure detected in the stable deflation state. This means that even if the heart beat rate of the patient is high, the situation, where an excessive amount of driving gas is supplied, can be prevented. Although the inflation of the balloon 22 is suspended for a beat of the patient's heart, or occasionally, for two or more beats, it does not adversely affect the medical treatment of the patient using the balloon because the suspension time is very short. As compared with the conventional driving apparatus in which the entire driving gas in the secondary tube line 18 is substituted, the driving apparatus of this embodiment is economical because of reduced gas consumption.

Unlike the driving apparatus disclosed in JP '952, the interior pressure P3 of the secondary tube line 18 is taken in at a time when the balloon 22 is about to inflate from the deflated state, and the driving gas is supplied to the secondary tube line 18 so that the pressure P3 reaches the predetermined pressure value. In JP '952, a plateau pressure P4 is detected when the balloon 22 is in the inflated state, and the pressure is controlled so that the detected plateau pressure P4 becomes constant. On the other hand, in this embodiment, the pressure P3 is detected at the end of the deflated state of the balloon 22, and the pressure is controlled so that the detected pressure is consistent with a predetermined value. In other words, the sealed tube line 18, connected to the balloon 22, is filled with a constant volume of gas (having a constant molecular number or constant chemical equivalent ratio), while the balloon 22 is deflated. Then, the decreased amount of gas, due to penetration through the balloon wall, is monitored each time the balloon 22 is deflated.

The gas pressure is regulated so that the chemical equivalent of the driving gas, determined according to the volumes of the balloon and the tube line 18 (including the tubes and hoses), is consistent with the predetermined value, excluding the influence of the deformation of the balloon 22 due to the external force. Under this situation, the plateau pressure P4 (which is detected in the inflated state) can be observed for the purpose of checking a volume change of the balloon 22 due to an unexpected accident, such as a bend of the balloon 22. For example, if the plateau pressure P4 is higher than the normal pressure, it can be considered that the balloon 22 may be bending. If the plateau pressure P4 is lower than the normal pressure, it can be considered that the gas may be leaking due to an unexpected accident.

This embodiment can be modified so that the inflated state of the balloon 22 is kept sufficiently long to detect a stable pressure P4, even if an unexpected accident happened, and so that the detected pressure is kept at a predetermined value. In this case, the pressure P4 is taken in at a time where the balloon 22 is about to deflate from the inflated state.

Figure 13:
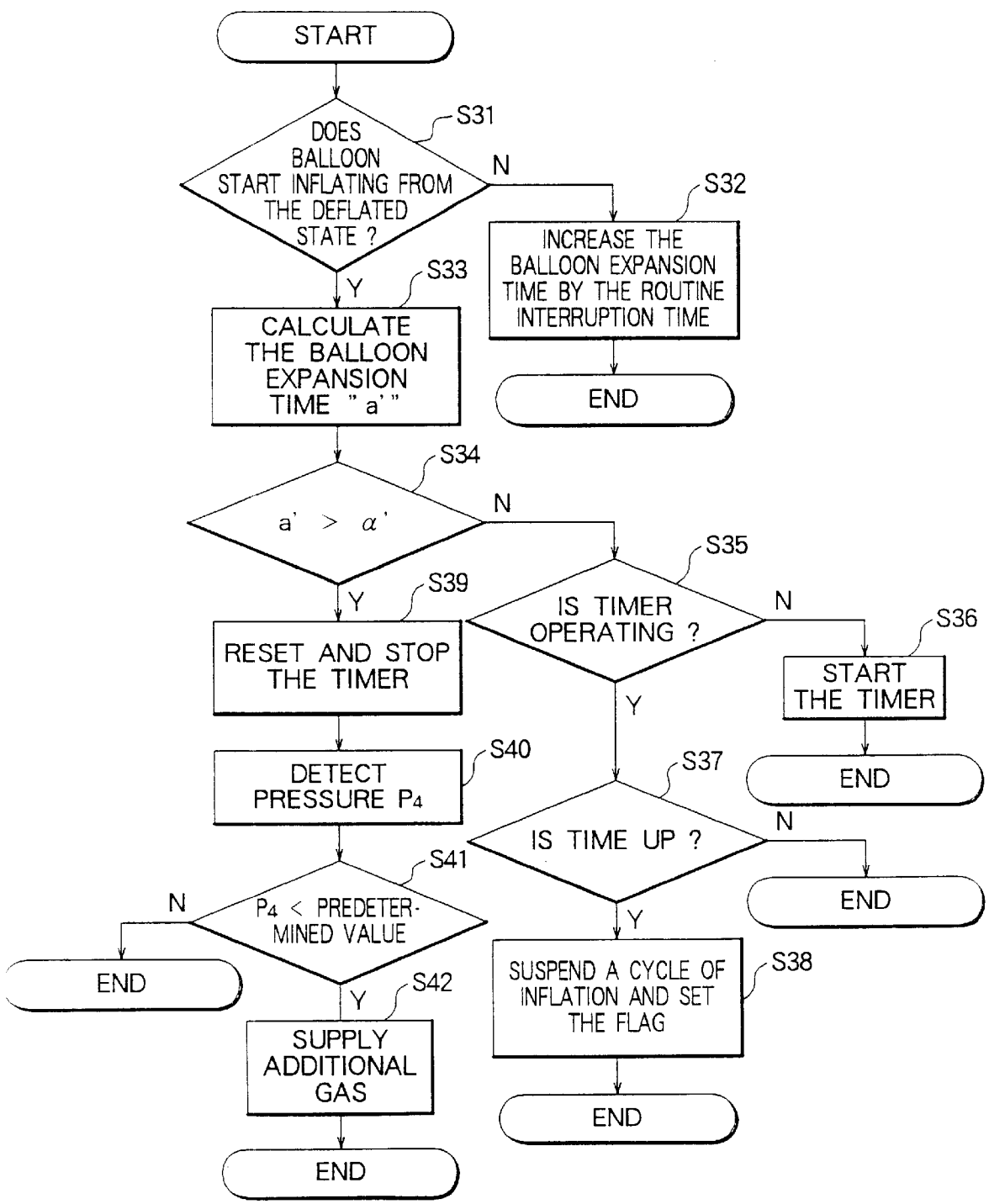
FIG. 13 is a flowchart showing the operation flow of the controller according to another embodiment of the present invention.

This modified routine is shown in FIG. 13. The term "inflation" used in steps S11 through S22 in FIG. 12 is replaced with "deflation" in steps S31 through S42 in FIG. 13, and the term "deflation" used in steps S11 through S22 in FIG. 12 is replaced with "inflation" in steps S31 through S42 in FIG. 13. The other operations are the same as those in FIG. 12, and the explanation thereof will be omitted here.

Fourth Embodiment

The driving apparatus according to the fourth embodiment is similar to that in the third embodiment, and the only difference is in the function of the controller 10b.

Figure 14:
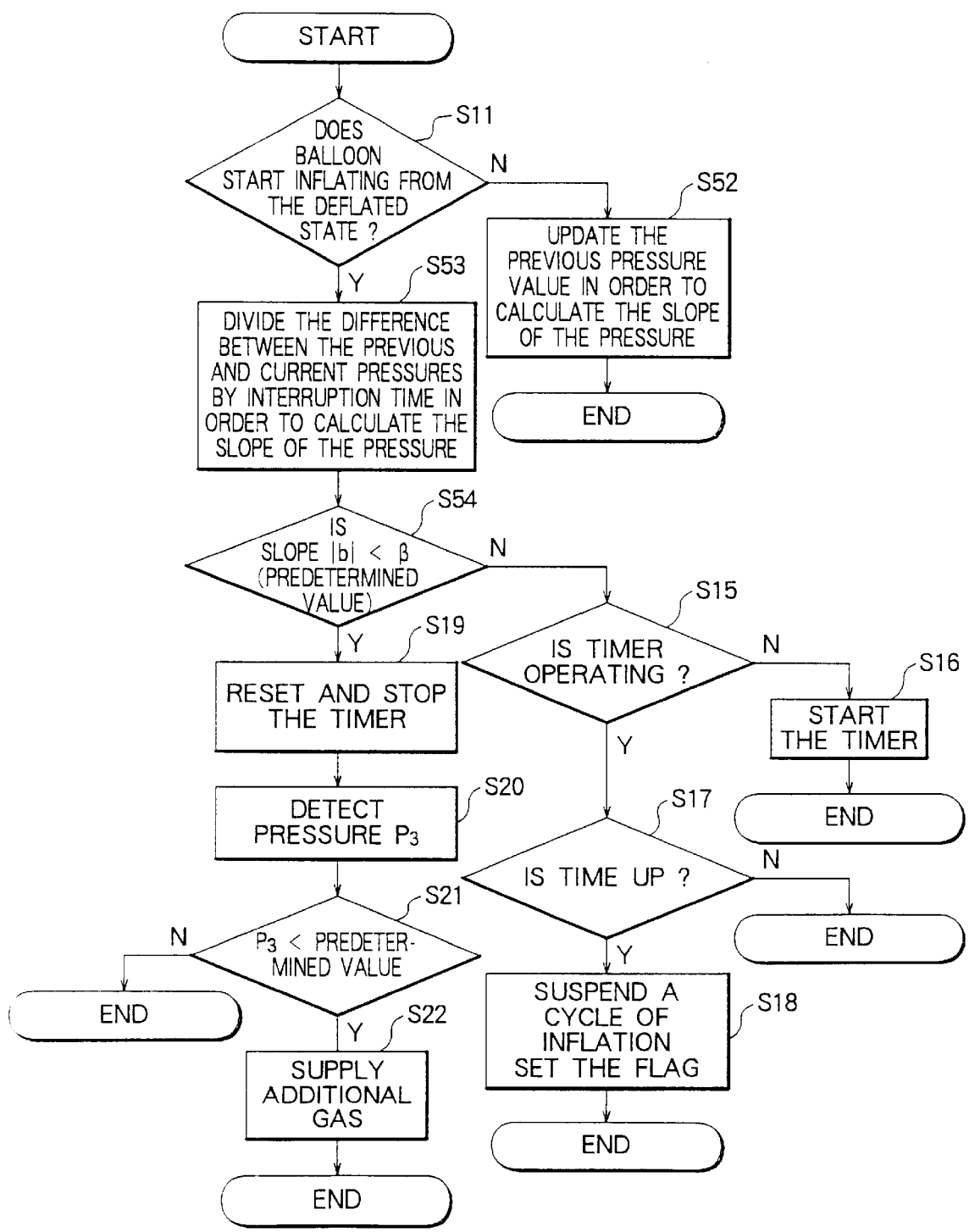
FIG. 14 is a flowchart showing the operation flow of the controller according to still another embodiment of the present invention.

FIG. 14 is a flowchart showing the operation of the controller 10b. The same steps as those in FIG. 12 are denoted by the same symbols, and a common explanation thereof will be omitted here. The difference will be explained with reference to the flowchart in FIG. 14.

In step S52, the previous pressure value is updated in order to calculate the slope of the interior pressure of the secondary tube line 18. Then, when the balloon 22 starts inflating from the deflated state, the slope "b" of the pressure is calculated in step S53 based on the difference between the current pressure and the previous pressure and dividing this difference by time. The absolute value of the slope "b" is compared with a prescribed value "β" in step S54. The value of "β" is preferably with the range of, but not limited to, zero mm Hg/sec to 100 mm Hg/sec, and more preferably, between zero mm Hg/sec to 50 mm Hg/sec. The other operations are the same as those in the third embodiment.

Figure 11:
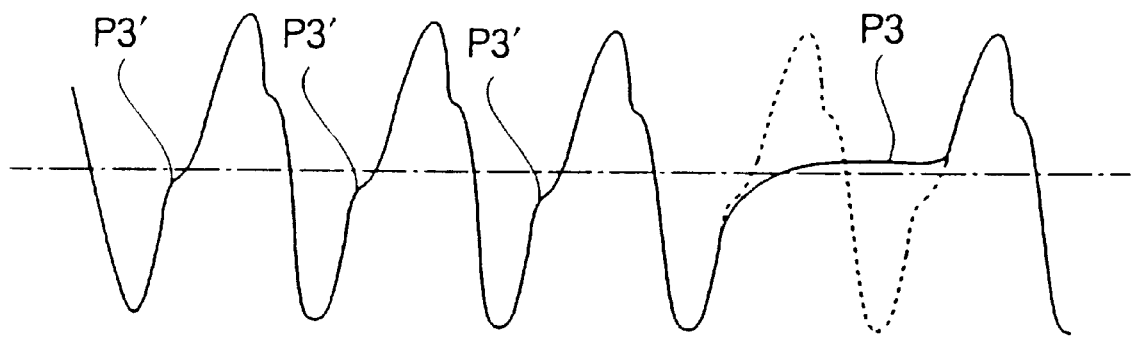
FIG. 11 shows a pressure change in the secondary tube line (and the balloon) when the patient's heart beat rate is high.

If the absolute value of the slope "b" is smaller than the prescribed value, it is implied that the detected pressure is in the stable state (as shown in FIG. 5A). Then, the interior pressure of the secondary tube line 18 at this stable moment is taken in, and an appropriate amount of driving gas is supplied based on this pressure. If the absolute value of the slope "b" is greater than the prescribed value "β" (as shown in FIG. 11), the process proceeds to step S15, and a certain time period is allowed to pass to see if the absolute value of the slope "b" becomes smaller than "β". If the absolute value of the slope "b" is still greater than after time is up, then one or more cycles of inflation are suspended in step S18 in order to make the slope "b" smaller than "β". Thus, the pressure P3 of the secondary tube line 18 is taken in the stable deflation state with the slope "b" smaller than "β", and the gas is supplied based on this pressure P3.

In this manner, an appropriate amount of gas is supplied to the secondary tube line 18 and the balloon 22. Even if the patient's heart beat rate increases, the inside gas pressure of the secondary tube line 18 is controlled so as not to supply an excessive amount of gas, and problems associated with excessive gas supply can be eliminated. Suspension of one or more cycles of inflation does not adversely affect the medical treatment of the patient using the balloon 22 because such a suspension time is very short. As compared with the conventional driving apparatus in which the entire driving gas in the secondary tube line is regularly substituted, the driving apparatus of this embodiment is economical because of reduced gas consumption.

Fifth Embodiment

Figure 15B:
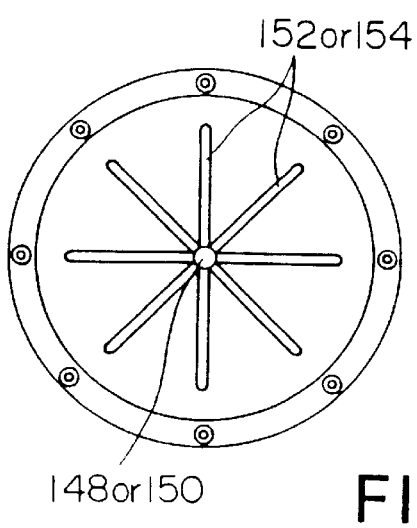
FIG. 15B is a front view of the inside of the casing.
Figure 15A:
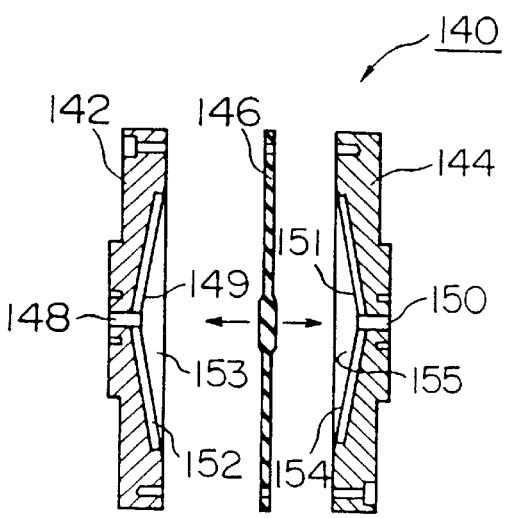
FIG. 15A is an exploded side view of the pressure-transfer isolator according to an embodiment of the present invention.
Figure 15C:
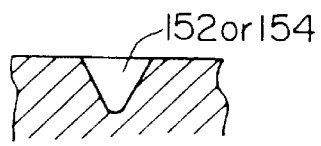
FIG. 15C is a cross-sectional view of the groove.

FIGS. 15A through 15C illustrate the pressure-transfer isolator 140 according to the fifth embodiment of the present invention. This pressure-transfer isolator 140 is used in the driving apparatus 9b for driving the IABP balloon catheter 20 shown in FIG. 10, in place of the pressure-transfer isolator 40 shown in FIG. 2.

Since the overall structure of the driving apparatus 9b has already been explained above, explanation below will be given mainly on the pressure-transfer isolator 140.

As shown in FIG. 15A, the pressure-transfer isolator 140 has a first casing 142, in which an input port (i.e., a first port) 148 is formed, and a second casing 144, in which an output port (i.e., a second port) 150 is formed. The input port 148 is connectable to the primary tube line 17, while the output port 150 is connectable to the secondary tube line 18. The first casing 142 has a first inner surface 149 which forms a conical recess in the first casing 142. The second casing 144 has a second inner surface 151 which also forms a conical recess in the second casing 144. The first and second inner surfaces 149 and 151 face each other when the first and second casings 142 and 144 are assembled. The casings 142 and 144 are made of a material having little deformation, such as a metal.

When the casings 142 and 144 are assembled by means of, for example, bolts, an inner space is formed inside. A diaphragm (i.e., a flexible membrane) 146 is placed between the first and second casings 142 and 144. The diaphragm 146 partitions the inner space formed by the casings 142 and 144 into two chambers, namely, a first chamber 153 connected to the input port 148 and a second chamber 155 connected to the output port 150. FIG. 15A shows the first and second casings 142 and 144, and the diaphragm 146 in an exploded view.

Figure 16A:
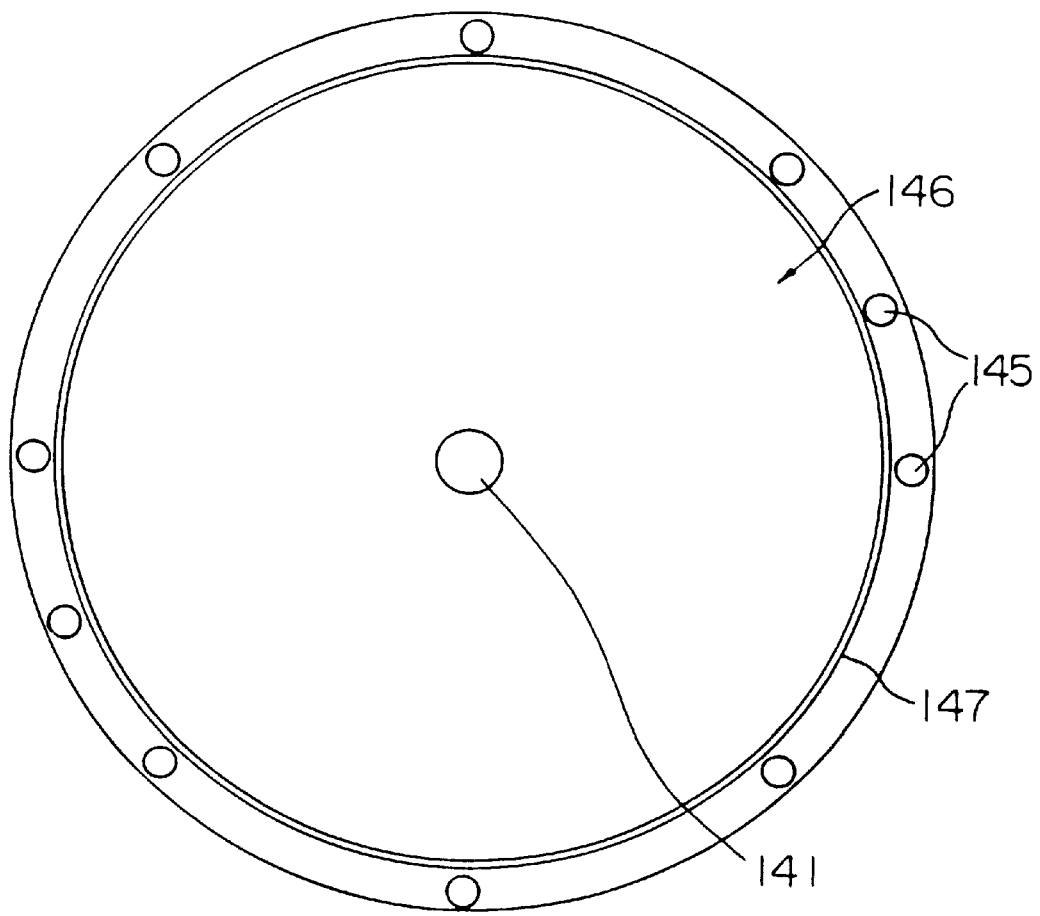
FIG. 16A is a front view of the diaphragm.
Figure 16B:
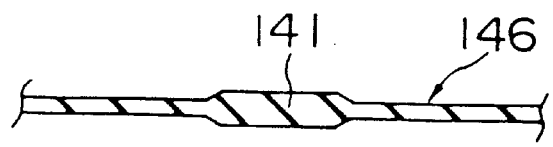
FIG. 16B is a cross-sectional view of the center part of the diaphragm.
Figure 16C:
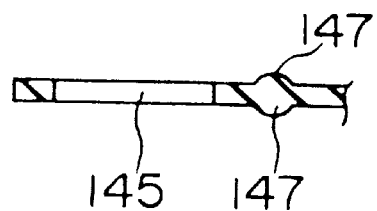
FIG. 16C is a cross-sectional view of the edge part of the diaphragm.

The diaphragm 146 is a disc-like elastic membrane as shown in FIGS. 16A through 16C, and it is made of, for example, any one of the groups including: diene group rubber, such as styrene-butadiene rubber (SBR), butadiene rubber (BR), isoprene rubber (IR), nitrylbutadiene rubber (NBR), and chloroprene rubber (OR); olefine group rubber, such as butyl rubber (IIR), ethylene-propylene-dienta rubber (EPDR), acrylic rubber, polyethylene chlorosulfonide rubber; fluorocarbon rubber; silicon rubber; urethane rubber; and polysulfide rubber. It is preferable that the surface of the diaphragm 146 is embossed.

There is a thick part 141 formed in the center of the diaphragm 146 as shown in FIG. 16B. The diameter of the thick part 141 is slightly larger than the inner diameters of the input port 148 and the output port 150, shown in FIG. 15A. The thickness of the diaphragm, other than the center thick part 141, is preferably within a range of, but not limited to, 0.5 mm to 1.5 mm, while the thickness of the thick part 141 is preferably within a range of, but not limited to, 1 mm to 2 mm.

Bolt holes 145 are formed along the circumference of the diaphragm 146, and bolts are screwed into the bolt holes when the casings 142 and 144 (FIG. 15A) are assembled. A sealing projection 147 having a semicircular cross-sectional area is formed along a circumference of the diaphragm 146 inside the bolts holes, as shown in FIG. 16A. The sealing projection 147 fits tightly with the joint faces of the casings 142 and 144 when they are assembled, whereby the inner space formed by the casings 142 and 144 is partitioned by the diaphragm 146 into the first chamber 153 and the second chamber 155 which do not communicate directly with each other.

Although the fluid flow is blocked by the diaphragm 146 between the first and second chambers 153 and 155, the pressure change (or the volume change) occurring in the first chamber 153 is transferred to the second chamber via the displacement of the diaphragm 146, which appears as the pressure change (or the volume change) in the second chamber 155. This arrangement allows the pressure change in the primary tube line 17 to be transferred to the secondary tube line 18 without connecting the primary tube line 17 directly to the secondary tube line 18. This arrangement also makes it easy to regulate the amount of gas (i.e., the chemical equivalent of the gas) filled in the secondary tube line 18.

As shown in FIGS. 15A through 15C, grooves 152 and 154 are formed in the first and second inner surfaces 149 and 151 of the casings 142 and 144, respectively. The grooves 152 and 154 extend in the radial directions from the input and output ports 148 and 150, which are positioned in the center of the casings. In this embodiment, eight grooves 152 and eight grooves 154 are formed in the casings 142 and 144, respectively. The cross-sectional area of the grooves 152 and 154 is arbitrary, for example, an inverse triangle, as shown in FIG. 15C, or a semicircle.

The width of the groove is preferably within the range of, but not limited to, 0.2 mm to 10 mm, and its depth is preferably 0.3 mm to 5 mm. These grooves 152 an 154 serve as relief passages. The upper and lower limits of the width, and the lower limit of the depth of the groove are determined so that the groove effectively works as the relief passage. The upper limit of the depth of the groove is determined taking the thickness of the casing into account.

The pressure-transfer isolator 140 is used as a part of the driving apparatus 9*b* shown in FIG. 10.

In this embodiment, the fluid flowing through the primary tube line 17, which is connected to the input port 148 (FIG. 15A) of the pressure-transfer isolator 140, is air, and the fluid flowing through the secondary tube line 18, which is connected to the output port 150, (FIG. 15A) is helium gas because a gas having a small mass can improve the inflation/deflation response of the balloon 22.

As shown in FIG. 10, two pumps 4*a* and 4*b* are provided as a pressure generator in the primary tube line 17. The first pump 4*a* is a positive-pressure generator (called a compressor), and the second pump 4*b* is a negative-pressure generator. The positive-pressure output port of the first pump 4*a* is connected to the first (positive) pressure tank 2 via a regulator valve 7. The negative-pressure output port of the second pump 4*b* is connected to the second (negative) pressure tank 3 via a throttle valve 8.

Pressure sensors 5 and 6 are provided to the first and second pressure tanks 2 and 3, respectively, in order to detect the interior pressures of the tanks 2 and 3. The first and second tanks 2 and 3 are also connected to the input ports of the first and second solenoid valves 11 and 12, respectively. The switching operations of the solenoid valves 11 and 12 are controlled by the controller (not shown) in synchronization with, for example, the patient's heart beat. The output ports of the solenoid valves 11 and 12 are connected to the input port 148 of the pressure-transfer isolator 140, shown in FIG. 15A.

Figure 17:
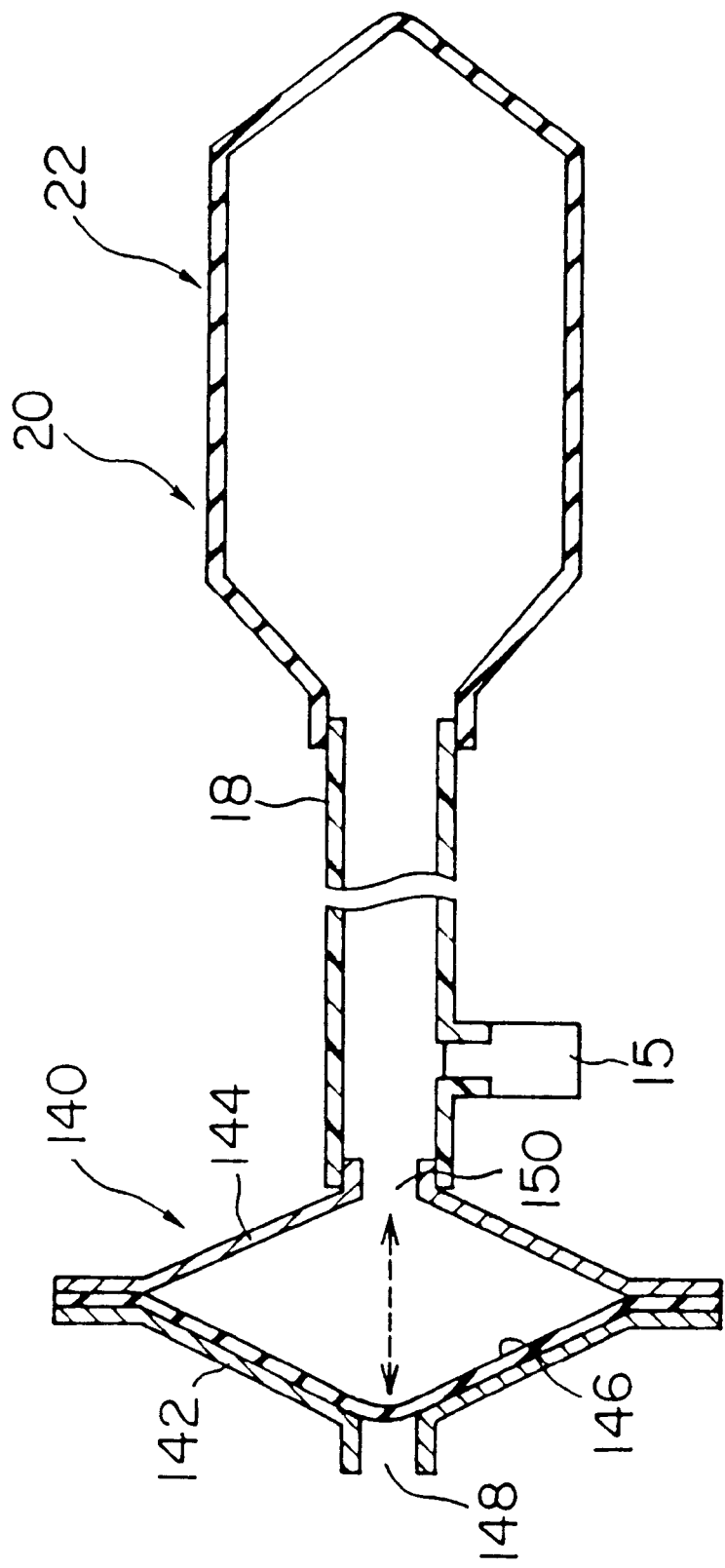
FIG. 17 is a cross-sectional view showing the positional relationship between the balloon and the pressure-transfer isolator.

The output port 150 of the pressure-transfer isolator 140 is connected to the secondary tube line 18, shown in FIGS. 10 and 17. The secondary tube line 18, which comprises hoses and tubes, is connected to the inside of the balloon 22 in a sealed manner, and the secondary tube line 18 and the balloon 22 form a sealed circuit filled with helium gas. A pressure sensor 15 is provided to the secondary tube line 18 in order to detect the interior pressure of the secondary tube line 18. The output of the pressure sensor 15 is connected to the input of the controller.

A vacuum pump is also connected to the secondary tube line 18 via an solenoid valve 16. The solenoid valve 16 and the vacuum pump are used to evacuate the secondary tube line 18 prior to filling the helium gas in the secondary tube line 18. Accordingly, in the normal operation, the solenoid valve 16 is closed and the vacuum pump is not activated.

A gas supply system 60b is connected to the secondary tube line 18 in order to supply an appropriate amount of helium gas into the secondary tube line 18 so that the chemical equivalent of the helium gas inside the secondary tube line 18 is always kept constant throughout the driving operation of the apparatus. Since the detailed structure of the gas supply system 60b has already been explained above, the explanation thereof will be omitted here.

In the operation of the driving apparatus of this embodiment, the interior pressure PT1 of the first pressure tank 2 is set to about 300 mm Hg (gauged pressure) by driving the first pump 4a, shown in FIG. 10, and the interior pressure PT2 of the first pressure tank 3 is set to about –150 mm Hg (gauged pressure) by driving the second pump 4b. The pressure applied to the input port of the pressure-transfer isolator 140, shown in FIGS. 15A through 15C, is switched between the first and second pressure tanks 2 and 3 by alternately driving the solenoid valves 11 and 12. The switching timing is controlled by the controller 10b according to the patient's heart beat.

If a positive pressure is introduced from the input port 148 (FIG. 15A), the diaphragm 146 moves toward the conically hollowed inner surface 151 of the second casing 144, whereby the interior pressure of the secondary tube line 18 and the balloon 22 show in FIGS. 10 and 17 increases and, consequently, the balloon 22 inflates. If a negative pressure is introduced from the input port 148, the diaphragm 146 moves toward the conically hollowed inner surface 149 of the first casing 144, whereby the interior pressure of the secondary tube line 18 and the balloon 22 decreases and, consequently, the balloon 22 deflates.

The pressures PT1 and PT2, detected by the pressure sensors 5 and 6 (FIG. 10), respectively, are shown in FIG. 4A, and the pressure PT3 of the secondary tube line 18, detected by the pressure sensor 15, is shown in FIG. 4B. The peak pressure of the secondary tube line 18 is 289 mm Hg (gauged pressure), and the minimum is –114 mm Hg (gauged pressure) in this example. The pressure change of the secondary tube line 18, shown in FIG. 4B, causes the volume of the balloon 22 to change, as shown in FIG. 4C. Consequently, the balloon 22 inflates and deflates repeatedly according to the patient's heart beat.

In this embodiment, the pressure PT3 detected by the pressure sensor 15 is taken in at a time when the balloon 22 starts inflating from the deflated state (including a moment immediately before the balloon actually starts inflating). The solenoid valve 66 (FIG. 10) is opened in order to supply the helium gas into the secondary tube line 18 so that the pressure PT3 becomes the prescribed pressure value. The opening control for the solenoid valve 66 is the same as in the previous embodiments.

As has been described, grooves 152 and 154, extending in radial directions, are formed in the hollowed inner surfaces 149 and 151 of the casings 142 and 144, as shown in FIGS. 15A through 15C. These grooves 152, 154 can drive off the residual gas residing between the inner surfaces 149 and 151 and the diaphragm 146 into the first port and the second port 150, so that no residual gas flows into the first or second port 148 or 150 at a timing right before changing the pressure. If the residual gas flows into the tube lines, a pressure fluctuation may be caused. In this embodiment, such fluctuation can be prevented, and the small peak SP, which appears in the flat stable portion (indicated as P4 in FIGS. 21 through 24) of each pressure pulse in the conventional driving apparatus, can be eliminated.

Thus, in this embodiment, the pressure P4 or P3, which momentarily becomes stable in each pressure pulse, can be detected precisely, and the operation state of the balloon 22 can be known accurately based on the detected pressure.

In order merely to eliminate the small peak SP occurring in the plateau pressure P4 shown in FIGS. 21 through 24, grooves may formed only in the second inner surface 151 of the second casing 144 so that the residual gas residing between the second inner surface 151 and the diaphragm surface is escaped to the second port 150 before switching a state of the balloon 22 from inflation to deflation. The diaphragm surface contacts with the second inner surface 151 right before the switching timing. However, in this embodiment, grooves 152 and 154 are formed in both the first and second casings 142 and 144 for the purpose of eliminating not only the small peak SP of the plateau pressure P4 region shown in FIGS. 21 through 24, but also the small peak (not shown) appearing in the pressure P3 region.

Sixth Embodiment

In the sixth embodiment, two grooves 154, extending in radial directions from the second (output) port 150, are formed only in the second inner surface 151 of the second casing 144 of the pressure-transfer isolator, as shown in FIGS. 18A and 18B. The two grooves 154 extends in degree opposite directions (i.e., 180 degree apart from each other). The width and the depth of each groove 154 is the same as those in the fifth embodiment. The first inner surface of the first casing, which is assembled with the second casing 144 via the diaphragm, does not have a groove.

The other structure is the same as that in the fifth embodiment, and the explanation thereof will be omitted here.

Although, in this embodiment, the number of grooves 154 is reduced, as compared with the pressure-transfer isolator shown in FIG. 15A, a similar effect of reducing the small peak SP can be achieved, which will be described below in more detail using an actual example.

Seventh Embodiment

FIGS. 19A and 19B show the pressure-transfer isolator according to the seventh embodiment. In this embodiment, two ribs 154a are formed only in the second inner surface 151a of the second casing 144a. The two ribs 154a extend radially from the second (output) port 150a in opposite directions (i.e., 180° from each other). By forming these ribs 154a in the second inner surface 151a, relief passages, communicating with the output port 150a, are formed between the diaphragm (not shown) and the second inner surface 151a, when the diaphragm comes into contact with the second inner surface 151a. The ribs 154a do not necessarily extend continuously from the output port 150a, and the ribs 154a may be formed radial directions so as to be slightly apart from the output port 150a.

The height of the ribs 154a is preferably within the range of, but not limited to, 0.15 mm to 3 mm, and more preferably between 0.3 mm to 2 mm, because if the ribs are too low, the drain effect decreases, and if the ribs are too high, they prevent the oscillatory displacement of the diaphragm. The number of ribs 154a is preferably two or more.

The first casing that is assembled with the second casing 144a via the diaphragm does not necessarily have grooves or ribs in its inner surface. However, the ribs 154a, shown in FIGS. 19A and 19B, or the grooves 154, shown in FIGS. 18A and 18B, may be formed in the first inner surface of the first casing.

The other structure is the same as that in the previous embodiment, and the explanation thereof will be omitted here. It was confirmed that the ribs 154a have the same effect as the grooves 154 in the actual example which will be described below.

Eighth Embodiment

Figure 20A:
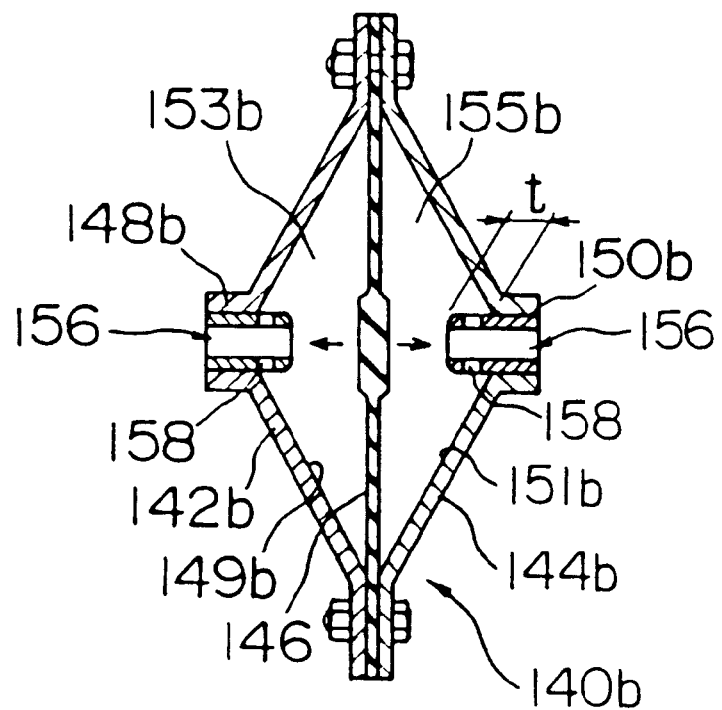
FIG. 20A is a cross-sectional view of the pressure-transfer isolator according to still another embodiment.
Figure 20B:
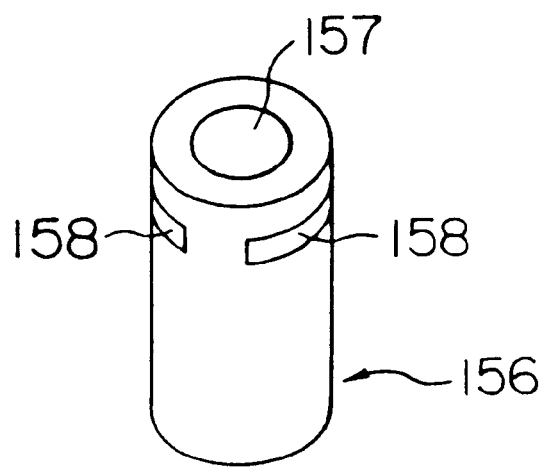
FIG. 20B is a perspective view of the nozzle used in the pressure-transfer isolator.

FIGS. 20A and 20B show the pressure-transfer isolator 140b according to the eighth embodiment of the invention. This pressure-transfer isolator 140b has a first casing 142b having a hollowed inner surface (referred to as the first inner surface) 149b, and a second casing 144b having a hollowed inner surface (referred to as the second inner surface) 151b, as in the fifth embodiment. A diaphragm 146 is placed between the first and second casings 142b and 144b to partition the inner space formed by these casings into a first chamber 153b and a second chamber 155b, as in the fifth embodiment. The pressure introduced into the first chamber 153b causes the diaphragm 146 to oscillate between the first and second casings and to alternately contact the first and second inner surfaces 149b and 151b, as in the pressure-transfer isolator shown in FIGS. 15A through 15C.

The feature of this embodiment is that the nozzles 156, shown in FIG. 20B, are attached to each of the first (input) port 148b and the second (output) port 150b, instead of forming grooves or ribs in the inner surfaces 149b and 151b. Each of the nozzles 156 has a penetrating hole 157 extending along the longitudinal axis. An elongated relief hole 158 is formed in the side wall of the nozzle 156 near the tip of the nozzle. The relief hole 158 communicates with the penetrating hole 157. The ends of the nozzles 156 project from the input and output ports 148b and 150b toward the inner space of the first and second chambers 153a and 153b by a height "t", so that the relief holes 158 are positioned completely inside the first and second chambers 153b and 155b. The height "t" is preferably within the range of, but not limited to, 0.5 mm to 5 mm.

In this pressure-transfer isolator 140b, the residual gas existing between the diaphragm 146 and the inner surfaces 149b and 151b is efficiently driven off from the relief holes 158 and the penetrating holes 157 when the diaphragm 146 alternately comes into contact with the inner surfaces 149b and 151b. This can prevent the small peak SP from occurring in the detected plateau pressure (FIG. 22) due to the residual gas when the diaphragm 146 is leaving from the inner surfaces 149b and 151b.

Figure 22:
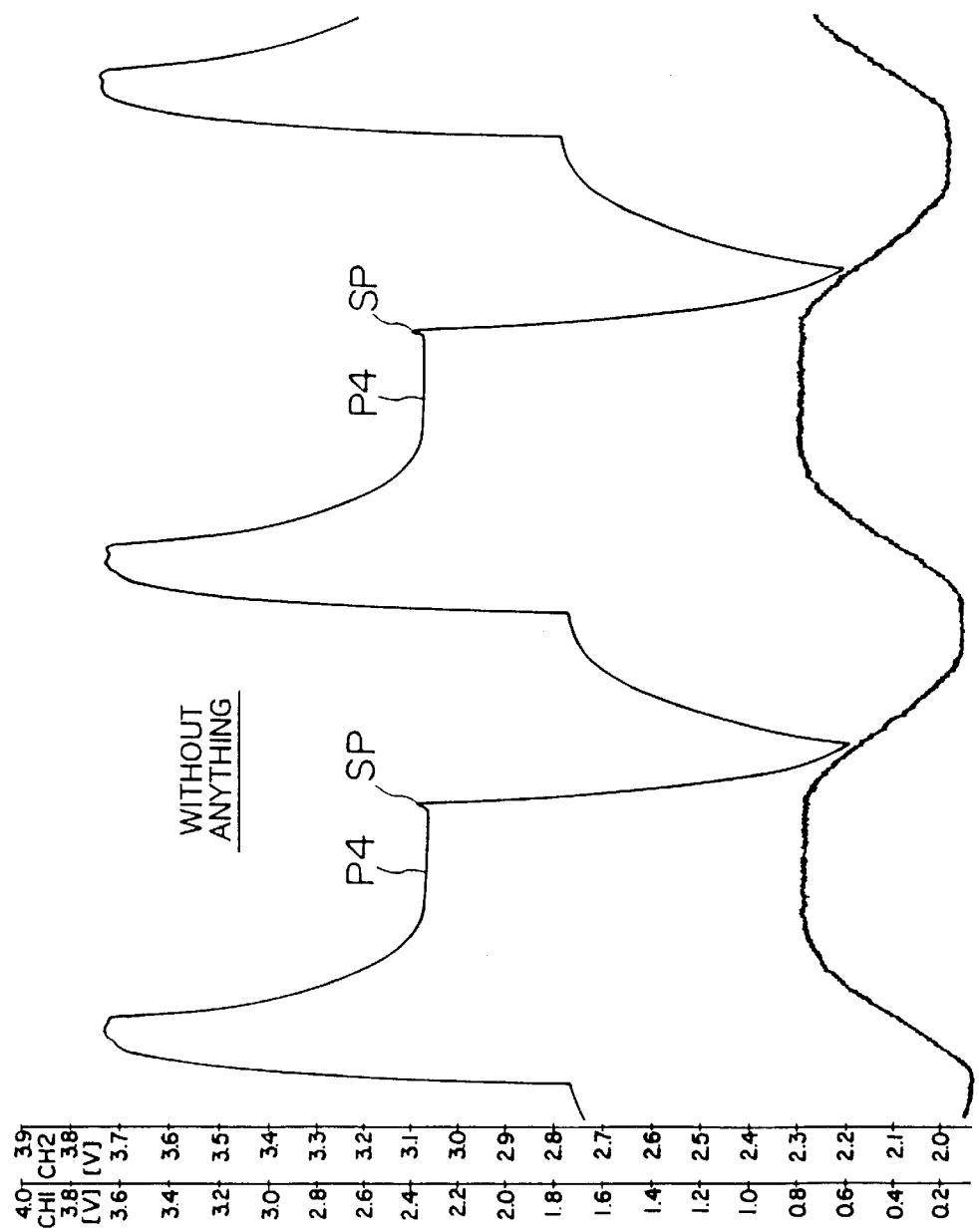
FIG. 22 is a graph showing a pressure change in a conventional pressure-transfer isolator of an comparison example.

To merely eliminate the small peak SP from the plateau pressure P4 shown in FIG. 22, it is sufficient to provide a nozzle 156 only to the output port 150b (connected to the balloon), shown in FIG. 20A.

The pressure-transfer isolator 140b according to this embodiment, can achieve the same effect as the pressure-transfer isolator 140, shown in FIGS. 15A through 15C, and it can accurately detect the momentarily stabilized flat pressure P4 which is applied to the balloon 22. As a result, the operational state of the balloon can be precisely known.

The pressure-transfer isolator of the present invention is not limited to the embodiments described in the firth to eighth embodiments, and there are many other modifications within the spirit and scope of the invention.

Figure 20C:
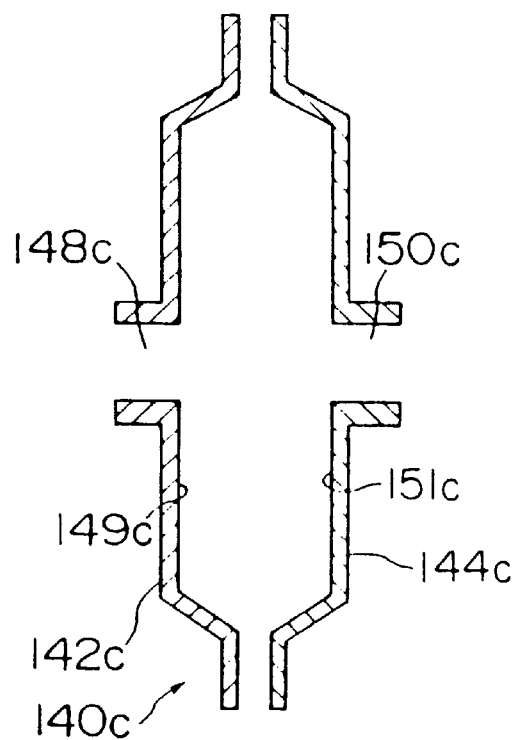
FIG. 20C is an exploded cross-sectional view of the pressure-transfer isolator according to still another embodiment.

For example, the shape of the casings of the pressure-transfer isolator is not limited to the examples in the fifth through eighth embodiments, and the casings can take any shape that can form a inner space, in which a diaphragm is placed. For instance, the casings may have the shape shown in FIG. 20C, where the casings 142c and 144c of the pressure-transfer isolator 140c has a boat-like cross-sectional shape with the ports 148c and 150c in the middle. However, the casing having a conically scooped inner surface, as shown in FIGS. 15A through 15C, is preferable because of its high responsiveness to the oscillation of the diaphragm and the improved inflation/deflation response of the balloon.

Figure 20D:
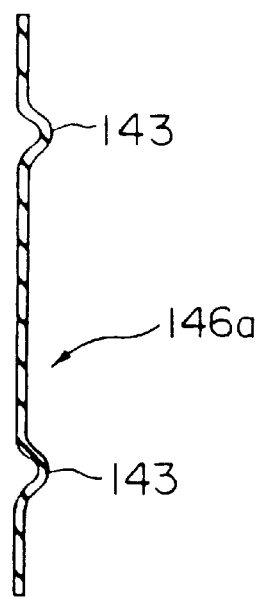
FIG. 20D is a cross-sectional view of the diaphragm provided inside the casing.

The shape of the diaphragm may also be modified in various manners. For example, a continuous or discontinuous colgate 143 may be formed along the circumference of the diaphragm 146a, as shown in FIG. 20D. The colgate 143 can improve the durability of the diaphragm 146a.

Ninth Embodiment

Figure 25:
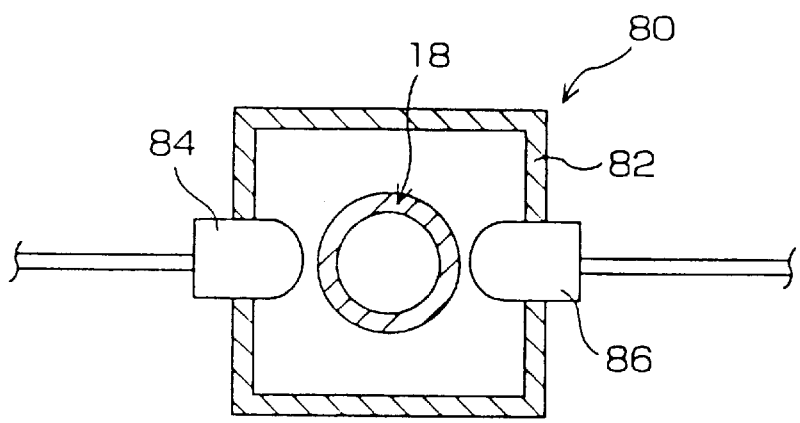
FIG. 25 is a schematic diagram of the monitor used in the medical-appliance driving apparatus according to an embodiment of the present invention.

FIG. 25 illustrates the monitor 80 according to the ninth embodiment of the present invention, which is designed for medical-appliance driving apparatuses. The monitor 80 is installed in, for example, the driving apparatus 9c (FIG. 27) for inflating and deflating the balloon 22 of an IABP balloon catheter 20. The driving apparatus, shown in FIG. 27, is almost the same as the driving apparatus 9b, shown in FIG. 10, and the same elements are denoted by the same numerical symbols.

As has been explained above, the balloon 22 of the IABP balloon catheter 20 is inflated and deflated using helium gas, which has a small mass and a high response. Generating positive and negative pressures directly in the helium gas by means of a pump or a compressor is uneconomical because of increased gas consumption. Also, the volume control becomes difficult in the direct pressure generation. Accordingly, this embodiment employs the arrangement shown in FIG. 27, in which the secondary tube line 18, connected to the balloon 22 and the pressure-transfer isolator 40, is isolated from the primary tube line 17 connected to the pumps 4a and 4b which comprise a pressure generator. The pressure-transfer isolator 40 is illustrated in FIG. 28. This pressure-transfer isolator 40 has a first chamber 46 and a second chamber 48 which are partitioned by a diaphragm 52 and a plate 50. The plate 50 may be omitted, and only the diaphragm 52 may be used to partition the inner space of the isolator 40.

Figure 27:
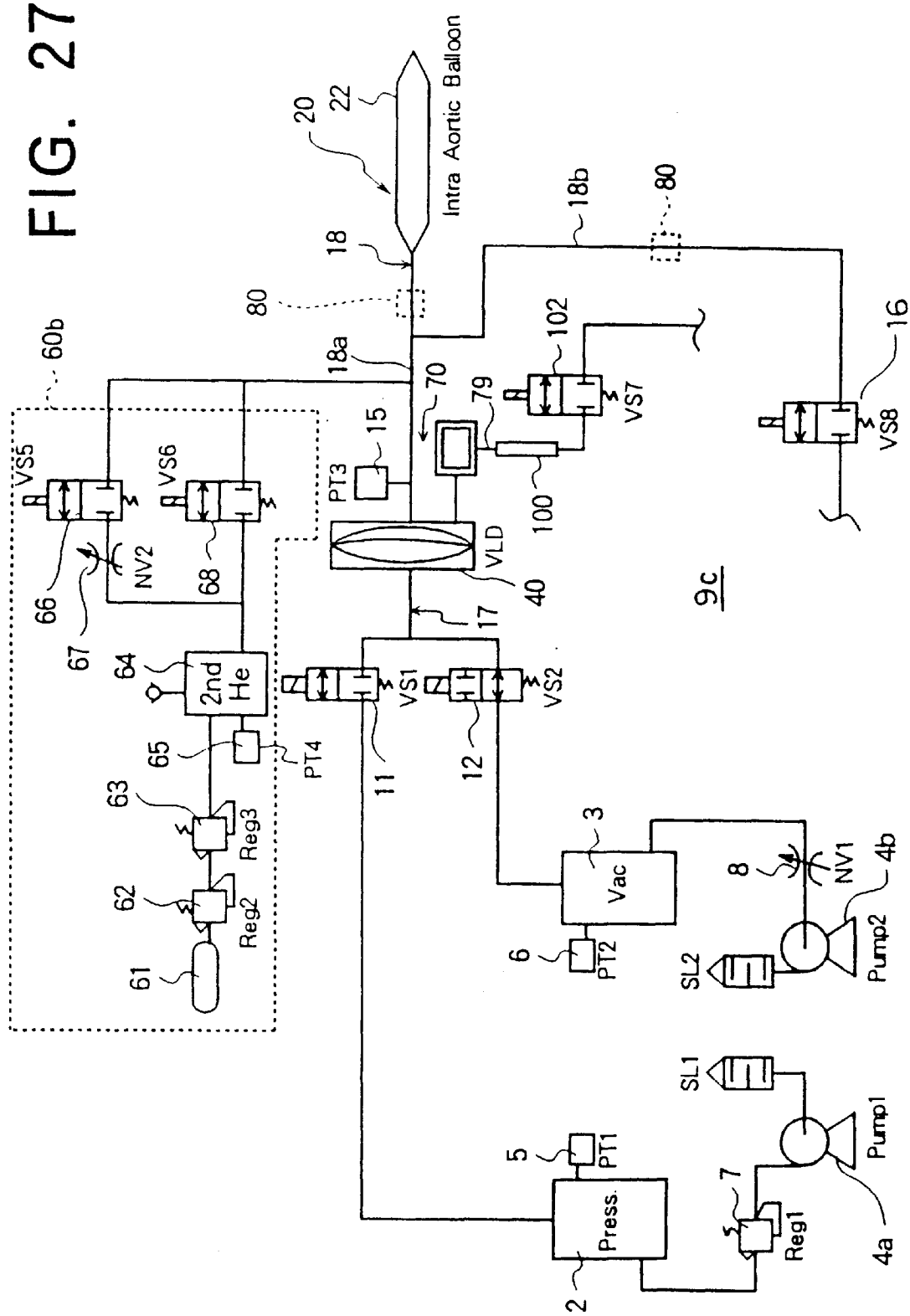
FIG. 27 is a schematic diagram of a driving apparatus in which the monitor is used.
Figure 28:
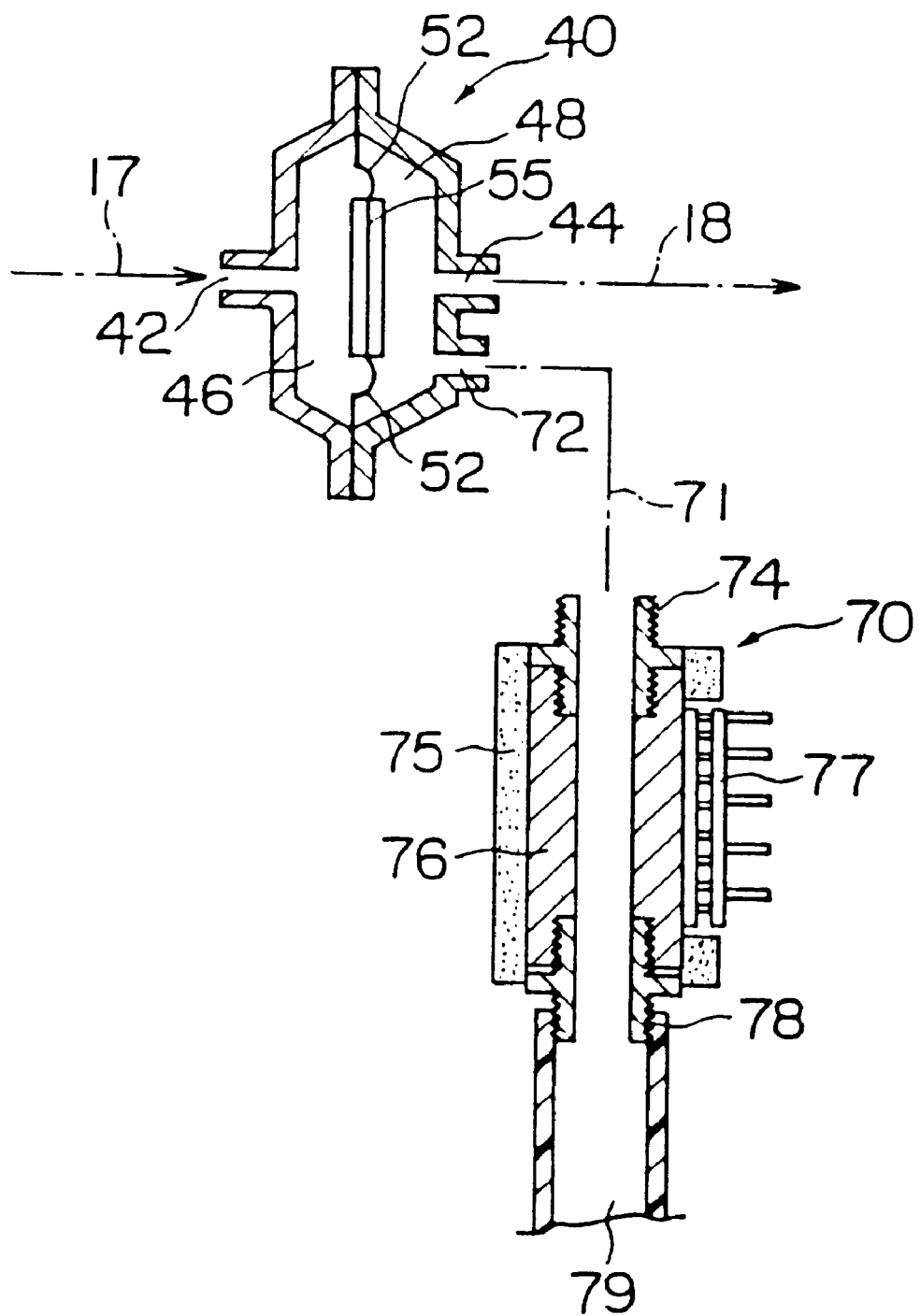
FIG. 28 is a cross-sectional view illustrating an example of pressure-transfer.

The first chamber 46 of the pressure-transfer isolator 40 is connected to the primary tube line 17, shown in FIG. 27, via an input port 42, while the second chamber 48 is connected to the secondary tube line 18 via an output port 44. The second chamber 48 is also connected via a port 72 to a moisture removal line 71, which will be described in detail below.

The first chamber 46 is isolated from the second chamber 48, and the driving fluid is blocked by the diaphragm 52. However, the pressure change (i.e., the volume change) of the first chamber 46 is transferred to the second chamber via the displacement of the diaphragm 52. This arrangement can allow the pressure change of the primary tube line 17 to be transferred to the secondary tube line 18 without connecting the primary tube line 17 to the secondary tube line 18. This also makes it easy to keep the volume (or the chemical equivalent) of the gas filled in the secondary tube line 18. Therefore, even if the gas leaks from the balloon 22 due to an unexpected accident, excessive gas leakage can be prevented.

The fluid flowing through the primary tube line 17 is air in this embodiment, and the fluid flowing through the secondary tube line 18 is helium gas, because the helium gas has a sufficiently small mass, which can improve the inflation/deflation response of the balloon 22.

As shown in FIG. 27, two pumps 4a and 4b are provided in the primary tube line 17. These pumps serve as pressure generators, where the first pump (or the compressor) 4a generates a positive pressure, and the second pump 4b generates a negative pressure. The positive-pressure output port of the first pump 4a is connected to a first (positive) pressure tank 2 via a regulator valve 7. The negative-pressure output port of the second pump 4b is connected to a second (negative) pressure tank 3 via a throttle valve 8.

The first and second pressure tanks 2 and 3 are furnished with pressure sensors 5 and 6, respectively, for detecting the interior pressures. The first and second pressure tanks 2 and 3 are also connected to the input ports of the first and second solenoid valves 11 and 12, respectively. The opening/closing operations of the solenoid valves 11 and 12 are controlled by a controller (not shown) so as to be consistent with the patient's heart beat. The output ports of the solenoid valves 11 and 12 are connected to the input port 42 (FIG. 28) of the pressure-transfer isolator 40 which functions as a secondary pressure generator.

The output port 44 of the pressure-transfer isolator 40, shown in FIG. 28, is connected to the secondary tube line 18, shown in FIG. 27. The secondary tube line 18, which comprises hoses and tubes, is a sealed line filled with the helium gas, and this sealed line is connected to the balloon 22. A pressure sensor 15 is provided to the secondary tube line 18 in order to detect the interior pressure of this line. The output of the pressure sensor 15 is supplied to the controller.

The secondary tube line 18 includes an exhaust line 18b which is branched off from the main line 18a. The exhaust line 18b is connected to an exhaust pump (not shown) via an solenoid valve 16. The solenoid valve 16 and the exhaust pump are used to evacuate the secondary tube line 18 in order to substitute helium gas for air prior to using the balloon catheter. This solenoid valve 16 is closed during the regular driving operation, and the exhaust pump is not activated. Instead of providing a separate exhaust pump, the second pump 4b may be used as the exhaust pump. If a system, in which the secondary tube line 18 (i.e., the driving tube line) is regularly evacuated to change the helium gas, is used, the exhaust pump is driven in the driving operation of the balloon 22, as necessary.

A gas supply system 60b is connected to the secondary tube line 18. The gas supply system 60b supplies a predetermined amount of helium gas to the secondary tube line 18 so that the chemical equivalent of the helium gas is kept constant in this tube line. Since the gas supply system 60b is the same as that shown in FIG. 10, the explanation thereof will be omitted here.

As shown in FIGS. 27 and 28, the moisture removal line 71 is connected to the secondary tube line 18 via the port 72 of the pressure-transfer isolator 40. To be more precise, the moisture removal line 71 is connected to the main line 18a of the secondary tube line 18 via the second chamber 48 of the pressure-transfer isolator 40.

The moisture removal line 71 connects the second chamber 48 of the pressure-transfer isolator 40 to the moisture condenser 70 which functions as a moisture remover.

The moisture condenser 70 has a tube connector 74 made of, for example, polyacetal resin having a high heat insulating ability, and a cooler 76 made of aluminum or stainless steel. The inner surface of the cooler 76 is smooth so that the water droplets easily slide down and drop off under a gravitational force. A part of the outer surface of the cooler 76 contacts one surface of a Pertier device that is cooled through heat absorption in the Pertier effect. The Pertier device is, for example, Thermo-module KSM-04017A manufactured by Komatsu Electronics Co., Ltd. The other surface of the Pertier device is provided with a cooling fin for releasing the heat generated by thermal transfer. The cooler 76 is covered with a heat insulating material 75 except for the surface areas that contact with the Pertier device and the cooling fin, whereby the inner surface of the cooler is kept at a low temperature with less electric power consumption. The cooling temperature is preferably 5 degrees below room temperature, but not lower than zero degrees so that the water droplets do not freeze.

Another tube connector 78, which is also made of an insulating material similar to the entrance tube connector 74, is provided to the other end of the cooler 76 so as to connect the cooler 76 to the drain tube 79. These insulating tube connectors 74 and 78 prevent the cooler 76 from being heated by thermal transfer from the tube lines connected thereto.

As shown in FIG. 27, the drain tube 79 is connected to a pool 100. Preferably, the pool 100 is provided with a level sensor which is disclosed in, for example, JP '068. The level sensor detects the water level of the pool 100. If the water level is sufficiently high, the solenoid valve 102 is opened to drain the water from the pool 100. It is preferable to open the solenoid valve 102 at a time when a positive pressure is applied to the secondary tube line 18 so that the positive pressure acts on the water surface of the pool 100 and urges the water to be drained quickly. This drain timing can also prevent the driving gas (e.g., the helium gas), filled in the secondary tube line 18, from leaking.

In general, moisture components contained in the patient's blood penetrate through the balloon 22, and the moisture vapor is mixed into the helium gas in the secondary tube line 18. The water condenser 70 is provided in order to remove such moisture vapor from the secondary tube line 18. The moisture removal line 71 may be branched off directly from the main line 18a of the secondary tube line 18. However, it is preferable to provide the moisture removal line 71 separately from the main line 18a because the moisture removing efficiency is improved, and because the water drops can be prevented from scattering into the main line 18a, through which the driving gas reciprocates at a high speed.

Next, the operations of the monitor 80 will be described with reference to FIGS. 25 and 26.

The monitor 80 detects if any blood is mixed into the secondary tube line 8. The monitor 80 comprises a light-emitting diode 84, which serves as the light-emitting device, and a photosensor diode 86, which serves as the light-receiving device. The light-emitting diode 84 is, for example, NLPB500 manufactured by Nichia Chemical Industry Co., Ltd, and the photosensor diode 86 is, for example, S1133 manufactured by Hamamatsu Photonics Co., Ltd. The diodes 84 and 86 are held by the casing 82 so that they are placed in opposite directions (i.e., at 180° from each other) with respect to the transparent tube that comprises the secondary tube line 18. The diodes 84, 86 that are positioned perpendicular to the longitudinal axis of the transparent tube. The casing 82 is preferably made of a material that can shut off external light from entering into the casing 82.

The diodes 84 and 86 may be positioned outside or inside the transparent tube of the secondary tube line 18. The light-emitting diode 84 emits blue or green light. If the fluid flowing through the tube is transparent, the photosensor diode 86 receives the light at a high level. If the fluid is colored with red by, for example, the patient's blood, the photodiode sensor 86 receives the light at a low level.

Figure 26:
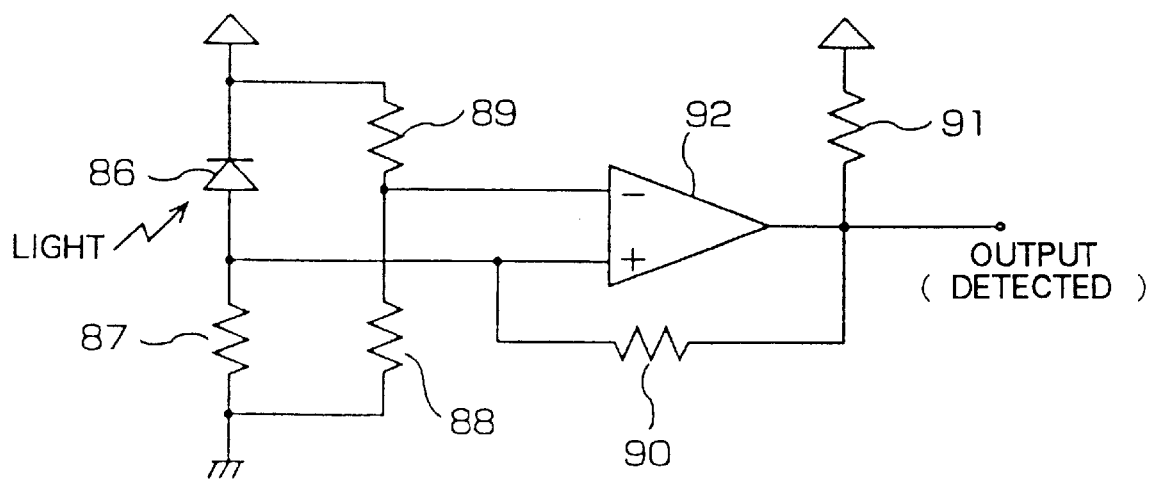
FIG. 26 is a circuit diagram of the monitor.

The photosensor diode 86 is connected in series with the resistor 87 between the ground and the constant voltage, as shown in FIG. 26. Resistors 88 and 89 are connected in parallel to the diode 86 and the resistor 87. The connecting point between the diode 86 and the resistor 87 is connected to the forward-phase input port of a comparator 92. The connecting point between the resistors 88 and 89 is connected to the inverse-phase input port. The output port of the comparator 92 is connected to the forward-phase input port via a high resistor 90 in order to avoid hysteresis. The output port of the comparator 92 is also connected to the constant voltage via a resistor 91.

When the photosensor diode is illuminated, it is in the ON state, and the forward-phase input port of the comparator 92 is at a higher level as compared with its inverse-phase input port. In this state, the output of the output port of the comparator 92 is at a high level. If the light level received by the photosensor diode 86 has decreased, the photosensor diode 86 is turned off and, as a result, the voltage level of the forward-phase input port of the comparator 92 is at lower than that of the inverse-phase input port. At this time, the output of the comparator 92 is at a low level.

The level change of the output port of the comparator 92 from the high level to the low level implies that the blue or green light emitted by the light-emitting diode is blocked before it reaches the photosensor diode 86, which further means that blood is mixed the secondary tube line 18. Thus, by detecting the level change, the monitor 80 can detect an undesirable state in which, for example, the patient's blood is mixed into the secondary tube line 18.

In this embodiment, the monitor 80, shown in FIG. 25, is placed in an arbitrary place in the main line 18a of the secondary tube line 18, shown in FIG. 27, or an arbitrary place in the exhaust line 18a that is branched off the main line 18a or, alternatively, it may be placed inan arbitrary position in the moisture removal line 71 (which is a part of the secondary tube line 18 and which includes the water condenser 70 the drain tube 79 and the water pool 100). One or more monitors 80 may be provided. It is preferably to provide the monitor 80 in the exhaust line 18b because if the system in which the secondary tube line 18 is evacuated regularly to change the helium gas, a pin hole is likely to be formed in the balloon 22 and the patient's blood is likely to be mixed into the line 18b. It is also preferable to provide the monitor 80 in the water pool 100 because the blood mixed into the secondary tube line is carried into the water pool 100. The monitor 80 may be provided to the catheter of the balloon catheter.

The operations of the medical-appliance driving apparatus 9c is similar to those of the driving apparatus 9b shown in FIG. 10, except for the monitor 80.

In this embodiment, the monitor 80, as well as the pressure sensor 15 for detecting the pressure change in this tube line, is provided to the secondary tube line 18. Because the photosensor diode 86 of the monitor 80 detects if there is any blood mixed into the secondary tube line 18, an abnormal operation due to, for example, a pin hole formed in the balloon 22, can be found earlier. Consequently, undesirable accidents, including coagulation of blood inside the secondary tube line 18 and balloon catheter 20, can be prevented in advance.

Tenth Embodiment

Figure 29:
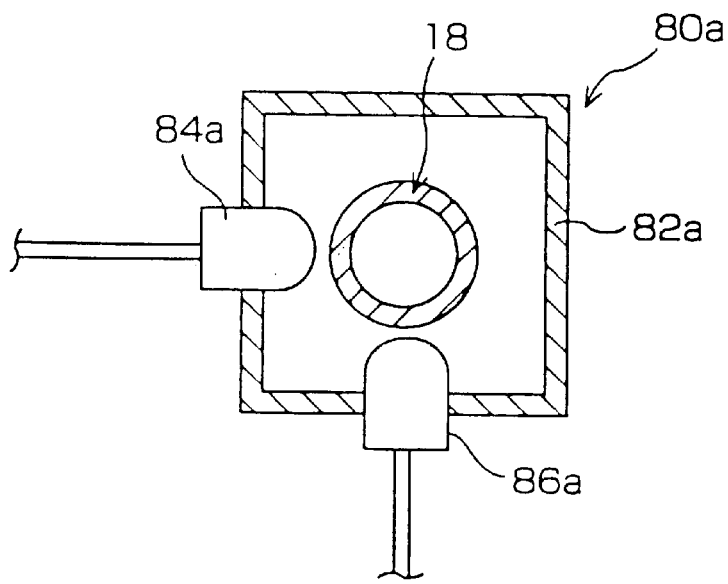
FIG. 29 is a schematic diagram of the monitor according to another embodiment of the present invention.
Figure 30:
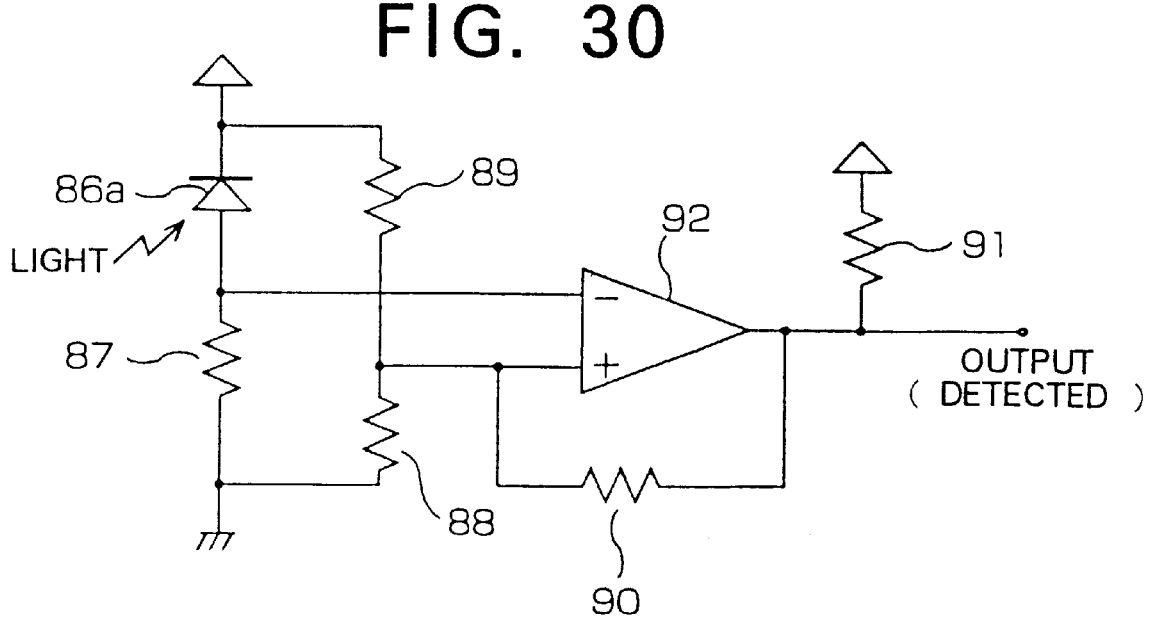
FIG. 30 is a circuit diagram of the monitor.

FIGS. 29 and 30 illustrates the major parts of the monitor 80a according to the tenth embodiment. The other structures are the same as that in the ninth embodiment, and the common explanation of those structures will be omitted here.

As shown in FIG. 29, the monitor 80a for detecting blood mixed in the secondary tube line 18 comprises a light-emitting diode 84a, which serves as a light-emitting device, and a photosensor diode 86a, which serves as a light-receiving device. These diodes 84a and 86a are held by the casing 82a so that they are perpendicular to the longitudinal axis of the transparent tube of the secondary tube line 18, and so that they are at a 90 degree angle with respect to the transparent tube. The casing 82a is preferably made of a material that can prevent external light from entering the casing 82a.

The diodes 84a and 86a may be positioned outside or inside the transparent tube of the secondary tube line 18. The light-emitting diode 84a emits red or yellow light. If the fluid flowing through the tube is transparent, the photosensor diode 86a does not receive the light emitted from the light-emitting diode 84a. On the other hand, if the fluid is colored with red by, for example, the patient's blood, the light emitted by the light-emitting diode 84a is diffused by the red fluid flowing in the secondary tube line 18, and this diffused light strikes the photosensor diode 86a. Upon receiving the diffused light, the photosensor diode 86a outputs a high level signal, which indicates that blood is mixed into the secondary tube line 18.

The photosensor diode 86a is connected in series with the resistor 87 between the ground and the constant voltage, as shown in FIG. 30. Resistors 88 and 89 are connected in parallel to the diode 86a and the resistor 87. The connecting point between the diode 86a and the resistor 87 is connected to the inverse-phase input port of a comparator 92. The connecting point between the resistors 88 and 89 is connected as the reference voltage to the forward-phase input port. The output port of the comparator 92 is connected to the forward-phase input port via a high resistor 90 in order to avoid hysteresis. The output port of the comparator 92 is also connected to the constant voltage via a resistor 91.

If the red or yellow light is not received by the photosensor diode 86a (at a low level), the photosensor diode 86a is in the OFF state, and the inverse-phase input port of the comparator 92 is at a lower level as compared with its forward-phase input port. In this state, the output of the output port of the comparator 92 is at a high level. If the photosensor diode 86a is illuminated by the diffused light, it is turned on and, as a result, the voltage level of the inverse-phase input port of the comparator 92 becomes higher than that of the forward-phase input port. At this time, the output of the comparator 92 becomes low.

Thus, by detecting the level change from the high level to the low level, the monitor 80a can detect the state in which the red or yellow light is diffused by the red colored fluid flowing in the secondary tube line 18, that is, in which the patient's blood is mixed into the secondary tube line 18.

The monitor 80a, shown in FIG. 29, can be placed in the same positions as described in the ninth embodiment, and it can achieve the same effect.

Eleventh Embodiment

Figure 31:
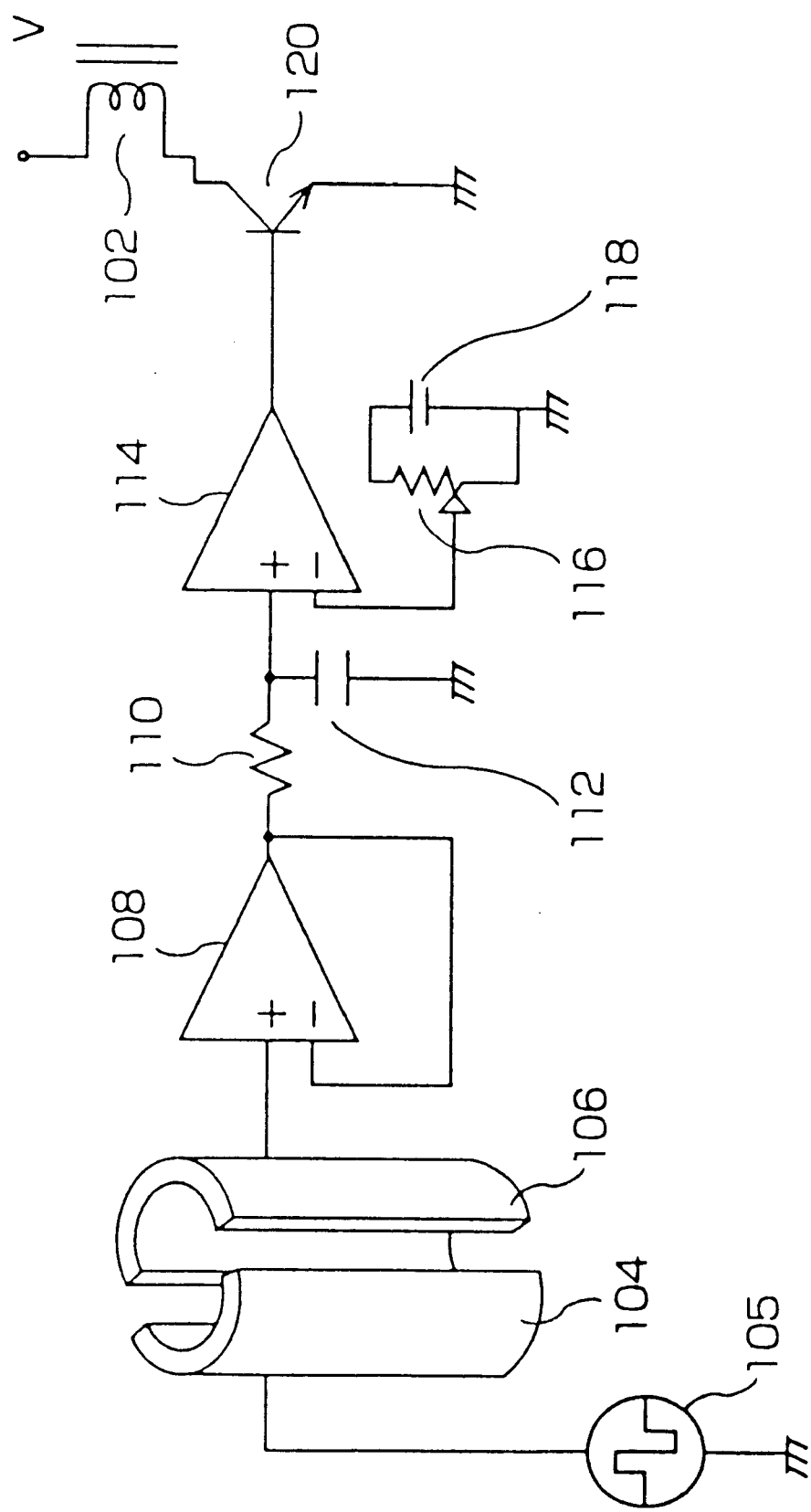
FIG. 31 is a circuit diagram of a water level sensor.

FIG. 31 illustrates the level sensor according to the eleventh embodiment. Although in the ninth embodiment, shown in FIG. 27, an optical type level sensor is attached to the water pool 100, a capacitance level sensor or a ultrasonic level sensor may be used instead. In the eleventh embodiment, a capacitance level sensor is used.

As shown in FIG. 31, two electrode plates 104 and 106 which are cylindrical half shells, are positioned around the water pool 100 (FIG. 27). An alternating current or AC oscillator 105 is connected to one electrode plate 104. The other electrode plate 106 is connected to the forward-phase input port of the operational amplifier 108. The inverse-phase input port of the operational amplifier 108 is connected to the output port of the operational amplifier 108. The output port of the operational amplifier 108 is then connected to the forward-phase input port of another operational amplifier 114 via a low-pass filter which comprises a resistor 110 and a capacitor 112. The inverse-phase input port of the operational amplifier 114 is connected to the reference voltage setting means which comprises a variable resistor 116 and a direct current or DC power source 118. By adjusting the resistance value of the variable resistor 116, the reference voltage (or the threshold voltage) is varied, and the minimum voltage of the forward-phase input port is determined so that the output port of the operational amplifier 114 is at a high level.

The output port of the operational amplifier 114 is connected to the base electrode of the transistor 120. When the output level of this output port becomes high, the transistor 120 is turned on to drive the driving coil of the solenoid valve 102, whereby the solenoid valve 102 is opened and the water is drained. The turn-on water level, where the transistor 120 is turned on, can be adjusted by the variable resistor 116.

According to the level sensor of this embodiment, the water level of the pool 100 (FIG. 27) is detected more accurately as compared to the optical-type level sensor.

The present invention is not limited to the embodiments described in the ninth through eleventh embodiments, and there are many changes which can be incorporated, without changing the spirit and the scope of the invention.

Figure 32:
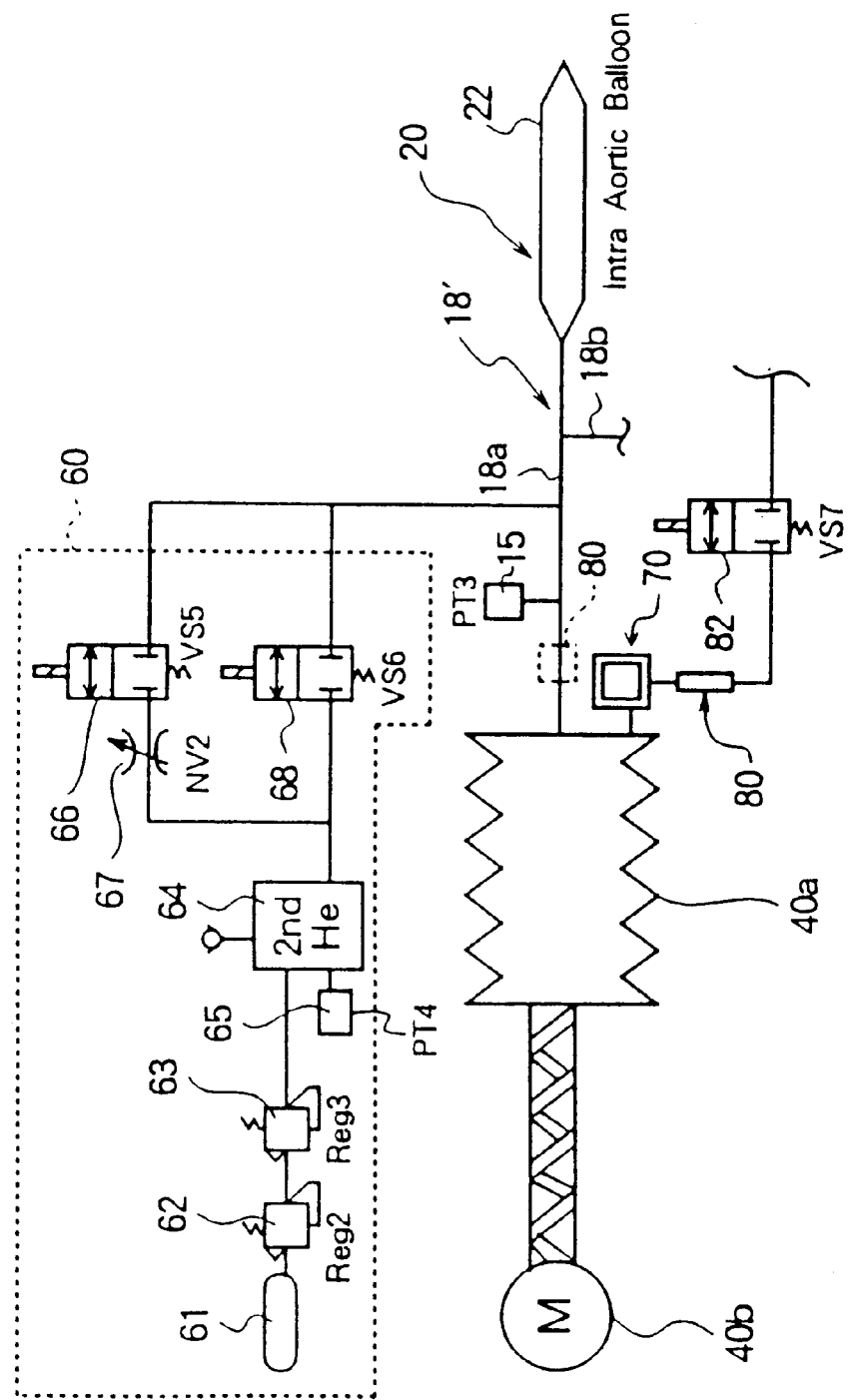
FIG. 32 is a schematic view of a driving apparatus in which a monitor, according to still another embodiment, is used.

For example, a pressure generator, that reciprocates the driving gas directly to and from the driving tube line 18', can be used without using the primary tube line 17 and the pressure-transfer isolator 40, as shown in FIG. 32. Such a pressure generator comprises, for example, a bellows 40a and driving means (e.g., a motor 40b) for expanding and compressing the bellows 40a in the axial direction. The inside or the outside of the bellows 40a is connected directly to the secondary tube line 18. By inflating and compressing the bellows 40a in the axial direction using the motor 40b, the driving gas is supplied and removed directly to and from the secondary tube line 18 at a predetermined timing, thereby inflating and deflating the balloon 22. The other structure is the same as that shown in FIG. 27.

Although, in the embodiments, a light emitting diode or LED is used as the light-emitting device, while a photodiode is used as the light-receiving device, many types of light-receiving devices, including a laser diode, a fluorescent tube with filter, a light bulb (filament lamp), a phototransistor, a Cds cell and a solar cell, can be used.

In the embodiment, a balloon catheter is driven by the medical-appliance driving apparatus. However, the driving apparatus of the present invention can be applied to various medical devices, for example, artificial hearts, that are driven by positive and negative pressures.

ACTUAL EXAMPLES

Some actual examples of the present invention, as well as the comparative examples, will be illustrated below. It should be noted that the present invention is not limited to these specific examples.

Example 1

A groove 154 having a width of 1 mm and a depth of 1 mm is formed in the inner surface 151 of the casing 144, as is shown in FIGS. 18A and 18B. The groove 154 extends from the output port 150 in opposite directions (i.e., 180 degrees apart). The total length of the groove 154 is 85 mm. The outer diameter of the casing 144 is 120 mm, and the thickness of the casing 144 is 16 mm. Two casings 144 with the same dimensions are assembled together. The volume of the inner space formed by these two casings 144 is about 56 cc.

A diaphragm 146, shown in FIGS. 16A through 16C, is placed to partition the inner space of the casings 144. The outer diameter of the diaphragm 146 is 115 mm. The thickness of the diaphragm 146 is 1.0 mm in the thickest portion thereof, and the thickness of the remaining part is 0.6 mm. The height of the annual sealing projection 147 is 0.25 mm on each side of the diaphragm 146 (and a total of 0.5 mm is on both sides).

Figure 21:
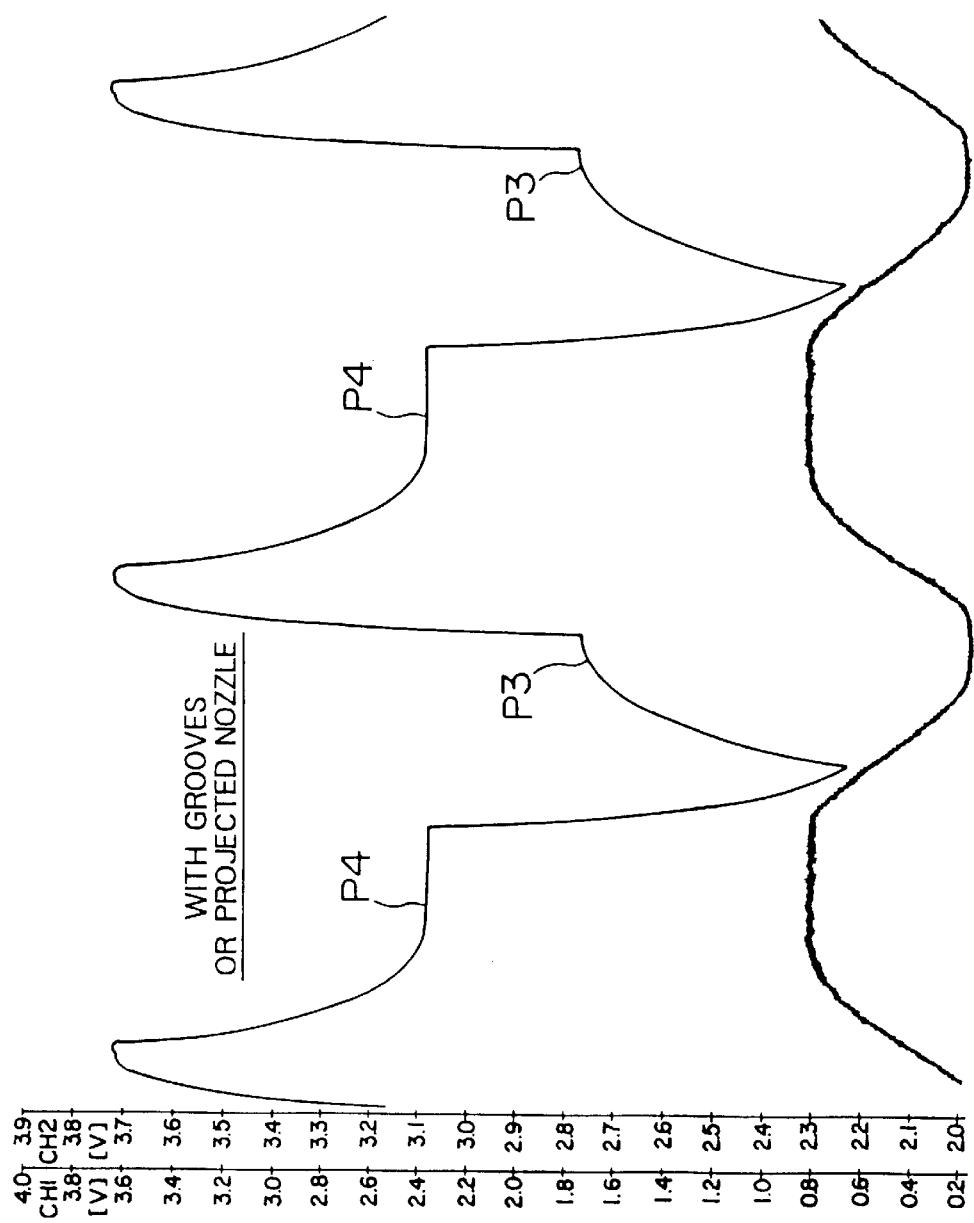
FIG. 21 is a graph showing a pressure change in the pressure-transfer isolator of an embodiment of the present invention.

The diaphragm 146 and the casings 144, shown in FIGS. 18A and 18B, comprise a pressure-transfer isolator, which is installed in the driving apparatus 9b, shown in FIG. 10. The driving apparatus 9b inflates and deflates the balloon 22 at a rate of 120 beats per minutes. The interior pressure was detected by the pressure sensor 15, shown in FIG. 10, and its pressure change was observed. The detection result is shown in FIG. 21. As shown in FIG. 21, no small peak SP (i.e., notch) was observed in the end of the plateau pressure P4.

Comparative Example 1

The same diaphragm and the same casings as those used in Example 1, but having no grooves formed on the inner surfaces thereof, are used to assemble a pressure-transfer isolator.

This pressure-transfer isolator is installed in the driving apparatus 9b shown in FIG. 10, and the balloon 22 is driven under the same conditions as in Example 1. The interior pressure was detected and the pressure change was observed. The detection result is shown in FIG. 22.

Unlike Example 1, a small peak SP (i.e., notch) appears at the end of each plateau pressure P4.

Comparative Example 2

The same casings as those used in Example 1, except for the point that the inner surfaces of the casings are roughened using silica sand having a diameter of about 80 μm, and the same diaphragm, are used to assemble a pressure-transfer isolator.

This pressure-transfer isolator is installed in the driving apparatus 9b shown in FIG. 10, and the balloon 22 is driven under the same conditions as in Example 1. The interior pressure was detected and the pressure change was observed. The detection result is the same as that in Comparative Example 1 shown in FIG. 22.

The small peak SP (i.e., notch) still appeared in the plateau pressure P4.

Example 2

The same casings as those in Example 1, but having no grooves, the same diaphragm as that in Example 1, and two nozzles 156, shown in FIG. 20B, are used to assemble a pressure-transfer isolator. The nozzles 156 are attached to the ports 148b and 150b, respectively, so that they project toward the inner space of the casings by 2 mm. The projecting amount is denoted by symbol "t" in FIG. 20A.

This pressure-transfer isolator is installed in the driving apparatus 9b, shown in FIG. 10, and the balloon 22 is driven under the same conditions as in Example 1. The interior pressure was detected and the pressure change was observed. The same result, as in Example 1 and shown in FIG. 21, was obtained.

Example 3

The same casings as those in Example 1, except for the point that a rib 154a is formed instead of the groove 154, and the same diaphragm as that in Example 1, are used to assemble a pressure-transfer isolator. The rib 154 extends from the port 150 in opposite directions (i.e., 180 degrees apart from each other), as shown in FIGS. 19A and 19B. The width of the rib 154a is 0.3 mm, the height is 0.3 mm, and the length in the radial direction is 35 mm.

Figure 23:
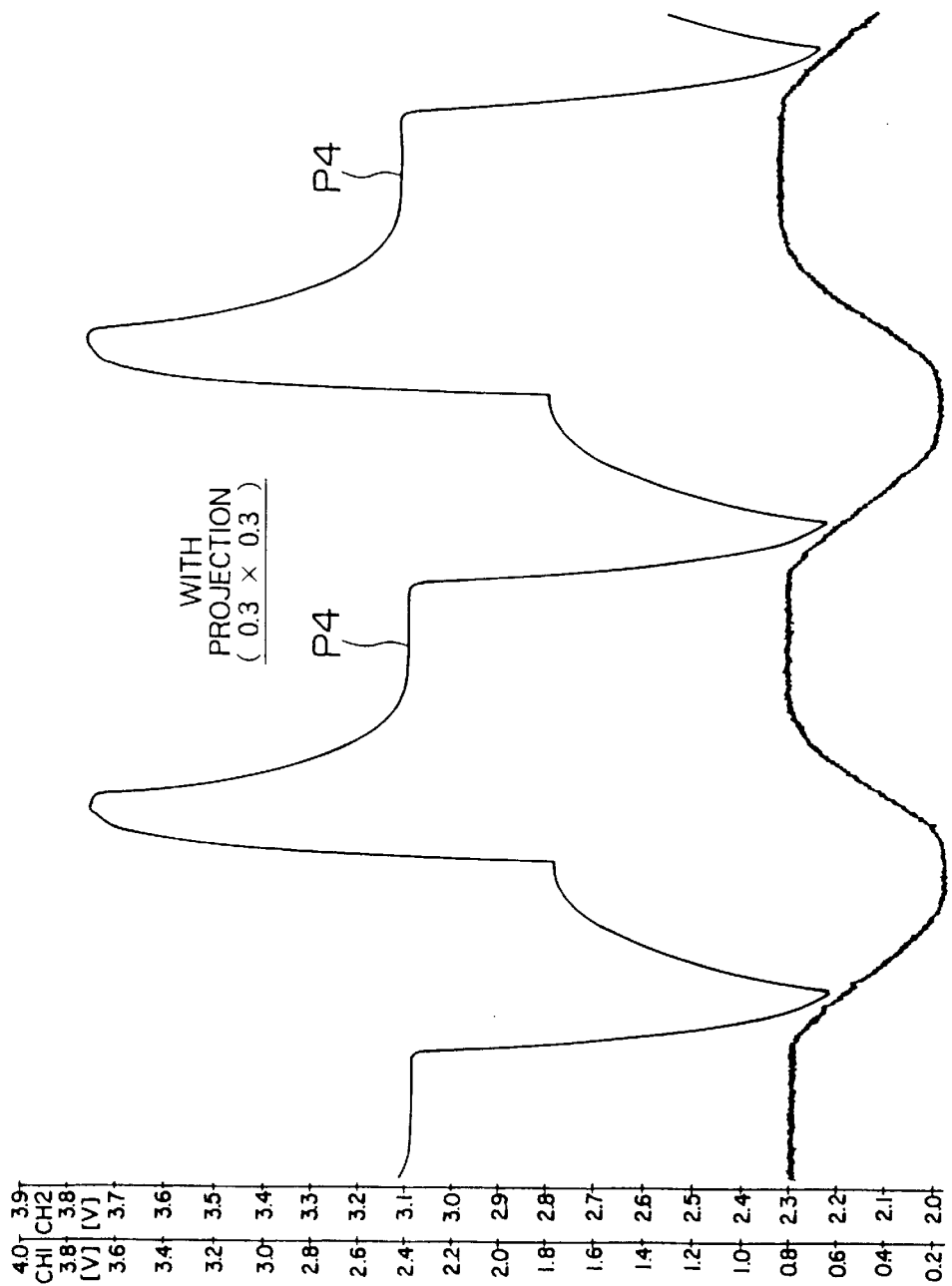
FIG. 23 is a graph showing a pressure change in the pressure-transfer isolator of another embodiment of the present invention.

This pressure-transfer isolator is installed in the driving apparatus 9b shown in FIG. 10, and the balloon 22 is driven under the same conditions as in Example 1. The interior pressure was detected and the pressure change was observed. The result is shown in FIG. 23, which indicates the same effect as that of Example 1.

Example 4

The same casings as those used in Example 3, except for the point that the height of the rib 154a is set to 0.15 mm, and the same diaphragm as that in Example 1, are used to assemble a pressure-transfer isolator.

Figure 24:
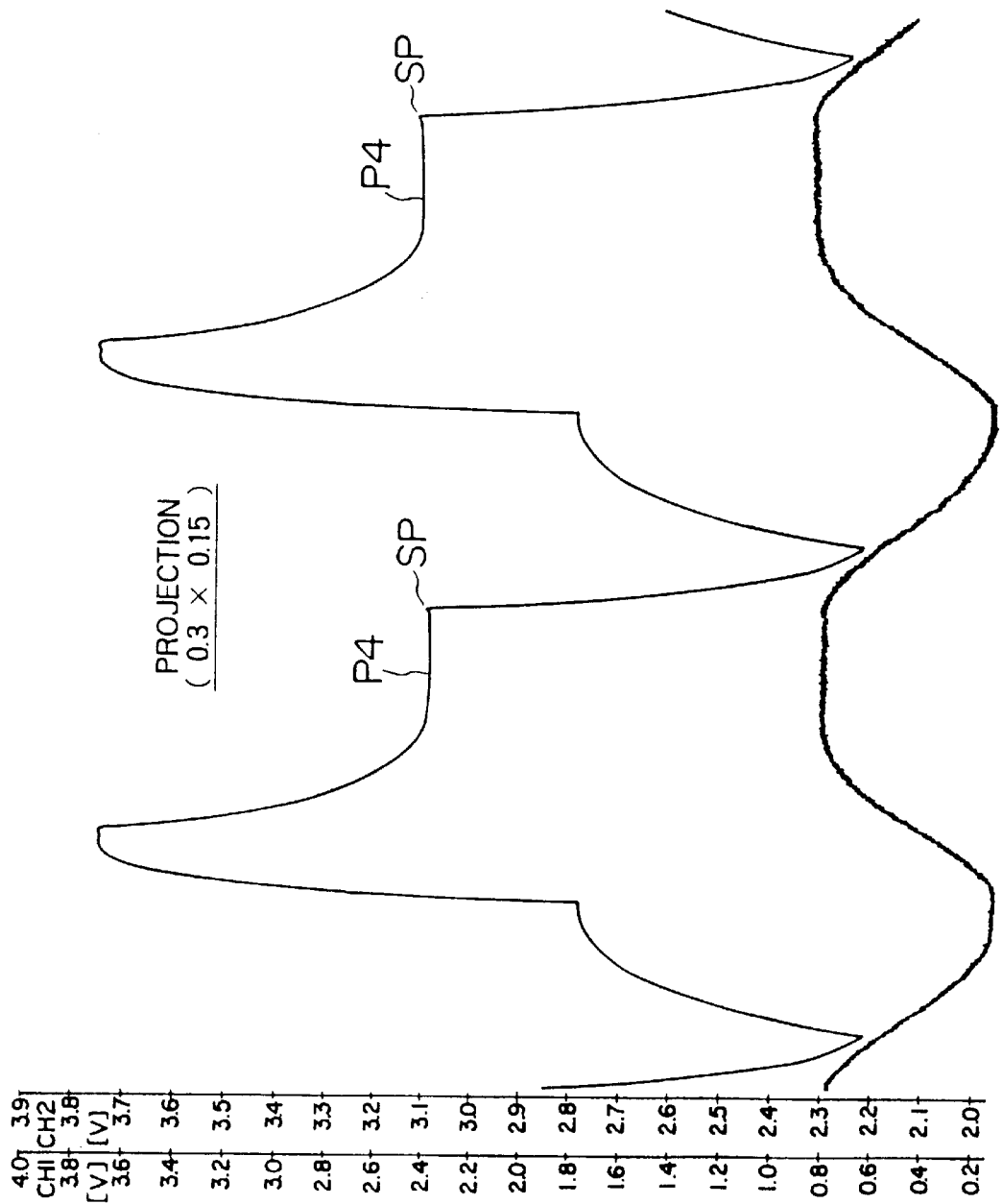
FIG. 24 is a graph showing a pressure change in the pressure-transfer isolator of still another embodiment of the present invention.

This pressure-transfer isolator is installed in the driving apparatus 9b shown in FIG. 10, and the balloon 22 is driven under the same conditions as in Example 1. The interior pressure was detected and the pressure change was observed. The detection result is shown in FIG. 24. Although there is a very small peak SP in each pulse, the amplitude of the small peak SP is greatly reduced, as compared with Comparative Examples above.

Example 5

A long straight projection is formed on either surface of the flexible membrane shown in FIG. 16 in the radial direction of the flexible membrane. The width of the projection is 0.5 mm, the height is 0.5 mm, and the length is 60 mm.

The same casings as those in Comparative Example 1, i.e., casings having no grooves on their surfaces, and the flexible membrane are used to form a pressure-transfer isolator.

This pressure-transfer isolator is installed in the driving apparatus 9b shown in FIG. 10, and the balloon 22 is driven under the same conditions as in Example 1. The interior pressure was detected and the pressure change was observed. The same result as in Example 1 was obtained.

What is claimed is:

1. A medical-appliance driving apparatus comprising:
    a pressure generator for alternately applying a positive pressure and a negative pressure to a tube line connected to a device to be driven in order to periodically inflate and deflate said device to be driven;
    a tube-line pressure sensor for detecting an interior pressure of said tube line;
    a gas supply system for supplying a gas into said tube line, said gas supply system comprising:
        a primary gas tank filled with a relatively high-pressure gas;
        a first valve connected to an output side of said primary gas tank;
        a secondary gas tank connected to said output side of said primary gas tank so as to allow gas flow therebetween when said first valve is open;
        a tank-pressure sensor for detecting an interior pressure of said secondary gas tank,
        and a second valve, connected to an output side of said secondary gas tank, for controlling a gas supply from said secondary gas tank into said tube line by opening and closing said second valve; and
    a controller for controlling an amount of said gas supplied to said tube line by said gas supply system, wherein when said interior pressure detected by said tube-line pressure sensor is not more than a predetermined pressure value, said controller closes said first valve and opens said second valve in order to allow said gas to be supplied from said secondary gas tank to said tube line, said controller calculating said amount of said gas supplied to said tube line based on a pressure change in said secondary gas tank detected by said tank-pressure sensor.

2. The medical-appliance driving apparatus according to claim 1, wherein said tube-line pressure sensor detects said interior pressure of said tube line at a timing of switching a state of said device being driven from a deflated state to an inflated state, and wherein said controller determines if said interior pressure detected by said tube-line pressure sensor is not more than the predetermined pressure value.

3. The medical-appliance driving apparatus according to claim 2, wherein said tube-line pressure sensor detects said interior pressure of said tube line at a timing of switching a state of said device being driven from a deflated state to an inflated state, and said gas supply system supplies said gas into said tube line so that said interior pressure of said tube line reaches the predetermined pressure value, said predetermined pressure value defining a gas supply timing of said gas supply system, and said controller being comprised so that said predetermined pressure value is changeable on demand.

4. The medical-appliance driving apparatus according to claim 1, wherein said gas supply system fills at first said tube line with said gas under a predetermined pressure, while keeping said device to be driven in a deflated state, said predetermined pressure being defined according to a volume of said device to be driven, and sampling said interior pressure detected by said tube-line pressure sensor at a timing of switching a state of said device to be driven from a deflated state to a inflated state, and supplying additional gas into said tube line so that said interior pressure detected by said tube-line pressure sensor reaches said predetermined pressure defined by said volume of said device to be driven.

5. The medical-appliance driving apparatus according to claim 1, further comprising a deflation duration detector for detecting a time length of deflation of said device to be driven, and an inflation suspending means for suspending an inflation of said device to be driven for at least one inflation cycle continuously when a deflation time detected is shorter than a predetermined time length, so that said deflation time approaches a predetermined time length, wherein said tube-line pressure sensor detects said interior pressure of said tube line at a timing of switching to the next inflation cycle after a suspension of said at least one inflation cycle, and said gas supply system supplies said gas to said tube line so that said interior pressure detected by said tube-line pressure sensor reaches the predetermined pressure value.

6. The medical-appliance driving apparatus according to claim 1, further comprising an inflation duration detector for detecting a time length of inflation of said device to be driven, and an inflation maintaining means for maintaining an inflation of said device to be driven for at least a predetermined time length when an inflation time is detected which is shorter than at least said predetermined time length, wherein said tube-line pressure sensor detects said interior pressure of said tube line at a timing of switching to the next deflation after a continuous inflation for at least said predetermined time length, and said gas supply system supplies said gas to said tube line so that said interior pressure detected by said tube-line pressure sensor reaches the predetermined pressure value.

7. The medical-appliance driving apparatus according to claim 1, further comprising a pressure change calculation means for calculating a time change rate of said interior pressure of said tube line detected by said tube-line pressure sensor at a timing of switching a state of said device to be driven from one of a deflated and inflated state to one of an inflated and deflated states, respectively, and a gas supply suspending means for suspending said gas supplied to said tube line when an absolute value of said time change rate is calculated to be greater than a predetermined rate value, wherein when said absolute value of said time change rate calculated by said pressure change calculation means is one of equal to and smaller than said predetermined rate value, said tube-line pressure sensor detects said interior pressure of said tube line at a timing of switching a state of said device to be driven from one of said deflated state and said inflated state to one of said inflated state and said deflated state, respectively, and wherein said gas supply system supplies said gas to the tube line so that said interior pressure detected by said tube-line pressure sensor reaches the predetermined pressure value.

8. The medical-appliance driving apparatus according to claim 1, wherein said tube line comprises a primary tube line and a secondary tube line, and a pressure-transfer isolator is provided in said tube line, said pressure transfer isolator allowing pressure transfer between said primary and secondary tube lines without allowing a gas flow between said primary and secondary tube lines.

9. The medical-appliance driving apparatus according to claim 8, wherein said pressure-transfer isolator comprises:
   a first casing having a first inner surface and a first port which is connectable to said primary tube line;
   a second casing having a second inner surface and a second port which is connectable to said secondary tube line;
   a flexible membrane placed in an inner space formed by said first and second casings so as to partition said inner space into a first chamber, which is connected to said first port, and a second chamber, which is connected to said second port, said flexible membrane oscillating between said first and second inner surfaces receiving a pressure change occurring in said first chamber; and
   at least one relief passage for driving residual fluid residing on said first and second inner surfaces away into said first and second ports, respectively, when said flexible membrane contacts either of said first and second surface.

10. The medical-appliance driving apparatus according to claim 9, wherein said at least one relief passage is at least one groove formed in any one of said first inner surface, said second inner surface, and both said first and second inner surfaces, said at least one groove extending in a radial direction from any one of said first port, said second port, and both said first and second ports.

11. The medical-appliance driving apparatus according to claim 9, wherein said at least one relief passage is at least one rib formed in any one of said first inner surface, said second inner surface, and both said the first and second inner surfaces, said at least one rib extending in a radial direction from any one of said first port, said second port, and both said first and second ports.

12. The medical-appliance driving apparatus according to claim 9, wherein said at least one relief passage is at least one hole formed on a side wall of a nozzle provided on any one of said first and said second port and projecting into one of said first chamber and said second chamber.

13. The medical-appliance driving apparatus according to claim 9, wherein said at least one relief passage is formed on at least one surface of said flexible membrane.

14. The medical-appliance driving apparatus according to claim 1, further comprising a body fluid sensor provided in a middle of said tube line in order to detect a body fluid mixed in said tube line.

15. The medical-appliance driving apparatus according to claim 14, wherein said body fluid sensor comprises an illumination device for illuminating a driving fluid flowing through said tube line, and a light-receiving device for receiving light emitted by said illumination device and passed through said driving fluid, said illumination device and said light-receiving device being designed so that in the absence of said body fluid contained in said driving fluid, a detection value of said light-receiving device is at a high level, and so that when said body fluid is contained in said driving fluid, then said detection value of said light-receiving means is at a low level.

16. The medical-appliance driving apparatus according to claim 14, wherein said body fluid sensor comprises an illumination device for illuminating a driving fluid flowing through said tube line, and a light-receiving device for receiving light emitted by said illumination device and reflected and diffused by said driving fluid, said illumination device and said light-receiving device being designed so that in the absence of said body fluid contained in said driving fluid, a detection value of said light-receiving device is at a low level, and when said body fluid is contained in said driving fluid, then said detection value of said light-receiving device is at a high level.

17. The medical-appliance driving apparatus according to claim 1, wherein said device to be driven is a balloon catheter for IABP.

18. The medical-appliance driving apparatus according to claim 1, wherein said device to be driven is an artificial heart.

19. A medical-appliance driving apparatus comprising:
   a pressure generator for alternately applying a positive pressure and a negative pressure to a tube line connected to a device to be driven so that said device to be driven inflates and deflates repeatedly;
   a tube-line pressure sensor for detecting an interior pressure of said tube line;
   a gas supply system for sampling said interior pressure detected by said tube-line pressure sensor at a timing of switching a state of said device to be driven from a deflated state to an inflated state and for supplying a gas into said tube line so that said interior pressure detected by said tube-line pressure sensor reaches a predetermined pressure value; and
   a controller for changing said predetermined pressure value.

20. A medical-appliance driving apparatus comprising:
   a primary pressure generator for alternately generating a positive pressure and a negative pressure;

a secondary pressure generator comprising a pressure-transfer isolator, said pressure-transfer isolator having a first chamber, to which said positive pressure and said negative pressure generated by said primary pressure generator are introduced via a primary tube line, and a second chamber which is isolated from said first chamber in a sealed manner, to which at least a portion of said positive and negative pressures in said first chamber is transferred;

a secondary tube line connected to the second chamber and to a device to be driven so as to repeat inflation and deflation;

a pressure sensor for detecting an interior pressure of said secondary tube line;

a gas supply system for first filling said secondary tube line with a gas under a predetermined pressure, while keeping said device to be driven in a deflated state, said predetermined pressure being defined according to a volume of said device to be driven, and sampling said interior pressure detected by said tube-line pressure sensor at a timing of switching a state of said device to be driven from a deflated state to an inflated state, and supplying additional gas into said secondary tube line so that said interior pressure detected by said tube-line pressure sensor reaches said predetermined pressure defined by said volume of said device to be driven; and a controller for changing said predetermined pressure.

21. The medical-appliance driving apparatus according to any one of claims 19 and 20, wherein said controller is adapted to lower said predetermined pressure when said volume of said device to be driven is small.

22. A medical-appliance driving apparatus comprising:

a pressure generator for alternately applying a positive pressure and a negative pressure to a tube line connected to a device to be driven so that said device to be driven inflates and deflates repeatedly;

a deflation time calculation means for calculating a time length of deflation of said device to be driven;

an inflation suspending means for suspending an inflation of said device to be driven for at least one continuous inflation cycle when a calculated deflation time is shorter than a first predetermined value so that said calculated deflation time approaches said first predetermined value;

a pressure sensor for detecting said interior pressure of said tube line at a timing of switching to the next inflation cycle after a suspension of said at least one continuous inflation cycle; and a gas supply system for supplying a gas into said tube line so that said interior pressure detected by said pressure sensor approaches a second predetermined value.

23. A medical-appliance driving apparatus comprising:

a pressure generator for alternately applying a positive pressure and a negative pressure to a tube line connected to a device to be driven so that said device to be driven inflates and deflates repeatedly;

an inflation time calculation means for calculating a time length of inflation of said device to be driven;

an inflation maintaining means for maintaining said inflation of said device to be driven for at least a first predetermined time length when a detected inflation time is shorter than said at least first predetermined time length;

a pressure sensor for detecting an interior pressure of said tube line at a timing of switching to the next deflation cycle after said inflation continuously for said at least first predetermined time length; and a gas supply system for supplying a gas into said tube line so that said interior pressure detected by said pressure sensor approaches a second predetermined value.

24. A medical-appliance driving apparatus comprising:

a pressure generator for alternately applying a positive pressure and a negative pressure to a tube line connected to a device to be driven so that said device to be driven inflates and deflates repeatedly;

a pressure sensor for detecting an interior pressure of said tube line;

a pressure change calculation means for calculating a time change rate of said interior pressure of said tube line detected by said pressure sensor at a timing of switching to one of an inflated state and a deflated state from one of the deflated state and the inflated state, respectively;

a gas supply suspending means for suspending a supply of gas to said tube line when an absolute value of a time change rate calculated by said pressure change calculation means is greater than a first predetermined value, a gas supply system for supplying said gas to said tube line, when said absolute value of said time change rate calculated by said pressure change calculation means is any one of equal to and smaller than said first predetermined value, so that said interior pressure detected by said pressure sensor at a timing of switching reaches a second predetermined value.

* * * * *